US007872094B2

(12) United States Patent  
May et al.

(10) Patent No.: US 7,872,094 B2
(45) Date of Patent: *Jan. 18, 2011

(54) ANTI-INFLAMMATORY COMPOUNDS AND USES THEREOF

(75) Inventors: Michael J. May, New Haven, CT (US); Sankar Ghosh, Madison, CT (US)

(73) Assignee: Yale University, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/424,334

(22) Filed: Apr. 15, 2009

(65) Prior Publication Data

US 2009/0286736 A1 Nov. 19, 2009

Related U.S. Application Data

(60) Continuation of application No. 10/979,683, filed on Nov. 1, 2004, now Pat. No. 7,538,089, which is a division of application No. 09/847,940, filed on May 2, 2001, now Pat. No. 6,831,065, which is a continuation-in-part of application No. 09/643,260, filed on Aug. 22, 2000, now Pat. No. 6,864,355.

(60) Provisional application No. 60/201,261, filed on May 2, 2000.

(51) Int. Cl.
 A61K 38/00 (2006.01)
 A61K 38/04 (2006.01)
 A01N 1/02 (2006.01)
 A01N 25/00 (2006.01)

(52) U.S. Cl. .................. 530/300; 530/324; 530/329; 435/2; 514/789

(58) Field of Classification Search .................. None
See application file for complete search history.

(56) References Cited

U.S. PATENT DOCUMENTS

| | | | |
|---|---|---|---|
| 5,166,133 | A | 11/1992 | Houston et al. |
| 5,804,374 | A | 9/1998 | Baltimore et al. |
| 5,851,812 | A | 12/1998 | Goeddel et al. |
| 5,939,302 | A | 8/1999 | Goeddel et al. |
| 5,972,655 | A | 10/1999 | Marcu |
| 6,030,834 | A | 2/2000 | Chu et al. |
| 6,831,065 | B2 | 12/2004 | May et al. |
| 6,864,355 | B1 | 3/2005 | May et al. |
| 7,049,395 | B2 | 5/2006 | May et al. |
| 7,534,858 | B2 | 5/2009 | May et al. |
| 7,538,089 | B2 | 5/2009 | May et al. |
| 2002/0156000 | A1 | 10/2002 | May et al. |
| 2003/0054999 | A1 | 3/2003 | May et al. |
| 2005/0143302 | A1 | 6/2005 | May et al. |
| 2006/0293244 | A1 | 12/2006 | May et al. |
| 2009/0286748 | A1 | 11/2009 | May et al. |

OTHER PUBLICATIONS

Britta-Mareen, E. et al., "Physphorylation of human IκB-α on serines 32 and 36 controls IκB-α proteolysis and NF-κB activation in response to diverse stimuli," *The EMBO Journal*, vol. 14(12):2876-2883 (1995).

Chu, Z-L. et aL, "IKKY Mediates the Interaction of Cellular IκB Kinase with the Tax Transforming Protein of Human T Cell Leukemia Virus Type 1." *The Journal of Biological Chemistry*, vol. 274, No. 22, pp. 15297-15300 (1999).

Delhase, et al., "Positive and Negative Regulation of IκB Kinase Activity Through IKK beta Subunit Phosphorylation." *Science*, vol. 284, pp. 309-313 (1999).

DiDonato, J.A. et al., "A cytokine-responsive IκB Kinase that activates the transcription factor NF—κB." *Nature*, vol. 388, pp. 548-554 (1997).

DiDonato, J.A. et al., "Mapping of the Inducible IκB Phosphorylation Sites That Signal Its Ubiquitination and Degradation." *Molecular and Cellular Biology*, vol. 16, No. 4, pp. 1295-1304 (1996).

Ghosh, S. et aL, "NF-κB and Rel Proteins: Evolutionarily Conserved Mediators of Immune Responses." *Annu. Rev. Immunol.* vol. 16, pp. 225-260 (1998).

Huang, Cheng-Han et al., "Remodeling of the Transmembrane Segment in Human Glycophorin by Aberrant RNA Splicing," *The Journal of Biological Chemistry*, vol. 269(14):10804-10812 (1994).

Harhaj, E.W. et al., "IKKγ Serves as a Docking Subunit of the IκB Kinase (IKK) and Mediates Interaction of IKK with the Human T-cell Leukemia Virus Tax Protein." *The Journal of Biological Chemistry*, vol. 274, No. 33, pp. 22911-22914 (1999).

Hatada, Eunice N., et al. NF-kappaB and the Innate Immune Response. *Current Opinion in Immunology*, vol. 12, pp. 52-58 (2000).

Houston et al., "Method for inhibiting adhesion of white blood cells to endothelial cells," Database: Issued_Patents_AA, Accession No.: US-07-700-526-17, Aug. 16, 1991.

Hu, Y. et al., "Abnormal Morphogenesis but Intact IKK Activation in Mice lacking the IKKα Subunit of IκB Kinase." *Science*, vol. 284, pp. 316-320 (1999).

Israël, A., "The IKK complex: An Integrator of All Signals that Activate NF-kappaB?" *Trends in Cell Biology*, vol. 10, pp. 129-133 (2000).

Jin, Dong-Yan et al., "Role of Adapter Function in Oncoprotein-mediated Activation of NF-κB," *The Journal of Biological Chemistry*, vol. 274(25):17402-17405 (1999).

Jin, Dong-Yan et al., "Isolation of Full-Length cDNA and Chromosomal Localization of Human NF-κB Modulator NEMO to Xq28," *Journal of Biomedical Science*, vol. 6:115-120 (1999).

Karin, M., et al., "Phosphorylation Meets Ubiquitination: The Control of NF-kappaB Activity", *Annual Review of Immunology*, vol. 18, pp. 621-663 (2000).

Kopp, E. et al., "Inhibiton of NF-κB by Sodium Salicylate and Aspirin." *Science*, vol. 265, pp. 956-959 (1994).

(Continued)

*Primary Examiner*—Suzanne M Noakes
*Assistant Examiner*—Jae W Lee
(74) *Attorney, Agent, or Firm*—McCarter & English, LLP; Maria Laccotripe Zacharakis; Deborah L. Nagle

(57) ABSTRACT

The present invention provides anti-inflammatory compounds, pharmaceutical compositions thereof, and methods of use thereof for treating inflammatory disorders. The present invention also provides methods of identifying anti-inflammatory compounds and methods of inhibiting NF-κB-dependent target gene expression in a cell.

25 Claims, 24 Drawing Sheets

OTHER PUBLICATIONS

Li, Q. et al., "Severe Liver Degeneration in Mice Lacking the IκB Kinase 2 Gene." *Science*, vol. 284, pp. 321-325 (1999).

May, M.J. et al. "Rel/NF-κB and IκB proteins: an overview." *Cancer Biology*, vol. 8 pp. 63-73 (1997).

May, M.J. et al. "Selective inhibition of NF-κB activation by a peptide that blocks the interaction of NEMO with the IκB kinase complex." *Science*. vol. 289, No. 5484, pp. 1550-4 (2000).

May, M.J. et al. "Signal Transduction through NF-κB." *Immunolgy Today*, vol. 19, No. 2, pp. 80-88 (1998).

Mercurio, F. et al., "IκB Kinase (IKK)-Associated Protein 1, a Common Component of the Heterogeneous IKK Complex." *Molecular and Cellular Biology*, vol. 19, No. 2, pp. 1526-1538 (1999).

Mock, et al., "A Conserved Helix-Loop-Helix Ubiquitous Kinase, Maps to Human Chromosome 10 and Mouse Chromosome 19." *Genomics* vol. 27, pp. 348-351 (1995).

Ngo, et al., in "The Protein Folding Problem and Tertiary Structure Prediction", Merz, et al. (ed.), Birkhauser, Boston, MA, pp. 433 and 492-495 (1994).

Regnier, C.H. et al., "Identification and Characterization of an IκB Kinase." *Cell*, vol. 90, pp. 373-383 (1997).

Rothwarf, D.M. et al., "IKK-γ is an essential regulatory subunit of the IκB kinase complex." *Nature*, vol. 395, pp. 297-300 (1998).

Rudolph, D. et al., "Severe liver degeneration and lack of NF-κB activation in NEMO/IKKγ-deficient mice." *Genes & Development*, vol. 14, pp. 854-862 (2000).

Siebenlist, U. et al., "Structure, Regulation and Function of NF- κB." *Annu. Rev. Cell. Biol.*, vol. 10, pp. 405-455 (1994).

Takeda, K. et al., "Limb and Skin Abnormalities in Mice Lacking IKKα." *Science*, vol. 284, pp. 313-316 (1999).

Yamaoka, S. et al., "Complementation Cloning of NEMO, a Component of the IκB Activation." *Cell*, vol. 93, pp. 1231-1240 (1998).

Ye, J. et al., "Regulation of the NF-κB Activation Pathway by Isolated Domains of FIP3/IKKγ, a Component of the IκB-γ Kinase Complex." *The Journal of Biological Chemistry*, vol. 275, No. 13, pp. 9882-9889 (2000).

Zandi, E. et al. "The IκB kinase complex (IKK) contains two kinase subunits, IKKα and IKKβ, necessary for IκB phosphorylation and NF-κB activation." *Cell*. vol. 91, No. 2, pp. 243-252 (1997).

Zhang, S. Q. et al., "Recruitment of the IKK Signalosome to the p55 TNF Receptor: RIP and A20 Bind to NEMO (IKK γ) upon Receptor Stimulation." *Immmunity*, vol. 12, pp. 301-311 (2000).

Zhong, H. et al., "The Transcriptional Activity of NF-κB Is Regulated by the IκB-Associated PKAc Subunit through a Cyclic AMP-Independent Mechanism." *Cell*, vol. 89, pp. 413-424 (1997).

IKKβ (721-756) NAIQ D TV RE QD Q SF TA L D W S W L QT EE EE H S C L E Q A S

*WILD-TYPE:* drqikiwfqnrrmkwkkTALD<u>W</u>S<u>W</u>LQTE
*MUTANT:* drqikiwfqnrrmkwkkTALD<u>A</u>S<u>A</u>LQTE
Fig. 5A
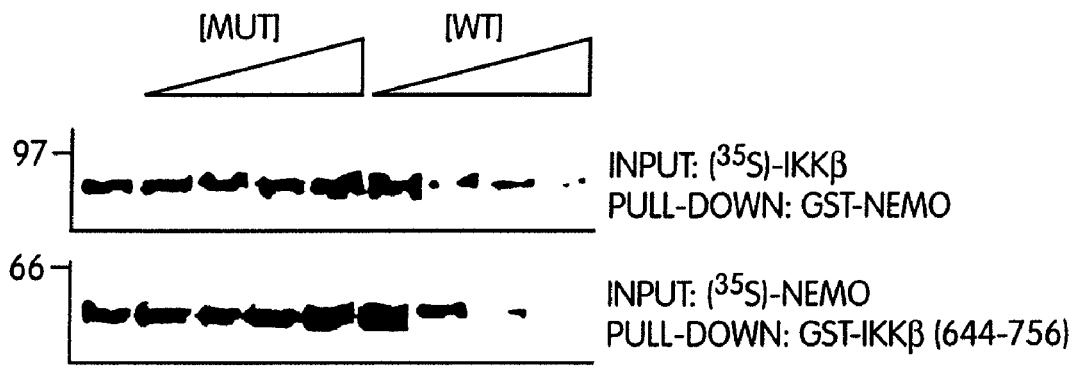
Fig. 5B
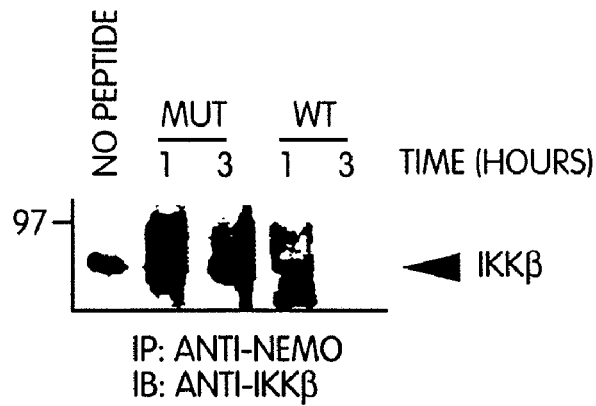
Fig. 5C

SEQUENCE LISTING

<160> NUMBER OF SEQ ID NOS: 27

<210> SEQ ID NO 1
<211> LENGTH: 32
<212> TYPE: DNA
<213> ORGANISM: Homo sapiens

<400> SEQUENCE: 1
tcacggccct agactggagc tggttacaga cg                32

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: NBD mutants

<400> SEQUENCE: 2

Leu Asp Trp Ser Trp Leu
  1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: NBD mutants

<400> SEQUENCE: 3

Leu Asp Ala Ser Ala Leu
 1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: NBD mutants

<400> SEQUENCE: 4

Ala Asp Trp Ser Trp Leu
 1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: NBD mutants

<400> SEQUENCE: 5

Leu Asp Trp Ser Trp Ala
 1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: NBD mutants

<400> SEQUENCE: 6

Ala Asp Trp Ser Trp Ala
 1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: NBD mutants

<400> SEQUENCE: 7

Leu Ala Trp Ser Trp Leu
 1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: NBD mutants

<400> SEQUENCE: 8

Leu Glu Trp Ser Trp Leu
 1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: NBD mutants

<400> SEQUENCE: 9

Leu Asn Trp Ser Trp Leu

-continued

```
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: NBD mutants

<400> SEQUENCE: 10

Leu Asp Ala Ser Trp Leu
  1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: NBD mutants

<400> SEQUENCE: 11

Leu Asp Phe Ser Trp Leu
  1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: NBD mutants

<400> SEQUENCE: 12

Leu Asp Tyr Ser Trp Leu
  1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: NBD mutants

<400> SEQUENCE: 13

Leu Asp Trp Ser Ala Leu
  1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: NBD mutants

<400> SEQUENCE: 14

Leu Asp Trp Ser Phe Leu
  1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: NBD mutants

<400> SEQUENCE: 15

Leu Asp Trp Ser Tyr Leu
  1               5
```

```
<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: NBD mutants

<400> SEQUENCE: 16

Leu Asp Trp Ala Trp Leu
 1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: NBD mutants

<400> SEQUENCE: 17

Leu Asp Trp Glu Trp Leu
 1               5

<210> SEQ ID NO 18
<211> LENGTH: 28
<212> TYPE: PRT
<213> ORGANISM: Artificial Sequence
<220> FEATURE:
<223> OTHER INFORMATION: Description of Artificial Sequence: NBD
      peptides

<400> SEQUENCE: 18

Asp Arg Gln Ile Lys Ile Trp Phe Gln Asn Arg Arg Met Lys Trp Lys
 1               5                  10                  15

Lys Thr Ala Leu Asp Trp Ser Trp Leu Gln Thr Glu
            20                  25

<210> SEQ ID NO 19
<211> LENGTH: 28
<212> TYPE: PRT
<213> ORGANISM: Artificial Sequence
<220> FEATURE:
<223> OTHER INFORMATION: Description of Artificial Sequence: NBD
      peptides

<400> SEQUENCE: 19

Asp Arg Gln Ile Lys Ile Trp Phe Gln Asn Arg Arg Met Lys Trp Lys
 1               5                  10                  15

Lys Thr Ala Leu Asp Ala Ser Ala Leu Gln Thr Glu
            20                  25

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: primers

<400> SEQUENCE: 20
atagacgaat tcaataggca cctctggaag                                    30

<210> SEQ ID NO 21
<211> LENGTH: 31
<212> TYPE: DNA
<213> ORGANISM: Artificial Sequence
<220> FEATURE:
```

-continued

<223> OTHER INFORMATION: Description of Artificial Sequence: primers

<400> SEQUENCE: 21
taggacctcg agctactcaa tgcactccat g           31

<210> SEQ ID NO 22
<211> LENGTH: 36
<212> TYPE: DNA
<213> ORGANISM: Artificial Sequence
<220> FEATURE:
<223> OTHER INFORMATION: Description of Artificial Sequence: primers

<400> SEQUENCE: 22
ctagtcgaat tcaccatgca gagcacagcc aattac           36

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: primers

<400> SEQUENCE: 23
ctagtctcta gattagacat caggaggtgc tgg           33

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: primers

<400> SEQUENCE: 24
ttagattggt cttggtta           18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: primers

<400> SEQUENCE: 25
ttggactggt cctggcta           18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: primers

<400> SEQUENCE: 26
ttagattggt cttatctg           18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: primers

<400> SEQUENCE: 27
cttgactggt catactta           18

ANTI-INFLAMMATORY COMPOUNDS AND USES THEREOF

RELATED APPLICATIONS

This application is a continuation of U.S. patent application Ser. No. 10/979,683, filed on Nov. 1, 2004, which is a divisional of U.S. patent application Ser. No. 09/847,940 filed May 2, 2001, issued as U.S. Pat. No. 6,831,065 on Dec. 14, 2004, which is a continuation-in-part of U.S. patent application Ser. No. 09/643,260 filed Aug. 22, 2000, issued as U.S. Pat. No. 6,864,355 on Mar. 8, 2005, which claims priority to U.S. Provisional Patent Application No. 60/201,261 filed May 2, 2000, now expired. The entire contents of each of the foregoing patents and applications are expressly incorporated herein by reference.

U.S. GOVERNMENT SUPPORT

This work was supported by a grant from the National Institute of Health (AI33443).

FIELD OF THE INVENTION

The invention relates to compositions and methods for the selective inhibition of cytokine-mediated NF-κB activation by blocking the interaction of NEMO with IκB kinase-β (IKKβ) at the NEMO binding domain (NBD). The blockade of IKKβ-NEMO interaction results in inhibition of IKKβ kinase activation and subsequent decreased phosphorylation of IκB. Phosphorylation of IκB is an integral step in cytokine-mediated NF-κB activation.

BACKGROUND OF THE INVENTION

NF-κB is a transcription factor which mediates extracellular signals responsible for induction of genes involved in pro-inflammatory responses (Baltimore et al., (1998) U.S. Pat. No. 5,804,374). NF-κB is anchored in the cytoplasm of most non-stimulated cells by a non-covalent interaction with one of several inhibitory proteins known as IκBs (May & Ghosh, (1997) Semin. Cancer. Biol. 8, 63-73; May & Ghosh, (1998) Immunol. Today 19, 80-88; Ghosh et al., (1998) Annu. Rev. Immunol. 16, 225-260). Cellular stimuli associated with pro-inflammatory responses such as TNFα, activate kinases, which in turn activate NF-κB by phosphorylating IκBs. The kinases that phosphorylate IκBs are called IκB kinases (IKKs).

Phosphorylation targets IκBs for ubiquitination and degradation. The degradation and subsequent dissociation of IκBs from NF-κB reveals the nuclear localization signal on NF-κB, resulting in nuclear translocation of active NF-κB, leading to up-regulation of genes responsive to NF-κB (May & Ghosh, (1997) Semin. Cancer. Biol. 8, 63-73; May & Ghosh, (1998) Immunol. Today 19, 80-88; Ghosh et al., (1998) Annu. Rev. Immunol. 16, 225-260; Siebenlist et al., (1994) Annu. Rev. Cell Biol. 12, 405-455). Phosphorylation of IκBs is therefore an essential step in the regulation of NF-κB mediated pro-inflammatory responses.

The identification and characterization of kinases that phosphorylate IκBs has led to a better understanding of signaling pathways involving NF-κB activation. Several different subtypes of IKK have been identified thus far. IKKα was initially identified as an IκB kinase induced by TNFα stimulation in HeLa cells (DiDonato et al., (1997) Nature 388, 548-554). Another IκB kinase homologous to IKKα was identified, termed IKKβ and determined to be the major IκB kinase induced following TNFα stimulation (Takeda et al., (1999) Science 284, 313-316; Hu et al., (1999) Science 284, 316-320; Li et al., (1999) Science 284, 321-325; Pot et al., (2000) U.S. Pat. No. 6,030,834; Woronicz & Goeddel (1999) U.S. Pat. No. 5,939,302). IKKα and IKKβ have an overall homology of 52% and a 65% homology in the kinase domain (Zandi et al., (1997) Cell 91, 243-252).

IκB protein kinases (IKKs) phosphorylate IκBs at specific serine residues. For example, they specifically phosphorylate serines 32 and 36 of IκBα (Traenckner et al., (1995) EMBO J. 14, 2876-2883; DiDonato et al., (1996) Mol. Cell. Biol. 16, 1295-1304). Phosphorylation of both sites is required to efficiently target IκBα for degradation. Furthermore, activation of IKKα and IKKβ is usually in response to NF-κB activating agents and mutant IKKα and IKKβ, which are catalytically inactive, can be used to block NF-κB stimulation by cytokines such as TNFα and IL-1 (Régnier et al., (1997) Cell 90, 373-383; Delhase et al., (1999) Science 284, 309-313). IκB protein kinases are therefore essential in the regulation of NF-κB activation processes.

IKKα and IKKβ have distinct structural motifs including an amino terminal serine-threonine kinase domain separated from a carboxyl proximal helix-loop-helix (H-L-H) domain by a leucine zipper domain. These structural characteristics are unlike other kinases, and the non-catalytic domains are thought to be involved in protein-protein interactions. Proteins which bind to IKKs may therefore be capable of regulating the activity of NF-κB (Marcu et al., (1999) U.S. Pat. No. 5,972,655) and potentially regulating downstream events such as induction of NF-κB. For instance, NEMO (NF-κB Essential Modulator) is a protein which has been identified to bind to IKKs and facilitate kinase activity (Yamaoke et al., (1998) Cell 93, 1231-1240; Rothwarf et al., (1998) Nature 395, 287-300; Mercurio et al., (1999) Mol. Cell. Biol. 19, 1526-1538; Haraj & Sun, (1999) J. Biol. Chem. 274, 22911-22914; Jin & Jeang, (1999) J. Biomed. Sci. 6, 115-120).

Inflammation is defined as the reaction of vascularized living tissue to injury. As such, inflammation is a fundamental, stereotyped complex of cytologic and chemical reactions of affected blood vessels and adjacent tissues in response to an injury or abnormal stimulation caused by a physical, chemical or biological agent. Inflammation usually leads to the accumulation of fluid and blood cells at the site of injury, and is usually a healing process. However, inflammation sometimes causes harm, usually through a dysfunction of the normal progress of inflammation. Inflammatory diseases are those pertaining to, characterized by, causing, resulting from, or becoming affected by inflammation. Examples of inflammatory diseases or disorders include, without limitation, asthma, lung inflammation, chronic granulomatous diseases such as tuberculosis, leprosy, sarcoidosis, and silicosis, nephritis, amyloidosis, rheumatoid arthritis, ankylosing spondylitis, chronic bronchitis, scleroderma, lupus, polymyositis, appendicitis, inflammatory bowel disease, ulcers, Sjorgen's syndrome, Reiter's syndrome, psoriasis, pelvic inflammatory disease, orbital inflammatory disease, thrombotic disease, and inappropriate allergic responses to environmental stimuli such as poison ivy, pollen, insect stings and certain foods, including atopic dermatitis and contact dermatitis.

Inflammatory diseases present a worldwide problem. Studies of disease burden have re-affirmed that tuberculosis is among the top 10 causes of death in the world. Asthma affects 5% of the adult population and 10-15% of the population of children (Armetti and Nicosia (1999) Boll Chim. Farm. 138 (11):599). Asthma is a chronic inflammatory disease that is associated with widespread but variable airflow obstruction.

Sepsis is yet another inflammation disorder and is caused by the presence of various pus-forming and other pathogenic microbes, or their toxins, in the blood or tissues of a subject. Sepsis is characterized by a systemic inflammatory response to bacterial products during infection. The symptoms of sepsis, such as fever, are caused at least in part by the inflammatory response of the body to the infecting agent.

Accordingly, there is still a great need for compounds useful for treating inflammatory disorders.

SUMMARY OF THE INVENTION

The present invention provides anti-inflammatory compounds, pharmaceutical compositions thereof, and methods of use thereof for treating inflammatory disorders. The present invention is based, at least in part, on the identification of the NEMO binding domain (NBD) on IκB kinase-α (IKKα) and on IκB kinase-β (IKKβ).

Accordingly, in one aspect, the present invention provides anti-inflammatory compounds comprising a NEMO binding domain (NBD).

In one embodiment, the present invention provides anti-inflammatory compounds comprising fusions of a NEMO binding domain and at least one membrane translocation domain. In a preferred embodiment, the membrane translocation domain facilitates membrane translocation of the anti-inflammatory compounds of the invention in vivo. The membrane translocation domain may, for example, be the third helix of the antennapedia homeodomain or the HIV-1 Tat protein. In one embodiment, the NEMO binding domain is a polypeptide having the sequence set forth in SEQ ID NO:2, 3, 4, 5, 6, 7, 8, 9, 10, 11, 12, 13, 14, 15, 16, 17, 18, or 19.

In another embodiment, the present invention provides anti-inflammatory compounds comprising: (a) peptides which include, or consist of, the amino acid sequence of SEQ ID NO:2, 3, 4, 5, 6, 7, 8, 9, 10, 11, 12, 13, 14, 15, 16, 17, 18 or 19; (b) a fragment of at least three amino acids of the amino acid sequence of SEQ ID NO:2, 3, 4, 5, 6, 7, 8, 9, 10, 11, 12, 13, 14, 15, 16, 17, 18 or 19; (c) peptides which include a conservative amino acid substitution of the amino acid sequences of SEQ ID NO:2, 3, 4, 5, 6, 7, 8, 9, 10, 11, 12, 13, 14, 15, 16, 17, 18 or 19; and (d) naturally occurring amino acid sequence variants of the amino acid sequences of SEQ ID NO:2, 3, 4, 5, 6, 7, 8, 9, 10, 11, 12, 13, 14, 15, 16, 17, 18 or 19.

In another aspect, this invention provides pharmaceutical compositions comprising the anti-inflammatory compounds of the invention, e.g., pharmaceutical compositions which include one or more pharmaceutically acceptable carriers.

In yet another aspect, the invention features a method of treating an inflammatory disorder, e.g., asthma, lung inflammation or cancer, in a subject. The method includes administering to the subject a therapeutically effective amount of one or more anti-inflammatory compounds of the invention. Without intending to be limited by mechanism, it is believed that the anti-inflammatory compounds of the invention may act (directly or indirectly) by blocking the recruitment of leukocytes into sites of acute and chronic inflammation, by down-regulating the expression of E-selectin on leukocytes, or by blocking osteoclast differentiation.

In another aspect, the present invention provides a method of inhibiting NF-κB-dependent target gene, e.g., E-selectin, expression in a cell. The method includes contacting a cell with an anti-inflammatory compound of the present invention, thereby inhibiting NF-κB-dependent target gene expression in a cell. In yet another aspect, the present invention provides methods of inhibiting NF-κB induction (e.g., IKKα and/or IKKβ dependent induction) in a cell by contacting a cell with an effective amount of an anti-inflammatory compound of the present invention, thereby inhibiting NF-κB induction in a cell. In one embodiment of this invention, such methods utilize anti-inflammatory compounds which include at least one membrane translocation domain. In still another specific embodiment of this invention, the anti-inflammatory compound s utilized in such methods include amino acid sequences comprising the sequences of SEQ ID NO:2, 4, 5, 6, 11, 12, 16, 17 or 18.

In another aspect, the present invention provides methods of identifying an anti-inflammatory compound. The methods include exposing cells which express NEMO and NF-κB to a test compound; and determining whether the test compound modulates activation of NF-κB by the cell, thereby identifying an anti-inflammatory compound.

In another aspect, the present invention provides methods of identifying an anti-inflammatory compound by exposing cells which express NEMO to a test compound; and determining whether the test compound modulates an activity of NEMO, thereby identifying an anti-inflammatory compound, e.g., a compound which modulates the activity of NEMO.

One particular advantage of the anti-inflammatory compounds of the present invention is that while blocking NF-κB induction via IKK, they do not inhibit the basal activity of NF-κB.

Other features and advantages of the invention will be apparent from the following detailed description and claims.

DETAILED DESCRIPTION OF THE INVENTION

I. General Description

Figure 1A:
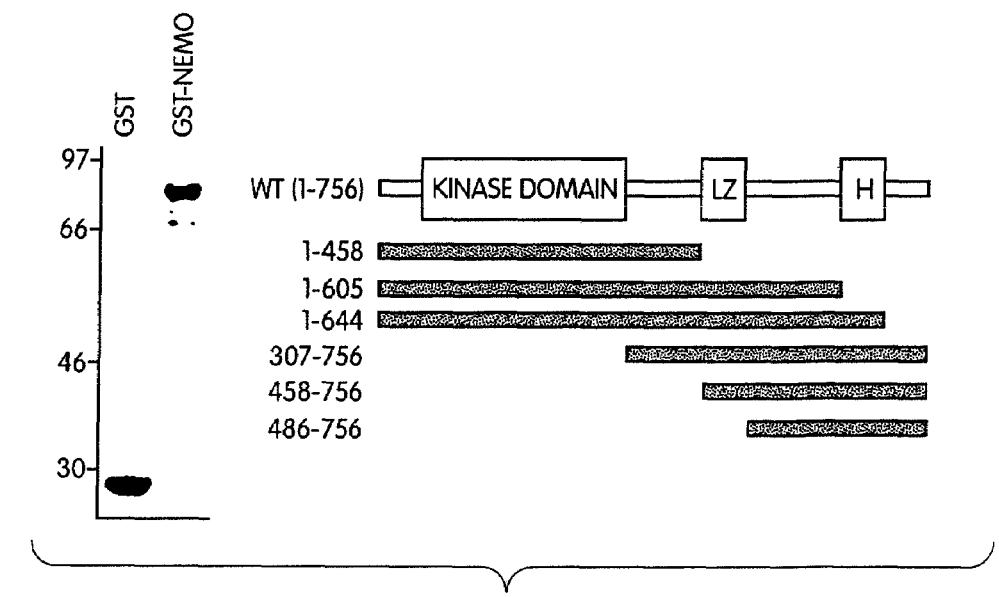
FIG. 1 depicts results from experiments indicating that NEMO interacts with the COOH-terminus of IKKβ. (A) GST alone or GST-NEMO were precipitated from bacterial lysates using glutathione-agarose, separated by SDS-PAGE (10%) and the gel was stained with Coomassie blue (left panel). Equal amounts of GST or GST-NEMO were used in subsequent GST pull-down experiments. The scheme depicted in the right panel represents the COOH- and NH2-terminal truncation mutants of IKKβ used to determine the region of NEMO interaction. (B) IKKβ mutants were cloned, expressed by in vitro translation (input; left panel) and used for GST pull-down (right panel). (C) Wild-type IKKβ and IKKβ-(644-756) were in vitro translated (left panel) and used for GST pull-down analysis (left panel). (D) HeLa cells were transiently transfected with either vector alone or increasing concentrations (0.25, 0.5, 1.0 µg/ml) of the xpress-tagged IKKβ-(644-756) construct together with the pBIIX-luciferase reporter plasmid. After forty-eight hours cells were treated with either TNFα (10 ng/ml) or IL-1β (10 ng/ml) for four hours then NF-κB activity was measured. Western blot analysis from portions of the lysate using anti-xpress (inset) demonstrates the increasing levels of expressed protein.

The present invention provides anti-inflammatory compounds, pharmaceutical compositions thereof, and methods of use thereof for treating inflammatory disorders. The present invention is based, at least in part, on the identification of the NEMO binding domain (NBD) on IκB kinase-α (IKKα) and on IκB kinase-β (IKKβ).

Without intending to be limited by mechanism, it is believed that the anti-inflammatory compounds of the present invention act by blocking the interaction of NEMO with an IKK (e.g., IKKβ or IKKα) at the NEMO binding domain (NBD), thereby inhibiting phosphorylation, degradation and subsequent dissociation of IκB from NF-κB. This inhibition results in blockade of NF-κB activation associated with pro-inflammatory responses.

The present invention also provides methods for screening and identifying anti-inflammatory compounds.

II. Definitions

Unless defined otherwise, all technical and scientific terms used herein have the same meaning as commonly understood by one of ordinary skill in the art to which this invention pertains.

As used herein, the term "binding" refers to the adherence of molecules to one another, such as, but not limited to, enzymes to substrates, antibodies to antigens, DNA strands to their complementary strands. Binding occurs because the shape and chemical nature of parts of the molecule surfaces are "complementary". A common metaphor is the "lock-and-key" used to describe how enzymes fit around their substrate.

The term "fusion peptide" or "fusion polypeptide" or "fusion protein" includes a peptide, polypeptide or protein that is obtained by combining two distinct amino acid sequences. Typically, a partial sequence from one peptide, polypeptide or protein is linked to another heterologous peptide, polypeptide or protein, using art known techniques.

A "conservative amino acid substitution" is one in which the amino acid residue is replaced with an amino acid residue having a similar side chain. Families of amino acid residues having similar side chains are known in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Non-limiting examples of conservative substitutions that can be made in the anti-inflammatory compounds of the present invention include substitution of D-phenylalanine with D-tyrosine, D-pyridylalanine or D-homophenylalanine, substitution of D-leucine with D-valine or other natural or non-natural amino acid having an aliphatic side chain and/or substitution of D-valine with D-leucine or other natural or non-natural amino acid having an aliphatic side chain.

As used herein, the term "domain" refers to a part of a molecule or structure that shares common physicochemical features, such as, but not limited to, hydrophobic, polar, globular and helical domains or properties. Specific examples of binding domains include, but are not limited to, DNA binding domains and ATP binding domains.

As used herein, the term "membrane translocation domain" refers to a peptide capable of permeating the membrane of a cell and which is used to transport attached peptides into a cell in vivo. Membrane translocation domains include, but are not limited to, the third helix of the antennapedia homeodomain protein and the HIV-1 protein Tat. Additional membrane translocation domains are known in the art and include those described in, for example, Derossi et al., (1994) *J. Biol. Chem.* 269, 10444-10450; Lindgren et al., (2000) *Trends Pharmacol. Sci.* 21, 99-103; Ho et al., *Cancer Research* 61, 474-477 (2001); U.S. Pat. Nos. 5,888,762; 6,015,787; 5,846,743; 5,747,641; 5,804,604; and Published PCT applications WO 98/52614, WO 00/29427 and WO 99/29721. The entire contents of each of the foregoing references are incorporated herein by reference.

As used herein, the term "IκB" (I kappa B) refers to any one of several members of a family of structurally related inhibitory proteins that function in the regulation of NF-κB induction.

As used herein, the term "IκB-kinase" or "IκB protein kinase" or "IκB-kinase complex" or "IκB protein kinase complex" or "IKK" refers to a kinase that phosphorylates IκBs.

As used herein, the term "IKKα" refers to the α subunit of an IκB-kinase complex. As used herein, the term "IKKβ" refers to the β subunit of an IκK-kinase complex.

As used herein, the term "NEMO" (NF-κB Essential Modulator), "IKKγ" or "IKKAP" refers to the protein which binds to IKKs and facilitates kinase activity.

As used herein, the term "NEMO Binding Domain" or "NBD" includes any domain capable of binding to NEMO at the region where NEMO usually interacts with an IKK (e.g., IKKα or IKKβ). NEMO binding domains include, for example, the α2-region (residues 737-742) of wild-type IKKβ, or the corresponding six amino acid sequence of wild-type IKKα (residues 738-743) which are critical for interaction with NEMO. The nucleic acid sequence and the corresponding amino acid sequence of the wild-type IKKβ NBD are provided in SEQ ID NO:1 (GenBank Accession No. AR067807; nucleotides 2203-2235) and SEQ ID NO:2, respectively.

The terms "analogue", "derivative" and "mimetic" as used herein are intended to include molecules which mimic the chemical structure of a peptidic structure and retain the functional properties of the peptidic structure. Approaches to designing peptide analogs, derivatives and mimetics are known in the art. For example, see Farmer, P. S. in Drug Design (E. J. Ariens, ed.) Academic Press, New York, 1980, vol. 10, pp. 119-143; Ball. J. B. and Alewood, P. F. (1990) *J. Mol. Recognition* 3:55; Morgan, B. A. and Gainor, J. A. (1989) *Ann. Rep. Med. Chem.* 24:243; and Freidinger, R. M. (1989) *Trends Pharmacol. Sci.* 10:270. See also Sawyer, T. K. (1995) "Peptidomimetic Design and Chemical Approaches to Peptide Metabolism" in Taylor, M. D. and Amidon, G. L. (eds.) *Peptide-Based Drug Design: Controlling Transport and Metabolism*, Chapter 17; Smith, A. B. 3rd, et al. (1995) *J. Am. Chem. Soc.* 117:11113-11123; Smith, A. B. 3rd, et al. (1994) *J. Am. Chem. Soc.* 116:9947-9962; and Hirschman, R., et al. (1993) *J. Am. Chem. Soc.* 115:12550-12568.

As used herein, a "derivative" of a compound X (e.g., a peptide or amino acid) refers to a form of X in which one or more reaction groups on the compound have been derivatized with a substituent group. Examples of peptide derivatives include peptides in which an amino acid side chain, the peptide backbone, or the amino- or carboxy-terminus has been derivatized (e.g., peptidic compounds with methylated amide linkages). As used herein an "analogue" of a compound X refers to a compound which retains chemical structures of X necessary for functional activity of X yet which also contains certain chemical structures which differ from X. An examples of an analogue of a naturally-occurring peptide is a peptide which includes one or more non-naturally-occurring amino acids. As used herein, a "mimetic" of a compound X refers to a compound in which chemical structures of X necessary for functional activity of X have been replaced with other chemical structures which mimic the conformation of X. Examples of peptidomimetics include peptidic compounds in which the peptide backbone is substituted with one or more benzodiazepine molecules (see e.g., James, G. L. et al. (1993) *Science* 260:1937-1942).

The term mimetic, and in particular, peptidomimetic, is intended to include isosteres. The term "isostere" as used herein is intended to include a chemical structure that can be substituted for a second chemical structure because the steric conformation of the first structure fits a binding site specific for the second structure. The term specifically includes peptide back-bone modifications (i.e., amide bond mimetics) well known to those skilled in the art. Such modifications include modifications of the amide nitrogen, the α-carbon, amide carbonyl, complete replacement of the amide bond, extensions, deletions or backbone crosslinks. Several peptide backbone modifications are known, including ψ[CH₂S], ψ[CH₂NH], ψ[CSNH₂], ψ[NHCO], ψ[COCH₂], and ψ[(E) or (Z) CH=CH]. In the nomenclature used above, ψ indicates the absence of an amide bond. The structure that replaces the amide group is specified within the brackets.

Other possible modifications include an N-alkyl (or aryl) substitution (ψ[CONR]), or backbone crosslinking to construct lactams and other cyclic structures. Other derivatives of the anti-inflammatory compounds of the invention include C-terminal hydroxymethyl derivatives, O-modified derivatives (e.g., C-terminal hydroxymethyl benzyl ether), N-terminally modified derivatives including substituted amides such as alkylamides and hydrazides and anti-inflammatory compounds in which a C-terminal phenylalanine residue is replaced with a phenethylamide analogue (e.g., Val-Phe-phenethylamide as an analogue of the tripeptide Val-Phe-Phe).

As used herein, the term "wild-type" refers to the genotype and phenotype that is characteristic of most of the members of a species occurring naturally and contrasting with the genotype and phenotype of a mutant.

III. Specific Embodiments

A. Anti-inflammatory Compounds

The present invention provides anti-inflammatory compounds comprising a NEMO binding domain (NBD). Any molecule comprising a domain that is capable of binding to NEMO at the region where NEMO usually interacts with an IKK (e.g., IKKα or IKKβ) may be used to prepare the anti-inflammatory compounds of the present invention. Examples of such molecules include peptides comprising D- and/or L-configuration amino acids; derivatives, analogues, and mimetics of peptidic compounds; antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and small organic and inorganic molecules (e.g., molecules obtained from combinatorial and natural product libraries).

In a preferred embodiment, the anti-inflammatory compounds of the invention comprise fusions of a NEMO binding domain and at least one membrane translocation domain which facilitates membrane translocation of the anti-inflammatory compounds of the invention in vivo.

Anti-inflammatory compounds of the present invention may be designed based on the wild type amino acid sequence of the NBD of IKKα or IKKβ (SEQ ID NO:2). Any fragment of the wild type amino acid sequence of the NBD of IKKα or IKKβ capable of binding NEMO may be used to prepare an anti-inflammatory compound of this invention. Point mutations, insertions, or deletions of these wild type sequences (using the methods described herein) may be used to generate additional anti-inflammatory compounds. Peptides containing conservative amino acid substitutions at positions 737, 740 and 742 of the peptide set forth in SEQ ID NO:2 are particularly useful anti-inflammatory compounds of the invention (see Table 1 for examples of conservative substitutions which have no significant effect on the ability of the peptides to bind NEMO). In addition, naturally occurring allelic variants of the IKKβ gene that retain the ability to bind NEMO may be used to prepare anti-inflammatory compounds.

In one embodiment, the anti-inflammatory compounds of the present invention comprise: (a) peptides which include, or consist of, the amino acid sequence of SEQ ID NO:2, 3, 4, 5, 6, 7, 8, 9, 10, 11, 12, 13, 14, 15, 16, 17, 18 or 19; (b) a peptide fragment of at least three amino acids of the amino acid sequence of SEQ ID NO:2, 3, 4, 5, 6, 7, 8, 9, 10, 11, 12, 13, 14, 15, 16, 17, 18 or 19; (c) peptides which include a conservative amino acid substitution of the amino acid sequences of SEQ ID NO:2, 3, 4, 5, 6, 7, 8, 9, 10, 11, 12, 13, 14, 15, 16, 17, 18 or 19; and (d) naturally occurring amino acid sequence variants of the amino acid sequences of SEQ ID NO:2, 3, 4, 5, 6, 7, 8, 9, 10, 11, 12, 13, 14, 15, 16, 17, 18 or 19.

The anti-inflammatory compounds of the present invention may also include NEMO-specific receptors, such as somatically recombined peptide receptors like specific antibodies or T-cell antigen receptors (see Harlow & Lane, (1988) Antibodies—A Laboratory Manual, Cold Spring Harbor Laboratory Press) and other natural intracellular binding agents identified with assays such as one, two and three-hybrid screens, non-natural intracellular binding agents identified in screens of chemical libraries such as described below.

The anti-inflammatory compounds of the present invention are capable of down-regulating NEMO. Down-regulation is defined herein as a decrease in activation, function or synthesis of NEMO, its ligands or activators. It is further defined to include an increase in the degradation of the NEMO gene, its protein product, ligands or activators. Down-regulation may be achieved in a number of ways, for example, by destabilizing the binding of NEMO to an IKK (e.g., IKKβ or IKKα); or by blocking the phosphorylation of IκB and causing the subsequent degradation of this protein.

Phosphorylation of IκB by IKKβ results in ubiquitination and degradation of IκB and subsequent dissociation of IκB, allowing for nuclear translocation of NF-κB, leading to up-regulation of genes critical to the inflammatory response. The anti-inflammatory compounds of the present invention may therefore be used to down-regulate NF-κB function. Down-regulation of NF-κB may also be accomplished by the use of anti-inflammatory compounds comprising polyclonal or monoclonal antibodies or fragments thereof directed against a NBD or NEMO itself. This invention further includes small molecules having the three-dimensional structure necessary to bind with sufficient affinity to a NBD or NEMO itself to, e.g., block NEMO interactions with IKKβ. IKKβ blockade resulting in decreased degradation of IκB and decreased activation of NF-κB make these small molecules useful as therapeutic agents in treating or preventing inflammation.

B. Screening Assays

In addition, this invention also provides screening methods for identifying anti-inflammatory compounds. The anti-inflammatory compounds may block the function, prevent the synthesis or reduce the biologic stability of IKKβ by interacting at the NBD of this molecule. Biologic stability is a measure of the time between the synthesis of the molecule and its degradation. For example, the stability of a protein, peptide or peptide mimetic (Kauvar, Nature Biotech. (1996) 14, 709) therapeutic may be shortened by altering its sequence to make it more susceptible to enzymatic degradation.

The present invention also includes methods of screening for compounds which deactivate, or act as antagonists of IKKβ function. Such compounds may be useful in the modulation of pathological conditions associated with alterations in IKKβ or NF-κB protein levels.

The present invention also provides methods for isolating and identifying binding partners of proteins of the invention, for example, compounds which interact with IKKβ at the NBD of this molecule, or interact with NEMO, thereby blocking NEMO interaction with IKKβ. A protein of the invention is mixed with a potential binding partner or an extract or fraction of a cell under conditions that allow for the association of potential binding partners with the proteins of the invention. After mixing, peptides, polypeptides, proteins or other molecules that have become associated with a protein of the invention are separated from the mixture. The binding partner bound to the protein of the invention can then be removed and further analyzed. To identify and isolate a binding partner, the entire protein, for instance the entire IKKβ peptide can be used. Alternatively, a fragment of the protein can be used. For example, the peptide fragment comprising NBD can be used to block interaction of IKKβ with NEMO.

A variety of methods can be used to obtain an extract of a cell. Cells can be disrupted using either physical or chemical disruption methods. Examples of physical disruption methods include, but are not limited to, sonication and mechanical shearing. Examples of chemical lysis methods include, but are not limited to, detergent lysis and enzyme lysis. A skilled artisan can readily adapt methods for preparing cellular extracts in order to obtain extracts for use in the present methods.

Once an extract of a cell is prepared, the extract is mixed with either IKKβ or NEMO under conditions in which association of the protein with the binding partner can occur. A variety of conditions can be used, the most preferred being conditions that closely resemble conditions found in the cytoplasm of a human cell. Features such as osmolarity, pH, temperature, and the concentration of cellular extract used, can be varied to optimize the association of the protein with the binding partner.

After mixing under the appropriate conditions, the bound complex is separated from the mixture. A variety of techniques can be utilized to separate the mixture. For example, antibodies specific to a protein of the invention can be used to immunoprecipitate the binding partner complex. Alternatively, standard chemical separation techniques such as chromatography and density-sediment centrifugation can be used.

After removal of non-associated cellular constituents found in the extract, the binding partner can be dissociated from the complex using conventional methods. For example, dissociation can be accomplished by altering the salt concentration or pH of the mixture.

To aid in separating associated binding partner pairs from the mixed extract, the protein can be immobilized on a solid support. For example, the protein can be attached to a nitrocellulose matrix or acrylic beads. Attachment of the protein to a solid support aids in separating peptide-binding partner pairs from other constituents found in the extract. The identified binding partners can be either a single protein or a complex made up of two or more proteins. Alternatively, binding partners may be identified using a Far-Western assay according to the procedures of Takayama et al., (1997) Methods Mol. Biol. 69, 171-184 or Sauder et al., (1996) J. Gen. Virol. 77, 991-996 or identified through the use of epitope tagged proteins or GST fusion proteins.

Alternatively, the nucleic acid molecules encoding the peptides of the invention can be used in a yeast two-hybrid system. The yeast two-hybrid system has been used to identify other protein partner pairs and can readily be adapted to employ the nucleic acid molecules herein described (see, for example, Stratagene Hybrizap® two-hybrid system).

Another embodiment of the present invention provides methods for identifying agents that modulate at least one activity of NEMO or IKKβ. Such methods or assays may utilize any means of monitoring or detecting the desired activity.

In one format, the relative amounts of a protein of the invention between a cell population that has been exposed to the agent to be tested compared to an un-exposed control cell population may be assayed. In this format, probes such as specific antibodies are used to monitor the differential expression of the protein in the different cell populations. Cell lines or populations are exposed to the agent to be tested under appropriate conditions and time. Cellular lysates may be prepared from the exposed cell line or population and a control, unexposed cell line or population. The cellular lysates are then analyzed with the probe.

Antibody probes are prepared by immunizing suitable mammalian hosts in appropriate immunization protocols using the peptides. Peptides or proteins comprising the NBD are of sufficient length, or if desired, as required to enhance immunogenicity, conjugated to suitable carriers. Methods for preparing immunogenic conjugates with carriers such as BSA, KLH, or other carrier proteins are well known in the art. In some circumstances, direct conjugation using, for example, carbodiimide reagents may be effective; in other instances linking reagents such as those supplied by Pierce Chemical Co. may be desirable to provide accessibility to the hapten. The hapten peptides can be extended at either the amino or carboxy terminus with a cysteine residue or interspersed with cysteine residues, for example, to facilitate linking to a carrier. Administration of the immunogens is conducted generally by injection over a suitable time period and with use of suitable adjuvants, as is generally understood in the art. During the immunization schedule, titers of antibodies are taken to determine adequacy of antibody formation. While the polyclonal antisera produced in this way may be satisfactory for some applications, for pharmaceutical compositions, use of monoclonal preparations is preferred. Immortalized cell lines which secrete the desired monoclonal antibodies may be prepared using the standard method of Kohler & Milstein, (1992) Biotechnology 24, 524-526 or modifications which effect immortalization of lymphocytes or spleen cells, as is generally known. The immortalized cell lines secreting the desired antibodies are screened by immunoassay in which the antigen is the peptide hapten, peptide or protein.

When the appropriate immortalized cell culture secreting the desired antibody is identified, the cells can be cultured either in vitro or by production in ascites fluid. The desired monoclonal antibodies may be recovered from the culture supernatant or from the ascites supernatant. Fragments of the monoclonals or the polyclonal antisera which contain the immunologically significant portion can be used as antagonists, as well as the intact antibodies. Use of immunologically reactive fragments, such as the Fab, Fab' of F(ab')2 fragments is often preferable, especially in a therapeutic context, as these fragments are generally less immunogenic than the whole immunoglobulin.

The antibodies or fragments may also be produced, using current technology, by recombinant means. Antibody regions that bind specifically to the desired regions of the protein can also be produced in the context of chimeras with multiple species origin. Agents that are assayed in the above method can be randomly selected or rationally selected or designed. As used herein, an agent is said to be randomly selected when the agent is chosen randomly without considering the specific sequences involved in the association of the a protein of the invention alone or with its associated substrates, binding partners, etc. An example of randomly selected agents is the use a chemical library or a peptide combinatorial library, or a growth broth of an organism.

As used herein, an agent is said to be rationally selected or designed when the agent is chosen on a non-random basis which takes into account the sequence of the target site and/or its conformation in connection with the agent's action. Agents can be rationally selected or rationally designed by utilizing the peptide sequences that comprises the NBD on IKKβ or the IKKβ binding domain on NEMO. For example, a rationally selected peptide agent can be a peptide whose amino acid sequence is identical to the amino acid sequence of SEQ ID NO: 2 or a peptide with conservative substitutions thereof.

The compounds of the present invention can be, as examples, peptides, small molecules, vitamin derivatives, as well as carbohydrates. A skilled artisan can readily recognize that there is no limit as to the structural nature of the compounds of the present invention.

The peptide compounds of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

The present invention further provides isolated nucleic acid molecules that encode the peptide having a NBD and conservative nucleotide substitutions thereof, preferably in isolated form. Conservative nucleotide substitutions include nucleotide substitutions which do not effect the coding for a particular amino acid as most amino acids have more than one codon (see King & Stansfield (Editors), A Dictionary of Genetics, Oxford University Press, 1997 at page 19). Conservative nucleotide substitutions therefore also include silent mutations and differential codon usage. For example, the invention includes the nucleic acid molecule set forth in SEQ ID NO: 1, which encodes the peptide set forth in SEQ ID NO:2, and conservative nucleotide substitutions thereof. The invention also includes nucleic acids encoding the peptides set forth in SEQ ID NO: 2, 3, 4, 5, 6, 7, 8, 9, 10, 11, 12, 13, 14, 15, 16, 17, 18 and 19 and conservative nucleotide substitutions thereof. Any nucleic acid that encodes the peptides set forth in SEQ ID NO:2, 3, 4, 5, 6, 7, 8, 9, 10, 11, 12, 13, 14, 15, 16, 17, 18 and 19 is encompassed by the invention, given the multiple permutations of nucleotide sequences possible which encode these peptides.

Specific examples of nucleic acids encompassed by this invention include, but are not limited to the following: (1) the amino acids of the peptide of SEQ ID NO:2 can be encoded by the nucleic acid sequence TTAGATTGGTCTTGGTTA (SEQ ID NO:24) or TTGGACTGGTCCTGGCTA (SEQ ID NO:25); and (2) the amino acids of the peptide of SEQ ID NO:15 can be encoded by the nucleic acid sequence TTAGATTGGTCTTATCTG (SEQ ID NO: 26) or CTTGACTGGTCATACTTA (SEQ ID NO: 27).

As used herein, a nucleic acid molecule is said to be "isolated" when the nucleic acid molecule is substantially separated from contaminant nucleic acid encoding other polypeptides from the source of nucleic acid. Modifications to the primary structure of the nucleic acid itself by deletion, addition, or alteration of the amino acids incorporated into the protein sequence during translation can be made without destroying the activity of the peptide. Such substitutions or other alterations result in peptide having an amino acid sequence encoded by a nucleic acid falling within the contemplated scope of the present invention.

Another class of compounds of the present invention are antibodies immunoreactive with critical positions of proteins of the invention. Antibody agents are obtained by immunization of suitable mammalian subjects with peptides, containing as antigenic regions, those portions of the protein intended to be targeted by the antibodies.

C. High Throughput Assays

Introduction—The power of high throughput screening is utilized to the search for new anti-inflammatory compounds which are capable of interacting with NEMO. For general information on high-throughput screening, see, for example, Cost-Effective Strategies for Automated and Accelerated High-Throughput Screening, IBCS Biomedical Library Series, IBC United States Conferences, 1996; Devlin (Editor), High Throughput Screening, Marcel Dekker 1998; U.S. Pat. No. 5,763,263. High throughput assays utilize one or more different assay techniques.

Immunodiagnostics and Immunoassays—These are a group of techniques used for the measurement of specific biochemical substances, commonly at low concentrations in complex mixtures such as biological fluids, that depend upon the specificity and high affinity shown by suitably prepared and selected antibodies for their complementary antigens. A substance to be measured must, of necessity, be antigenic—either an immunogenic macromolecule or a haptenic small molecule. To each sample a known, limited amount of specific antibody is added and the fraction of the antigen combining with it, often expressed as the bound:free ratio, is estimated, using as indicator a form of the antigen labeled with radioisotope (radioimmunoassay), fluorescent molecule (fluoroimmunoassay), stable free radical (spin immunoassay), enzyme (enzyme immunoassay), or other readily distinguishable label.

Antibodies can be labeled in various ways, including: enzyme-linked immunosorbent assay (ELISA); radioimmuno assay (RIA); fluorescent immunoassay (FIA); chemiluminescent immunoassay (CLIA); and labeling the antibody with colloidal gold particles (immunogold).

Common assay formats include the sandwhich assay, competitive or competition assay, latex agglutination assay, homogeneous assay, microtitre plate format and the microparticle-based assay.

Enzyme-linked immunosorbent assay (ELISA)—ELISA is an immunochemical technique that avoids the hazards of radiochemicals and the expense of fluorescence detection systems. Instead, the assay uses enzymes as indicators. ELISA is a form of quantitative immunoassay based on the use of antibodies (or antigens) that are linked to an insoluble carrier surface, which is then used to "capture" the relevant antigen (or antibody) in the test solution. The antigen-antibody complex is then detected by measuring the activity of an appropriate enzyme that had previously been covalently attached to the antigen (or antibody).

For information on ELISA techniques, see, for example, Crowther, ELISA: Theory and Practice (Methods in Molecular Biology, Vol. 42), Humana Press, 1995; Challacombe & Kemeny, ELISA and Other Solid Phase Immunoassays: Theoretical and Practical Aspects, John Wiley, 1998; Kemeny, A Practical Guide to ELISA, Pergamon Press, 1991; Ishikawa, Ultrasensitive and Rapid Enzyme Immunoassay (Laboratory Techniques in Biochemistry and Molecular Biology, Vol. 27), Elsevier, 1991.

Colorimetric Assays for Enzymes—Colorimetry is any method of quantitative chemical analysis in which the concentration or amount of a compound is determined by comparing the color produced by the reaction of a reagent with both standard and test amounts of the compound, often using a calorimeter. A colorimeter is a device for measuring color intensity or differences in color intensity, either visually or photoelectrically.

Standard calorimetric assays of beta-galactosidase enzymatic activity are well known to those skilled in the art (see, for example, Norton et al., (1985) Mol. Cell. Biol. 5, 281-290). A calorimetric assay can be performed on whole cell lysates using O-nitrophenyl-beta-D-galactopyranoside (ONPG, Sigma) as the substrate in a standard calorimetric beta-galactosidase assay (Sambrook et al., (1989) Molecular Cloning—A Laboratory Manual, Cold Spring Harbor Press). Automated calorimetric assays are also available for the detection of beta-galactosidase activity, as described in U.S. Pat. No. 5,733,720.

Immunofluorescence Assays—Immunofluorescence or immunofluorescence microscopy is a technique in which an antigen or antibody is made fluorescent by conjugation to a fluorescent dye and then allowed to react with the complementary antibody or antigen in a tissue section or smear. The location of the antigen or antibody can then be determined by observing the fluorescence by microscopy under ultraviolet light.

For general information on immunofluorescent techniques, see, for example, Knapp et al., (1978) Immunofluorescence and Related Staining Techniques, Elsevier; Allan, (1999) Protein Localization by Fluorescent Microscopy: A Practical Approach (The Practical Approach Series, Vol. 218) Oxford University Press; Beutner, (1983) Defined Immunofluorescence and Related Cytochemical Methods, New York Academy of Sciences; Caul, (1993) Immunofluorescence Antigen Detection Techniques in Diagnostic Microbiology, Cambridge University Press. For detailed explanations of immunofluorescent techniques applicable to the present invention, see, U.S. Pat. Nos. 5,912,176; 5,869,264; 5,866,319; and 5,861,259.

Biochips—The peptides of the invention can be used on an array or microarray for high-throughput screening for agents which interact with either the nucleic acids of the invention or their corresponding proteins.

An "array" or "microarray" generally refers to a grid system which has each position or probe cell occupied by a defined nucleic acid fragments also known as oligonucleotides. The arrays themselves are sometimes referred to as "chips" or "biochips" which are high-density nucleic acid and peptide microarrays often having thousands of probe cells in a variety of grid styles.

A typical molecular detection chip includes a substrate on which an array of recognition sites, binding sites or hybridization sites are arranged. Each site has a respective molecular receptor which binds or hybridizes with a molecule having a predetermined structure. The solid support substrates which can be used to form surface of the array or chip include organic and inorganic substrates, such as glass, polystyrenes, polyimides, silicon dioxide and silicon nitride. For direct attachment of probes to the electrodes, the electrode surface must be fabricated with materials capable of forming conjugates with the probes.

Once the array is fabricated, a sample solution is applied to the molecular detection chip and molecules in the sample bind or hybridize at one or more sites. The sites at which binding occurs are detected, and one or more molecular structures within the sample are subsequently deduced. Detection of labeled batches is a traditional detection strategy and includes radioisotope, fluorescent and biotin labels, but other options are available, including electronic signal transduction.

The methods of this invention will find particular use wherever high through-put of samples is required. In particular, this invention is useful in ligand screening settings and for determining the composition of complex mixtures.

Polypeptides are an exemplary system for exploring the relationship between structure and function in biology. When the twenty naturally occurring amino acids are condensed into a polymeric molecule they form a wide variety of three-dimensional configurations, each resulting from a particular amino acid sequence and solvent condition. For example, the number of possible polypeptide configurations using the twenty naturally occurring amino acids for a polymer five amino acids long is over three million. Typical proteins are more than one-hundred amino acids in length.

In typical applications, a complex solution containing one or more substances to be characterized contacts a polymer array comprising polypeptides. The polypeptides of the invention can be prepared by classical methods known in the art, for example, by using standard solid phase techniques. The standard methods include exclusive solid phase synthesis, partial solid phase synthesis methods, fragment condensation, classical solution synthesis and recombinant DNA technology (see Merrifield, (1963) Am. Chem. Soc. 85, 2149-2152).

In a preferred embodiment, the polypeptides or proteins of the array can bind to other co-receptors to form a heteroduplex on the array. In yet another embodiment, the polypeptides or proteins of the array can bind to peptides or small molecules.

D. Uses for the Anti-Inflammatory Compounds of the Present Invention

The anti-inflammatory compounds of the present invention (e.g., compounds that modulate the expression of NEMO or compounds such as agonists or antagonists of at least one activity of NEMO) may be used to modulate inflammation and treat or diagnose an inflammatory disorder in a subject. The methods include administering to a subject an anti-inflammatory compound of the invention in an amount effective to treat an inflammatory disorder.

As used herein, an "inflammatory disorder" is intended to include a disease or disorder characterized by, caused by, resulting from, or becoming affected by inflammation. An inflammatory disorder may be caused by or be associated with biological and pathological processes associated with NEMO or IKKβ function and activity and/or with NF-κB mediated processes. Examples of inflammatory diseases or disorders include, but not limited to, acute and chronic inflammation disorders such as asthma, psoriasis, rheumatoid arthritis, osteoarthritis, psoriatic arthritis, inflammatory bowel disease (Crohn's disease, ulcerative colitis), sepsis, vasculitis, and bursitis; autoimmune diseases such as Lupus, Polymyalgia, Rheumatica, Scleroderma, Wegener's granulomatosis, temporal arteritis, cryoglobulinemia, and multiple sclerosis; transplant rejection; osteoporosis; cancer, including solid tumors (e.g., lung, CNS, colon, kidney, and pancreas); Alzheimer's disease; atherosclerosis; viral (e.g., HIV or influenza) infections; chronic viral (e.g., Epstein-Barr, cytomegalovirus, herpes simplex virus) infection; and ataxia telangiectasia.

Pathological processes refer to a category of biological processes which produce a deleterious effect. For example, unregulated expression of NF-κB is associated with pro-inflammatory processes underlying certain pathological processes. As used herein, an anti-inflammatory compound is said to modulate a pathological process when the compound reduces the degree or severity of the process. For instance, pro-inflammatory responses may be prevented or pathological processes modulated by the administration of anti-inflammatory compounds which reduce, promote or modulate in some way the expression or at least one activity of NEMO or IKKβ.

The anti-inflammatory compounds of the present invention may, therefore, be used to treat diseases with an NF-κB inflammatory component. Such diseases include, but are not limited to, osteoporosis, rheumatoid arthritis, atherosclerosis, asthma (Ray & Cohn, (1999) J. Clin. Invest. 104, 985-993; Christman et al., (2000) Chest 117, 1482-1487) and Alzheimer's disease. For a review of diseases with an NF-κB inflammatory component, see Epstein, (1997) New Eng. J. Med. 336, 1066-1071; Lee et al., (1998) J. Clin. Pharmacol. 38, 981-993; Brand et al., (1997) Exp. Physiol. 82, 297-304.

Pathological processes associated with a pro-inflammatory response in which the anti-inflammatory compounds of the invention would be useful for treatment include, but are not limited to, asthma, allergies such as allergic rhinitis, uticaria, anaphylaxis, drug sensitivity, food sensitivity and the like; cutaneous inflammation such as dermatitis, eczema, psorisis, contact dermatitis, sunburn, aging, and the like; arthritis such as osteoarthritis, psoriatic arthritis, lupus, spondylarthritis and the like. Anti-inflammatory compounds are also useful for treating chronic obstruction pulmonary disease and chronic inflammatory bowel disease. The anti-inflammatory compounds of the present invention may further be used to replace corticosteroids in any application in which corticosteroids are used including immunosuppression in transplants and cancer therapy.

As used herein, the term "subject" includes warm-blooded animals, preferably mammals, including humans. In a preferred embodiment, the subject is a primate. In an even more preferred embodiment, the primate is a human.

As used herein, the term "administering" to a subject includes dispensing, delivering or applying an anti-inflammatory compound, e.g., an anti-inflammatory compound in a pharmaceutical formulation (as described herein), to a subject by any suitable route for delivery of the compound to the desired location in the subject, including delivery by either the parenteral or oral route, intramuscular injection, subcutaneous/intradermal injection, intravenous injection, buccal administration, transdermal delivery and administration by the rectal, colonic, vaginal, intranasal or respiratory tract route (e.g., by inhalation).

As used herein, the term "effective amount" includes an amount effective, at dosages and for periods of time necessary, to achieve the desired result, e.g., sufficient to treat an inflammatory disorder in a subject. An effective amount of an anti-inflammatory compound of the invention, as defined herein may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the compound are outweighed by the therapeutically beneficial effects.

A therapeutically effective amount of an anti-inflammatory compound of the invention (i.e., an effective dosage) may range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an anti-inflammatory compound of the invention can include a single treatment or, preferably, can include a series of treatments. In one example, a subject is treated with an anti-inflammatory compound of the invention in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of an anti-inflammatory compound of the invention used for treatment may increase or decrease over the course of a particular treatment.

The anti-inflammatory compounds of the present invention can be provided alone, or in combination with other agents that modulate a particular pathological process. For example, an anti-inflammatory compound of the present invention can be administered in combination with other known anti-inflammatory agents. Known anti-inflammatory agents that may be used in the methods of the invention can be found in Harrison's Principles of Internal Medicine, Thirteenth Edition, Eds. T. R. Harrison et al. McGraw-Hill N.Y., N.Y.; and the Physicians Desk Reference 50th Edition 1997, Oradell New Jersey, Medical Economics Co., the complete contents of which are expressly incorporated herein by reference. The anti-inflammatory compounds of the invention and the additional anti-inflammatory agents may be administered to the subject in the same pharmaceutical composition or in different pharmaceutical compositions (at the same time or at different times).

The present invention further provides methods for modulating signal transduction involving IκB in a cell. The methods include modulating IKKβ activity, e.g. by contacting a cell with an anti-inflammatory compound. The anti-inflammatory compound may, for example, inhibit the interaction of NEMO with IKKβ at the NBD, thereby inhibiting IKKβ function. The cell may reside in culture or in situ, i.e., within the natural host.

For diagnostic uses, the anti-inflammatory compounds of the invention may be labeled, such as with fluorescent, radioactive, chemiluminescent, or other easily detectable molecules. The label may be conjugated either directly or indirectly to the anti-inflammatory compound.

E. Pharmaceutical Preparations

The invention also includes pharmaceutical compositions comprising the anti-inflammatory compounds of the invention together with a pharmaceutically acceptable carrier. Pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical carriers are described in Gennaro et al., (1995) Remington's Pharmaceutical Sciences, Mack Publishing Company. In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil or synthetic fatty acid esters, for example, ethyl oleate or triglycerides. Aqueous injection suspensions may contain substances which increase the viscosity of the suspension include, for example, sodium carboxymethyl cellulose, sorbitol, and dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulations may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

The anti-inflammatory compounds of the invention can also be incorporated into pharmaceutical compositions which allow for the sustained delivery of the anti-inflammatory compounds to a subject for a period of at least several weeks to a month or more. Such formulations are described in U.S. Pat. Nos. 5,968,895 and 6,180,608 B1, the contents of each of which are incorporated herein by reference.

The anti-inflammatory compounds of the present invention may be administered via parenteral, subcutaneous, intravenous, intramuscular, intraperitoneal, transdermal or buccal routes. Alternatively, or concurrently, administration may be by the oral route or by inhalation or lavage, directly to the lungs. The dosage administered will be dependent upon the age, health, and weight of the recipient, kind of concurrent treatment, if any, frequency of treatment, and the nature of the effect desired.

The anti-inflammatory compounds used in the methods of treatment described herein may be administered systemically or topically, depending on such considerations as the condition to be treated, need for site-specific treatment, quantity of drug to be administered and similar considerations.

Topical administration may be used. Any common topical formation such as a solution, suspension, gel, ointment or salve and the like may be employed. Preparation of such topical formulations are well described in the art of pharmaceutical formulations as exemplified, for example, by Remington's Pharmaceutical Sciences. For topical application, these compounds could also be administered as a powder or spray, particularly in aerosol form. The active ingredient may be administered in pharmaceutical compositions adapted for systemic administration. As is known, if a drug is to be administered systemically, it may be confected as a powder, pill, tablet or the like or as a syrup or elixir for oral administration. For intravenous, intraperitoneal or intra-lesional administration, the compound will be prepared as a solution or suspension capable of being administered by injection. In certain cases, it may be useful to formulate these compounds in suppository form or as an extended release formulation for deposit under the skin or intramuscular injection. In a preferred embodiment, the anti-inflammatory compounds of the invention may be administered by inhalation. For inhalation therapy the compound may be in a solution useful for administration by metered dose inhalers or in a form suitable for a dry powder inhaler.

An effective amount is that amount which will modulate the activity or alter the level of a target protein. A given effective amount will vary from condition to condition and in certain instances may vary with the severity of the condition being treated and the patient's susceptibility to treatment. Accordingly, a given effective amount will be best determined at the time and place through routine experimentation. However, it is anticipated that in the treatment of a tumor in accordance with the present invention, a formulation containing between 0.001 and 5 percent by weight, preferably about 0.01 to 1 percent, will usually constitute a therapeutically effective amount. When administered systemically, an amount between 0.01 and 100 mg per kg body weight per day, but preferably about 0.1 to 10 mg per kg, will effect a therapeutic result in most instances.

In practicing the methods of this invention, the compounds of this invention may be used alone or in combination, or in combination with other therapeutic or diagnostic agents. In certain preferred embodiments, the compounds of this invention may be coadministered along with other compounds typically prescribed for these conditions according to generally accepted medical practice. The compounds of this invention can be utilized in vivo, ordinarily in mammals, preferably in humans.

In still another embodiment, the anti-inflammatory compounds of the invention may be coupled to chemical moieties, including proteins that alter the functions or regulation of target proteins for therapeutic benefit. These proteins may include in combination other inhibitors of cytokines and growth factors that may offer additional therapeutic benefit in the treatment of inflammary disorders. In addition, the anti-inflammatory compounds of the invention may also be conjugated through phosphorylation to biotinylate, thioate, acetylate, iodinate using any of the cross-linking reagents well known in the art.

F. Molecular Biology, Microbiology and Recombinant DNA Techniques

In accordance with the present invention, as described above or as discussed in the Examples below, there may be employed conventional molecular biology, microbiology and recombinant DNA techniques. Such techniques are explained fully in the literature. See for example, Sambrook et al., (1989) Molecular Cloning—A Laboratory Manual, Cold Spring Harbor Press; Glover, (1985) DNA Cloning: A Practical Approach; Gait, (1984) Oligonucleotide Synthesis; Harlow & Lane, (1988) Antibodies—A Laboratory Manual, Cold Spring Harbor Press; Roe et al., (1996) DNA Isolation and Sequencing: Essential Techniques, John Wiley; and Ausubel et. al., (1995) Current Protocols in Molecular Biology, Greene Publishing.

G. Antisense RNA

Antisense molecules are RNA or single-stranded DNA molecules with nucleotide sequences complementary to a specified mRNA. When a laboratory-prepared antisense molecule is injected into cells containing the normal mRNA transcribed by a gene under study, the antisense molecule can base-pair with the mRNA, preventing translation of the mRNA into protein. The resulting double-stranded RNA or RNA/DNA is digested by enzymes that specifically attach to such molecules. Therefore, a depletion of the mRNA occurs, blocking the translation of the gene product so that antisense molecules find uses in medicine to block the production of deleterious proteins. Methods of producing and utilizing antisense RNA are well known to those of ordinary skill in the art (see, for example, Lichtenstein & Nellen (Editors), Antisense Technology: A Practical Approach, Oxford University Press, 1997; Agrawal & Crooke, Antisense Research and Application (Handbook of Experimental Pharmacology, Vol. 131), Springer Verlag, 1998; Gibson, Antisense and Ribozyme Methodology: Laboratory Companion, Chapman & Hall, 1997; Mol & Van Der Krol, Antisense Nucleic Acids and Proteins, Marcel Dekker; Weiss, Antisense Oligodeoxynucleotides and Antisense RNA: Novel Pharmacological and Therapeutic Agents, CRC Press, 1997; Stanley et al., (1993) Antisense Research and Applications, CRC Press; Stein & Krieg, (1998) Applied Antisense Oligonucleotide Technology).

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues. RNA molecules may be modified to increase intracellular stability and half-life. Possible modifications include, but are not limited to, the addition of flanking sequences at the 5' and/or 3' ends of the molecule or the use of phosphorothioate or 2'O-methyl rather than phosphodiesterase linkages within the backbone of the molecule. This concept can be extended by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

H. Fusion Proteins

A fusion protein is an expression product resulting from the fusion of two genes. Such a protein may be produced, e.g., in recombinant DNA expression studies or, naturally, in certain viral oncogenes in which the oncogene is fused to gag.

The production of a fusion protein sometimes results from the need to place a cloned eukaryotic gene under the control of a bacterial promoter for expression in a bacterial system. Sequences of the bacterial system are then frequently expressed linked to the eukaryotic protein. Fusion proteins are used for the analysis of structure, purification, function, and expression of heterologous gene products.

A fused protein is a hybrid protein molecule which can be produced when a nucleic acid of interest is inserted by recombinant DNA techniques into a recipient plasmid and displaces the stop codon for a plasmid gene. The fused protein begins at the amino end with a portion of the plasmid protein sequence and ends with the protein of interest.

The production of fusion proteins is well known to one skilled in the art (See, e.g., U.S. Pat. Nos. 5,908,756; 5,907,085; 5,906,819; 5,905,146; 5,895,813; 5,891,643; 5,891,628; 5,891,432; 5,889,169; 5,889,150; 5,888,981; 5,888,773; 5,886,150; 5,886,149; 5,885,833; 5,885,803; 5,885,779; 5,885,580; 5,883,124; 5,882,941; 5,882,894; 5,882,864; 5,879,917; 5,879,893; 5,876,972; 5,874,304; and 5,874,290). For a general review of the construction, properties, applications and problems associated with specific types of fusion molecules used in clinical and research medicine, see, e.g., Chamow et al., (1999) Antibody Fusion Proteins, John Wiley.

I. Peptide Mimetics

This invention also includes peptide mimetics, e.g., peptide mimetics which mimic the three-dimensional structure of the NBD on IKKβ and block NEMO binding at the NBD by binding to NEMO. Such peptide mimetics may have significant advantages over naturally-occurring peptides, including, for example, more economical production, greater chemical stability, enhanced pharmacological properties (half-life, absorption, potency, and efficacy), altered specificity (e.g., a broad-spectrum of biological activities), reduced antigenicity, and others.

In one form, mimetics are peptide-containing molecules that mimic elements of protein secondary structure. See, for example, Johnson et al., (1993) Peptide Turn Mimetics in Biotechnology and Pharmacy, Pezzuto et al., (Editors) Chapman & Hall. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. In another form, peptide analogs are commonly used in the pharmaceutical industry as non-peptide drugs with properties analogous to those of the template peptide. These types of non-peptide compounds are also referred to as "peptide mimetics" or "peptidomimetics" (Fauchere, (1986) Adv. Drug Res. 15, 29-69; Veber & Freidinger, (1985) Trends Neurosci. 8, 392-396; and Evans et al., (1987) J. Med. Chem. 30, 1229-1239, which are incorporated herein by reference) and are usually developed with the aid of computerized molecular modeling.

Peptide mimetics that are structurally similar to therapeutically useful peptides may be used to produce an equivalent therapeutic or prophylactic effect. Generally, peptide mimetics are structurally similar to a paradigm polypeptide (i.e., a polypeptide that has a biochemical property or pharmacological activity), such as the NBD, but have one or more peptide linkages optionally replaced by a linkage selected from the group consisting of: —$CH_2NH$—, —$CH_2S$—, —$CH_2CH_2$—, —$CH=CH$— (cis and trans), —$COCH_2$—, —$CH(OH)CH_2$—, and —$CH_2SO$—, by methods known in the art and further described in the following references: Weinstein, (1983) Chemistry and Biochemistry of Amino Acids, Peptides and Proteins, Marcel Dekker; Morley, (1980) Trends Pharmacol. Sci. 1, 463-468 (general review); Hudson et al., (1979) Int. J. Pept. Protein Res. 14, 177-185 (—$CH_2NH$—, $CH_2CH_2$—); Spatola et al., (1986) Life Sci. 38, 1243-1249 (—$CH_2$—S); Hann, (1982) J. Chem. Soc. Perkin Trans. 1, 307-314 (—CH—CH—, cis and trans); Almquist et al., (1980) J. Med. Chem. 23, 1392-1398 (—$COCH_2$—); Jennings-White et al., (1982) Tetrahedron Lett. 23, 2533 (—$COCH_2$—); U.S. Pat. No. 4,424,207 (—$CH(OH)CH_2$—); Holladay et al., (1983) Tetrahedron Lett. 24, 4401-4404 (—$C(OH)CH_2$—); and Hruby, (1982) Life Sci. 31, 189-199 (—$CH2-S$—); each of which is incorporated herein by reference.

Labeling of peptide mimetics usually involves covalent attachment of one or more labels, directly or through a spacer (e.g., an amide group), to non-interfering position(s) on the peptide mimetic that are predicted by quantitative structure-activity data and/or molecular modeling. Such non-interfering positions generally are positions that do not form direct contacts with the macromolecules(s) (e.g., are not contact points in NκD-NEMO complexes) to which the peptide mimetic binds to produce the therapeutic effect. Derivitization (e.g., labeling) of peptide mimetics should not substantially interfere with the desired biological or pharmacological activity of the peptide mimetic. NBD peptide mimetics can be constructed by structure-based drug design through replacement of amino acids by organic moieties (see, for example, Hughes, (1980) Philos. Trans. R. Soc. Lond. 290, 387-394; Hodgson, (1991) Biotechnol. 9, 19-21; Suckling, (1991) Sci. Prog. 75, 323-359).

The use of peptide mimetics can be enhanced through the use of combinatorial chemistry to create drug libraries. The design of peptide mimetics can be aided by identifying amino acid mutations that increase or decrease binding of a NBD (e.g., the NBD on IKKβ) to NEMO. For example, such mutations as identified in Table 1. Approaches that can be used include the yeast two hybrid method (see Chien et al., (1991) Proc. Natl. Acad. Sci. USA 88, 9578-9582) and using the phage display method. The two hybrid method detects protein-protein interactions in yeast (Fields et al., (1989) Nature 340, 245-246). The phage display method detects the interaction between an immobilized protein and a protein that is expressed on the surface of phages such as lambda and M13 (Amberg et al., (1993) Strategies 6, 2-4; Hogrefe et al., (1993) Gene 128, 119-126). These methods allow positive and negative selection for protein-protein interactions and the identification of the sequences that determine these interactions.

For general information on peptide synthesis and peptide mimetics, see, for example, Jones, (1992) Amino Acid and Peptide Synthesis, Oxford University Press; Jung, (1997) Combinatorial Peptide and Nonpeptide Libraries: A Handbook, John Wiley; and Bodanszky et al., (1993) Peptide Chemistry: A Practical Textbook, 2nd Revised Edition, Springer Verlag each of which is hereby incorporated in its entirety.

J. Transgenic Animals

Transgenic animals are genetically modified animals into which recombinant, exogenous or cloned genetic material has been experimentally transferred. Such genetic material is often referred to as a transgene. The nucleic acid sequence of the transgene may be integrated either at a locus of a genome where that particular nucleic acid sequence is not otherwise normally found or at the normal locus for the transgene. The transgene may consist of nucleic acid sequences derived from the genome of the same species or of a different species than the species of the target animal.

The term "germ cell line transgenic animal" refers to a transgenic animal in which the genetic alteration or genetic information was introduced into a germ line cell, thereby conferring the ability of the transgenic animal to transfer the genetic information to offspring. If such offspring in fact possess some or all of that alteration or genetic information, then they too are transgenic animals.

The alteration or genetic information may be foreign to the species of animal to which the recipient belongs, foreign only to the particular individual recipient, or may be genetic information already possessed by the recipient. In the last case, the altered or introduced gene may be expressed differently than the native gene.

Transgenic animals can be produced by a variety of different methods including transfection, electroporation, microinjection, gene targeting in embryonic stem cells and recombinant viral and retroviral infection (see, e.g., U.S. Pat. Nos. 4,736,866; 5,602,307; Mullins et al., (1993) Hypertension 22, 630-633; Brenin et al., (1997) Surg. Oncol. 6, 99-110; Tuan, (1997) Recombinant Gene Expression Protocols, Methods in Molecular Biology No. 62, Humana Press).

A number of recombinant or transgenic mice have been produced, including those which express an activated oncogene sequence (U.S. Pat. No. 4,736,866); express simian SV40 T-antigen (U.S. Pat. No. 5,728,915); lack the expression of interferon regulatory factor 1 (IRF-1) (U.S. Pat. No. 5,731,490); exhibit dopaminergic dysfunction (U.S. Pat. No. 5,723,719); express at least one human gene which participates in blood pressure control (U.S. Pat. No. 5,731,489); display greater similarity to the conditions existing in naturally occurring Alzheimer's disease (U.S. Pat. No. 5,720,936); have a reduced capacity to mediate cellular adhesion (U.S. Pat. No. 5,602,307); possess a bovine growth hormone gene (Clutter et al., (1996) Genetics 143, 1753-1760) or, are capable of generating a fully human antibody response (Zou et al., (1993) Science 262, 1271-1274).

While mice and rats remain the animals of choice for most transgenic experimentation, in some instances it is preferable or even necessary to use alternative animal species. Transgenic procedures have been successfully utilized in a variety of non-murine animals, including sheep, goats, pigs, dogs, cats, monkeys, chimpanzees, hamsters, rabbits, cows and guinea pigs (see Kim et al., (1997) Mol. Reprod. Dev. 46, 515-526; Houdebine, (1995) Reprod. Nutr. Dev. 35, 609-617; Petters, (1994) Reprod. Fertil. Dev. 6, 643-645; Schnieke et al., (1997) Science 278, 2130-2133; Amoah, (1997) J. Animal Science 75, 578-585).

The method of introduction of nucleic acid fragments into recombination competent mammalian cells can be by any method which favors co-transformation of multiple nucleic acid molecules. Detailed procedures for producing transgenic animals are readily available to one skilled in the art, including the disclosures in U.S. Pat. Nos. 5,489,743 and 5,602,307.

The present invention comprises transgenic animals expressing a gene encoding a NBD, and mutations of that gene resulting in conservative and non-conservative amino acid substitutions when compared to the wild type gene.

This invention is further illustrated by the following examples which should not be construed as limiting. The contents of all references, patents and published patent applications cited throughout this application, as well as the Figures and the Sequence Listing, are hereby incorporated by reference.

EXAMPLES

Example 1

Identification of NEMO Binding Domain on IKKB

To identify the NEMO-interacting domain of IKKβ we performed in vitro pull down assays (Zhong et al., (1997) Cell 89, 413-424) using a bacterially expressed version of full length NEMO fused at its NH2-terminus to glutathione S-transferase (GST-NEMO; FIG. 1A). Various truncation mutants lacking different functional domains of IKKβ (catalytic domain, leucine zipper and helix-loop-helix; FIG. 1A) were constructed.

All sub-cloning and mutagenesis of full length cDNA clones of IKKα and IKKβ was performed by PCR using cloned Pfu DNA-polymerase (Stratagene). The wild-type and mutated IKKβ cDNA were inserted into the KpnI and NotI restriction sites of pcDNA-3 or pcDNA-3.1-xpress (Invitrogen) and all IKKα cDNAs were inserted into the EcoRI and XhoI sites of the same vectors. FLAG-tagged versions of both kinases were constructed by subcloning into pFLAG-CMV-2 (Sigma). For GST-IKKβ-(644-756), the PCR fragment was inserted into the EcoRI and XhoI sites of pGEX-4T1 (Pharmacia). Full length cDNA encoding human NEMO was obtained by reverse transcriptase (RT)-PCR from HeLa cell mRNA using the Expand™ Long Template PCR System (Boehringer Mannheim) and the primer pair (5'-ATAGAC-GAATTCAATAGGCACCTCTGGAAG) (SEQ ID NO: 20) and (3'-TAGGACCTCGAGCTACTCAATGCACTCCATG) (SEQ ID NO: 21). The resulting PCR fragment was inserted into the EcoRI and XhoI sites of pcDNA-3 or pcDNA-s.1-xpress. All subsequent NEMO mutants were constructed by PCR using Pfu DNA-polymerase. GST-NEMO was constructed by sub-cloning the full-length cDNA into the EcoRI and XhoI sites of pGEX-4T1.

Figure 1B:
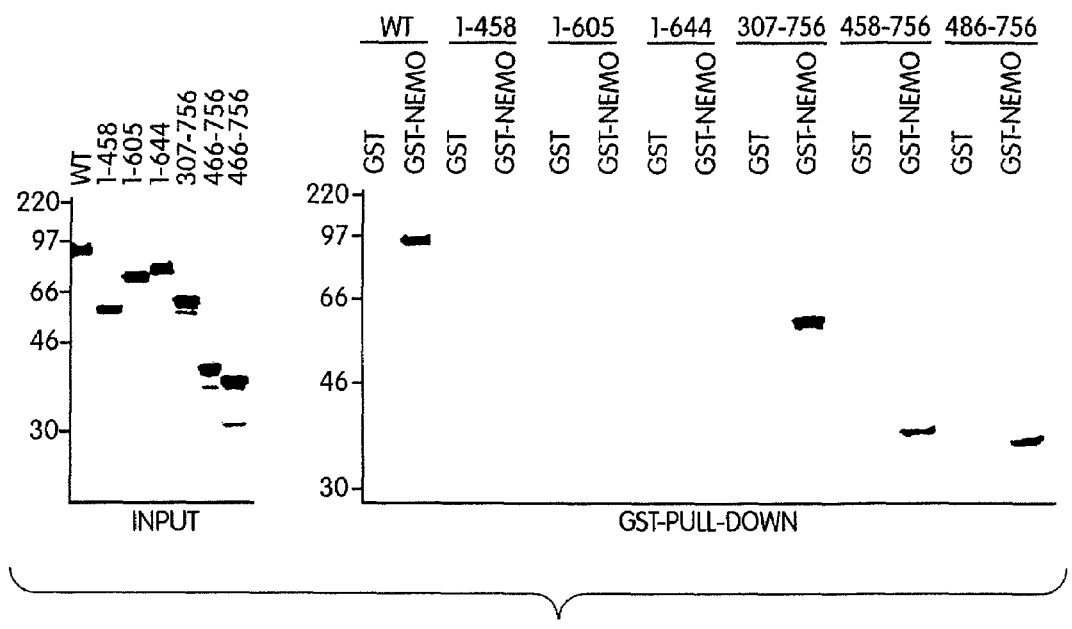
Figure 1C:
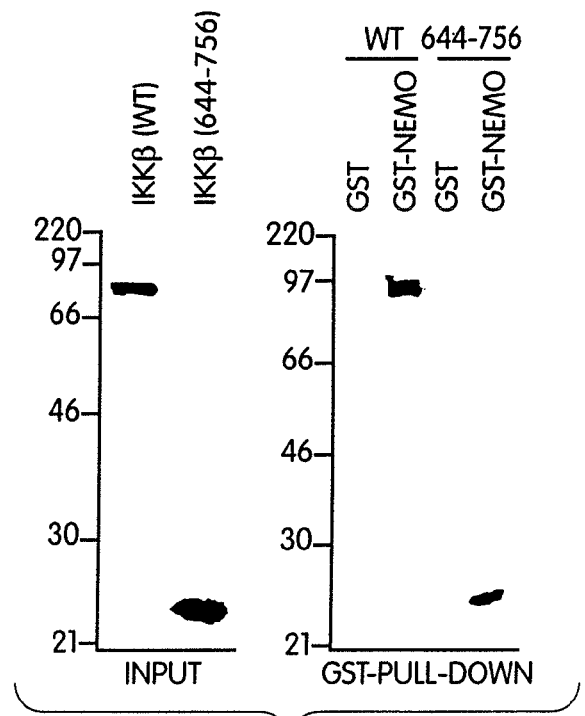

These mutants were labeled by in vitro translation with [$^{35}$S]-methionine (input; FIG. 1B), mixed with either GST alone or GST-NEMO, and precipitated using glutathione-agarose. None of the mutants interacted with GST alone, whereas wild-type and all three NH2-terminal truncations of IKKβ (307-756, 458-756 and 486-756) interacted with GST-NEMO (FIG. 1B (right panel). In contrast, none of the COOH-terminal truncation mutants (1-456, 1-605 or 1-644) precipitated with GST-NEMO. These results demonstrate that NEMO interacts with a region in the COOH-terminus of IKKβ distal to the helix-loop-helix (HLH) domain. A mutant consisting of only the region from amino acid 644 (immediately after the HLH) to the COOH-terminus (residue 756) of IKKβ was constructed next. As shown in FIG. 1C, this mutant did not precipitate with GST but did interact with GST-NEMO confirming that this region mediates the interaction between these two molecules.

The effects of IKKβ-(644-756) on IL-1β- and TNFα-induced NF-κB activation by transiently transfecting HeLa cells with the mutant together with an NF-κB-dependent reporter plasmid (pBIIX-luciferase) was tested next (Kopp & Ghosh, (1994) Science 265, 956-959). For transfection studies, HeLa and COS cells were seeded into either twenty-four well (1×10$^5$ cells/well) or six well (5×10$^5$ cells/well) plates and grown for twenty-four hours before transfection of DNA with Fugene6 (Roche) according to the manufacturer's protocol. Cells in twenty-four well and six well trays received a total of 1 pg or 2 μg of DNA respectively. After forty-eight hours cells were lysed with TNT (200 mM NaCl, 20 mM Tris-pH 8.0, 1% Triton-100) and the lysate were used for either immunoprecipitation or luciferase assay (Primage Luciferase Assay System).

Figure 1D:
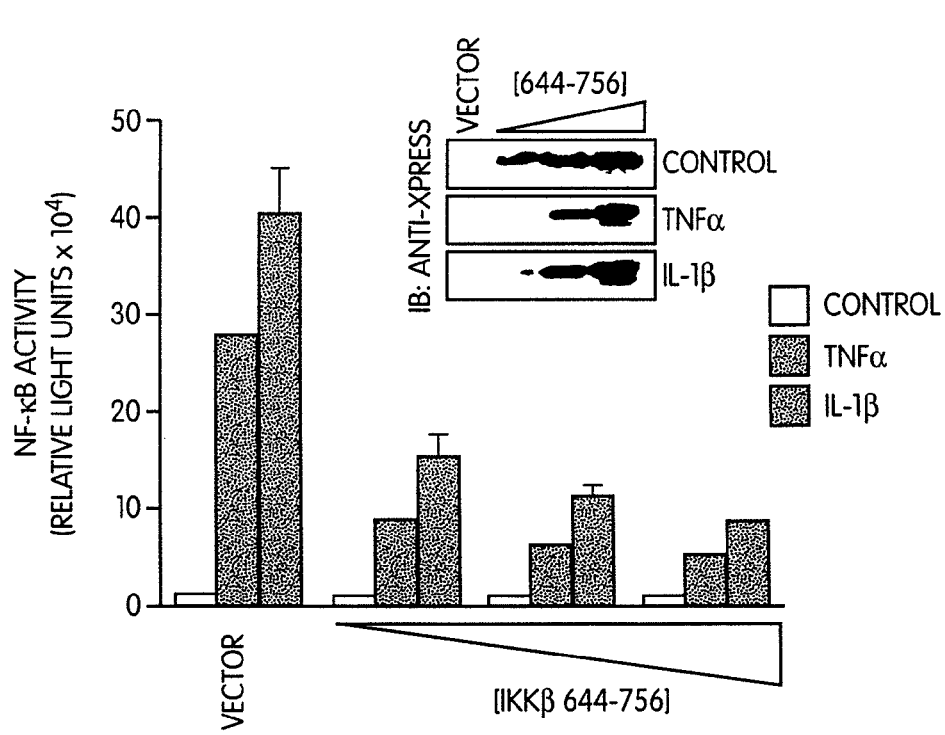
Figure 2A:
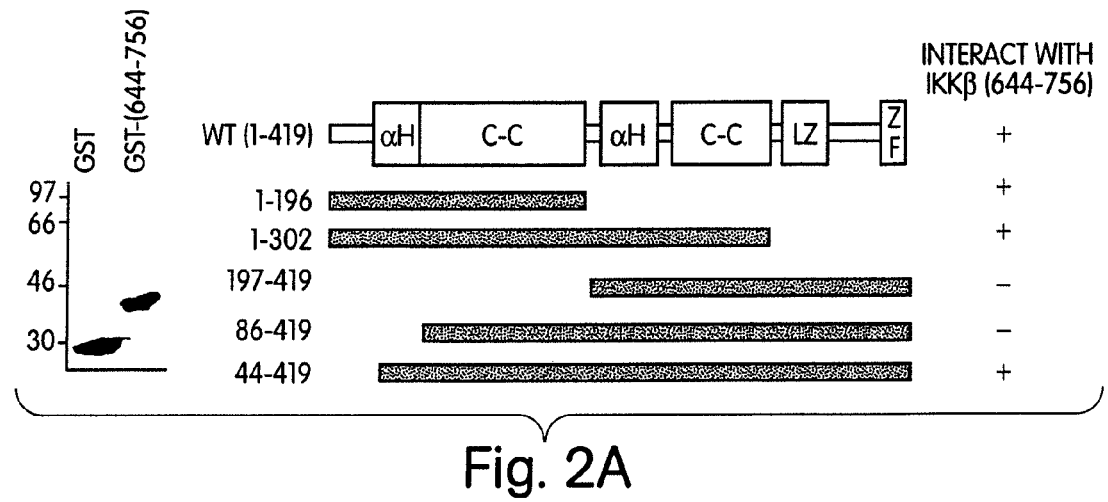
FIG. 2 depicts results from experiments indicating that the first α-helical region of NEMO is required for binding to IKKβ. (A) A truncated version of IKKβ consisting of only the COOH-terminus from residue V644 to S756 was fused with GST (GST-644-756) and expressed in bacteria. After precipitation by glutathione agarose, GST alone and GST-(644-756) were separated by SDS-PAGE (10%) and the gel was stained with Coomassie blue (left panel). Equal amounts of each protein were used for subsequent GST pull-down analyses. Various NH2- and COOH-terminal truncations of NEMO were constructed, [$^{35}$S]-methionine labeled and used for in vitro pull down (right panel). Mutants that interacted with GST-(644-756) are indicated (+). None of the mutants interacted with GST alone. (B) Wild-type NEMO and a deletion mutant lacking the first α-helical region (del.α.H) were in vitro translated (left panel: input) and used for GST pull-down using the proteins shown above (A: left). (C) HeLa cells were transfected with pBIIx-luciferase together with either pcDNA-3 (vector) or increasing concentrations of del.αH (0.25, 0.5, 1.0 µg/ml) for forty-eight hours then treated for four hours with TNFα (10 ng/ml). Cells were then lysed and NF-κB activity was measured by luciferase assay.

FIG. 1D shows that IKKβ-(644-756) inhibited NF-κB activation induced by these cytokines in a dose-dependent manner. These results indicate that IKKβ-(644-756) acts as a dominant-negative by titrating endogenous NEMO out of the core IκB-kinase complex. Without the recruitment of regulatory proteins by NEMO, IKKβ becomes refractory to IL-1β- and TNFα-induced signals that should otherwise cause its activation. Structurally, NEMO consists of extensive α-helical regions containing two prominent stretches of coiled-coil and a leucine-zipper motif, and a COOH-terminal zinc-finger domain (FIG. 2A) (Mercurio et al., (1999) Mol. Cell. Biol. 19, 1526-1538; Yamaoka et al., (1998) Cell 93, 1231-1240; Rothwarf et al., (1998) Nature 395, 297-300). Previous studies attempting to identify the region of NEMO required for its interaction with IKKβ have generated conflicting results (Harhaj et al., (1999) J. Biol. Chem. 274, 15297-15300). To address this question GST-pull-down assays using a GST-fusion protein of IKKβ-(644-756) (FIG. 2A) and various [$^{35}$S]-methionine-labeled truncation mutants of NEMO (FIG. 2A) were performed. FIG. 2A (right panel) summarizes the results of these experiments in which it was demonstrated that IKKβ-(644-756) interacted with NEMO-(1-196), -(1-302) and -(44-419) but not NEMO-(197-419) or -(86-419). Identical results were obtained from immuno-precipitation studies using lysate of COS or HEK293 cells transiently transfected with FLAG-tagged IKKβ and the NEMO mutants (data not shown).

For all immunoprecipitations HeLa or COS cells grown in six well trays were lysed in 500 μl TNT. FLAG-tagged proteins were precipitated from lysate of transfected cells for two hours at 4° C. using 20 μl of anti-FLAG (M2)-conjugated agarose beads (Sigma). Immunoprecipitations of endogenous IKKβ or NEMO were performed using 1 μg of specific rabbit polyclonal antibodies (Santa Cruz) plus 20 μl of Protein-A sepharose (Amersham-Pharmacia). For immunoblotting, precipitates were washed three times with TNT, twice with PBS then suspended in SDS-sample buffer. Proteins were separated by SDS-PAGE (10%), transferred to PVDF membranes and visualized by enhanced chemiluminesence (Amersham-Pharmacia).

Figure 2B:
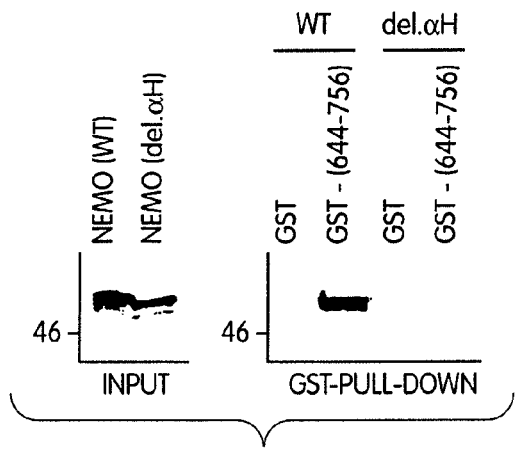
Figure 2C:
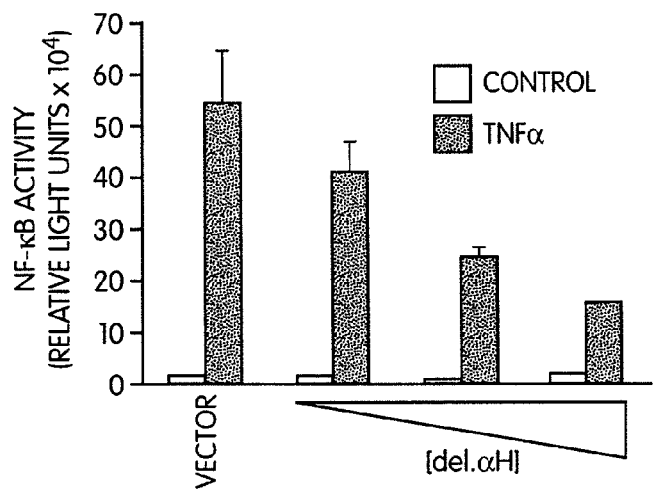

These results establish that the interaction domain lies between residues 44 and 86, a region including the first α-helix of NEMO. A mutant was therefore made in which α-helix up to the first coiled-coil domain was deleted (residues T50-L93; del.αH). This mutant did not interact with IKKβ-(644-756) (FIG. 2B). Furthermore transfection studies using pBIIX-luciferase demonstrated that del.αH inhibited TNFα-induced NF-κB activity (FIG. 2C) confirming previous reports that the COOH-terminus of NEMO which can not interact with IKKβ, is a dominant-negative inhibitor of NF-κB (Mercurio et al., (1999) Mol. Cell. Biol. 19, 1526-1538; Rothwarf et al., (1998) Nature 395, 297-300). Taken together, FIGS. 1 and 2 show that the interaction between IKKβ and NEMO occurs via the COOH-terminus of IKKβ and the first α-helical region of NEMO. These findings suggest a model in which the NH2-terminus of NEMO anchors it to the IKK-complex leaving the remainder of the molecule containing several protein:protein interaction domains free and accessible for interacting with upstream regulators of IKK function.

Example 2

NEMO Regulation of IKKB Function Through Interaction at NBD

Figure 3A:
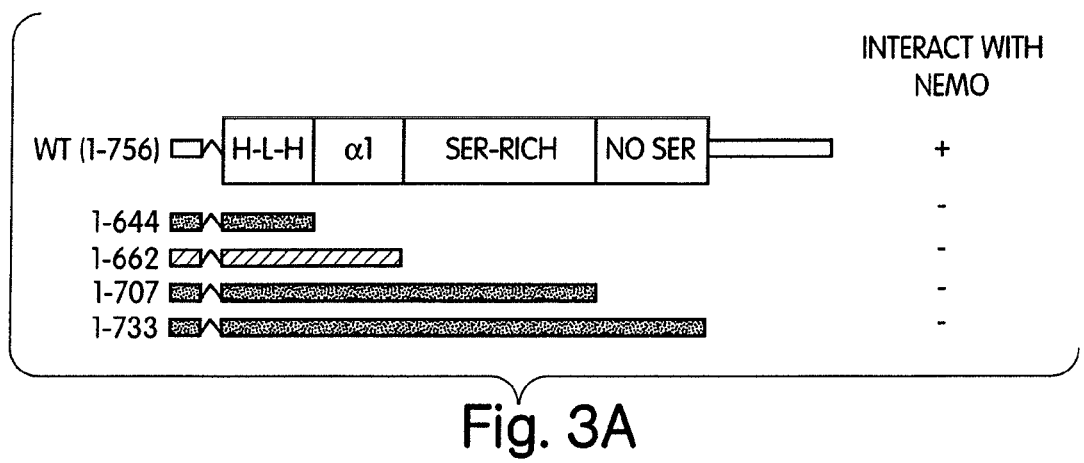
FIG. 3 depicts results from experiments indicating that interaction with NEMO and functional kinase activity requires an IKKα-homologous region of the IKKβ COOH-terminus. (A) Truncation mutations of IKKβ sequentially omitting the extreme COOH-terminus (1-733), the serine-free region (1-707), the serine rich-domain (1-662) and the α1-region (1-644) were expressed and labeled by in vitro translation and used for GST pull-down by GST-NEMO (FIG. 1A). None of the mutants interacted with GST alone. (B) Sequence alignment of the extreme COOH-termini of IKKβ and IKKα. The α2- and glutamate-rich regions are indicated and the six identical amino acids are shaded. (C) Wild-type IKKβ and the truncation mutants (1-733 and 1-744) were [$^{35}$S]-methionine-labeled (input) and used for in vitro pull down with either GST alone or GST-NEMO. (D) HeLa cells were transfected for forty-eight hours with 1 µg/well of the indicated FLAG-tagged constructs followed by immunoprecipitation using anti-FLAG. The immunoprecipitates were incubated in kinase buffer containing [$^{32}$P]-labeled γATP for fifteen minutes at 30° C. then washed with lysis buffer containing 1% Triton-100. Resulting complexes were separated by SDS-PAGE (10%) and visualized by autoradiography (upper panel). The lower panel is an immunoblot from identical samples demonstrating equivalent amounts of transfected protein in each lane. (E) HeLa cells were transfected for 48 hours with 1 µg/ml of the indicated constructs or empty vector (pcDNA-3) together with pBIIx-luciferase. NF-κB activity was determined by luciferase assay. (F) HeLa cells transfected for forty-eight hours with FLAG-tagged versions of either IKKβ (wild-type) or IKKβ-(1-733) were either untreated (−) or treated for seven minutes (+) with TNFα (10 ng/ml). Following lysis and immunoprecipitation using anti-FLAG, immune-complex kinase assay (upper panels) was performed. Identical samples were immunoprecipitated and immunoblotted with anti-FLAG (lower panels).

To fully characterize the NEMO-interaction domain of IKKβ further truncation mutants between residues V644 and S756 (FIG. 3A) were constructed. Immediately after the HLH, the amino acid sequence to the cysteine at position 662 exhibits 72% identity with IKKα (denoted α$_1$ in FIG. 3A). Following this, the region up to E707 is a serine-rich domain previously reported to be a target for auto-phosphorylation and to function in down-regulating IKKβ activity after stimulation by pro-inflammatory cytokines (Delhase et al., (1999) Science 284, 309-313). The sequence succeeding this contains no serine residues until position 733. Mutants sequentially omitting each of these regions were [$^{35}$S]-methionine-labeled and used in GST-pull-down assays as described above. FIG. 3A summarizes the results from these experiments demonstrating that none of the IKKβ mutants precipitated with GST-NEMO and indicating that the interaction domain resides in the extreme COOH-terminus between residues F734 and S756.

Figure 3B:
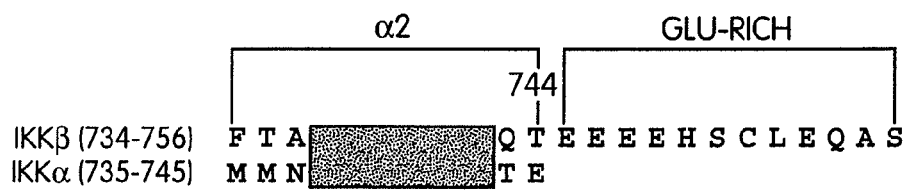

Comparison of this short segment of IKKβ with the corresponding region of IKKα reveals two striking structural characteristics (FIG. 3B). First, the sequence from F734 to T744 of IKKβ (α2 in FIG. 3B) is identical to the equivalent sequence in IKKα (L737 to L742 of IKKβ and L738 to L743 of IKKα). Second, the sequence of IKKβ extends beyond the COOH-terminal residue of IKKα (E745) for twelve amino acids comprising a highly acidic region in which five of the residues are glutamates (FIG. 3B). The marked similarity between the α2-region of IKKβ and the extreme COOH-terminus of IKKα together with previous reports that NEMO does not interact with IKKα in vitro (Mercurio et al., (1999) Mol. Cell. Biol. 19, 1526-1538; Yamaoka et al., (1998) Cell 93, 1231-1240; Rothwarf et al., (1998) Nature 395, 297-300) led to the hypothesis that the NEMO-interaction domain would be the glutamate-rich portion of IKKβ (E745 to S756).

Figure 3C:
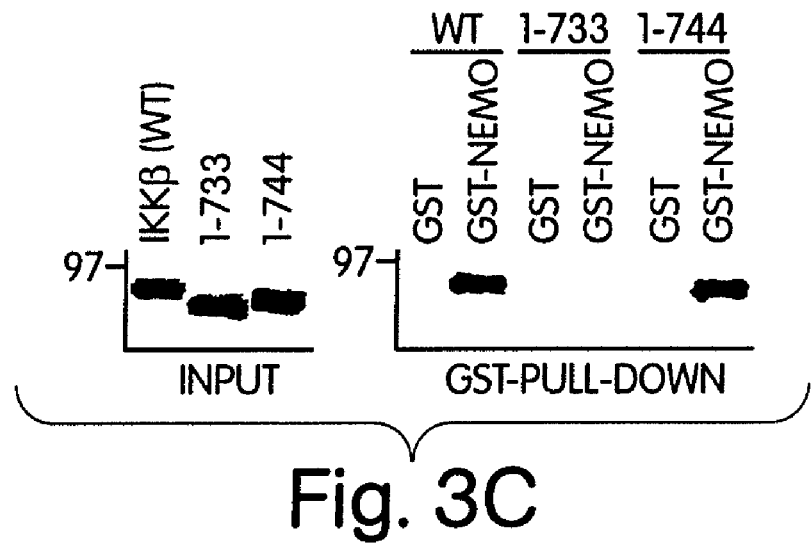

To test this hypothesis, a truncation mutant omitting this region was made (1-744; FIG. 3C) and investigated for its ability to interact with GST-NEMO. The mutant associated with GST-NEMO to an equal extent as wild-type IKKβ (FIG. 3C); these results have been confirmed by co-immunonoprecipitating epitope-tagged NEMO and IKKβ-(1-744) from lysate of transiently transfected COS cells. These findings demonstrate that the NEMO-interaction domain of IKKβ is within the α2-region of the COOH-terminus.

Figure 3D:
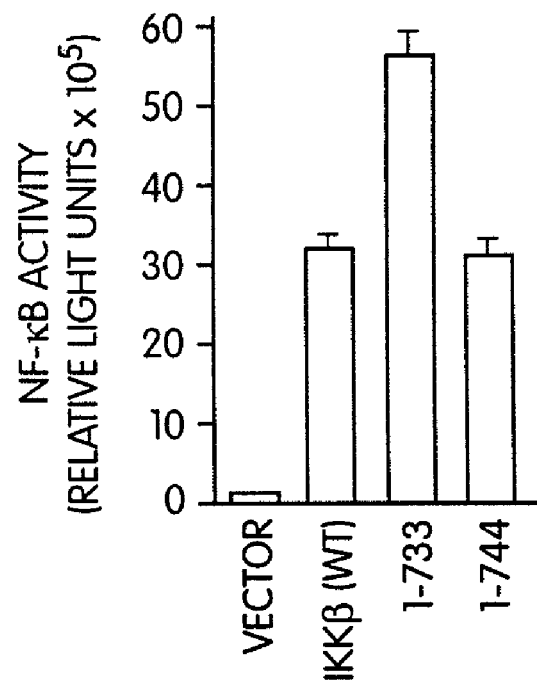

IKKβ COOH-terminal truncation mutants were next used to test the effects of NEMO association on basal and induced activity of IKKβ. FIG. 3D shows that truncation of IKKβ at V644, eliminating the serine-rich region (see FIG. 3A), resulted in complete loss of basal auto-phosphorylation. In contrast, a mutant containing the serine-rich region (1-733), exhibited significantly higher levels of auto-phosphorylation than wild-type IKKβ (FIG. 3D). Intriguingly, the level of auto-phosphorylation of IKKβ-(1-744) which contains the NEMO-binding α2-region, was identical to that observed with the wild-type kinase. To test the effects that these mutations have on basal kinase activity, mutants were transiently transfected into HeLa cells and NF-κB activity determined by luciferase assay as described in Example 1. The results in FIG. 3D demonstrate that IKKβ-(1-644) did not induce NF- κB activity whereas IKKβ-(1-733) caused increased activation compared with wild-type (FIG. 3E). Furthermore, NF-κB activity induced by IKKβ-(1-744) was identical to that induced by wild-type IKKβ.

These results demonstrate that basal auto-phosphorylation and kinase activity of IKKβ is dependent on the ability of NEMO to associate with the kinase. One explanation for these observations may be that NEMO recruits a phosphatase to the IKK-complex that regulates basal IKKβ function by targeting the serine-rich region of the COOH-terminus. Inability to bind NEMO therefore prevents phosphatase recruitment and causes increased phosphorylation within this region.

To directly test the effect that loss of the α2-region has on the catalytic activity of IKKβ, an immune-complex kinase assay was performed on lysate from transfected HeLa cells (FIG. 3F). For immune-complex kinases assays, precipitates were washed with TNT then with kinase buffer (20 mM HEPES pH 7.5, 20 mM MgCl2, 1 mM EDTA, 2 mM NaF, 2 mM β-glycerophosphate, 1 mM DTT, 10 μM ATP). Precipitates were then incubated for fifteen minutes at 30° C. in 20 μl of kinase buffer containing GST-IκBα-(1-90) and 10 μCi [$^{32}$P]-γ-labeled ATP (Amersham-Pharmacia). The substrate was precipitated using glutathione-agarose (Amersham-Pharmacia) and separated by SDS-PAGE (10%). Kinase activity was determined by autoradiography. Phosphorylated proteins associated with the kinase complex appeared on autoradiographs because the immuno-precipitated complex was not removed prior to GST-substrate precipitation. Activity of IKKβ (wild-type) was low in untreated cells but was markedly enhanced after treatment with TNFα. Consistent with the data presented in FIG. 3E, basal activity of IKKβ-(1-733) was significantly higher than wild-type, however this activity was not further enhanced by treatment with TNFα. (FIG. 3F). Furthermore, basal and TNFα-induced catalytic activity of IKKβ-(1-744) was identical to the activity of IKKβ (WT). In addition to phosphorylated GST-IκBα, auto-phosphorylated IKKβ proteins were also detected (FIG. 3F, top bands). Following TNFα treatment, IKKβ (WT) and IKKβ-(1-744) became rapidly autophosphorylated whereas the already high basal phosphorylation of IKKβ-(1-733) was only slightly enhanced (FIG. 3F). A previous study showed that auto-phosphorylation serves to down-regulate TNFα-induced IKKβ activity by causing conformational changes within the protein (Delhase et al., (1999) Science 284, 309-313). Taken together, these findings (FIGS. 3D-F) demonstrate that in the absence of NEMO, IKKβ becomes auto-phoshorylated, basally active and refractory to TNFα-induced signals indicating that NEMO plays a fundamental role in the down-regulation as well as activation of IKKβ activity.

An additional band representing a phosphorylated protein appeared only in the samples from TNFα-induced IKKβ (WT) and IKKβ-(1-744) transfected cells (FIG. 3F). The molecular weight of this protein (49 kDa) strongly suggests that it is endogenous NEMO associated with the precipitated complex. This is supported by the absence of the band in either precipitate (+/−TNFα) from IKKβ-(1-733) transfected cells. This protein has been identified as phosphorylated NEMO by dissociating the precipitated complex in SDS and re-immunoprecipitating [$^{32}$P]-labeled NEMO using specific anti-NEMO antibodies. Induced phosphorylation of NEMO may therefore represent a further level of regulation of the activity of the IKK complex.

Example 3

Identification of the NBD on IKKA

Since the α2-region of IKKβ strongly resembles the COOH-terminus of IKKα (FIG. 3B), the ability of IKKα to interact with NEMO was tested.

Figure 4A:
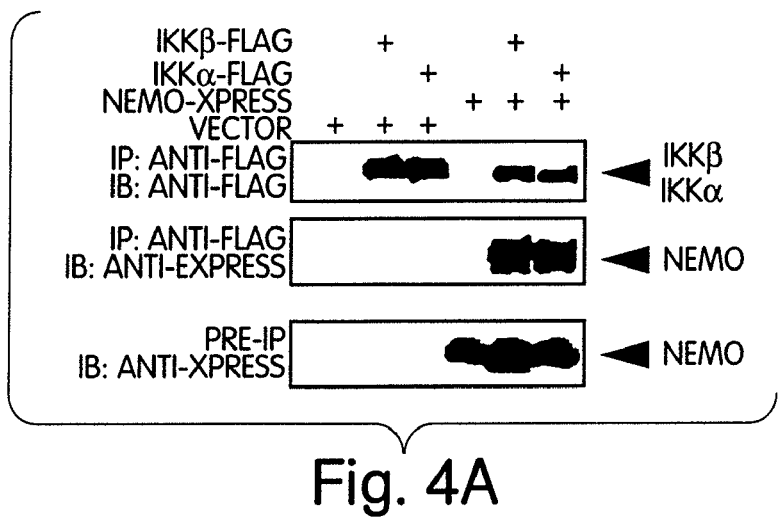
FIG. 4 depicts results from experiments indicating that association of NEMO with IKKβ and IKKα reveals the NEMO binding domain (NBD) to be six COOH-terminal amino acids. (A) COS cells transiently transfected with vector alone, FLAG-tagged IKKα or IKKβ (1 µg/well) or xpress-tagged NEMO (1 µg/well) to a total DNA concentration of 2 µg/well as indicated. Following lysis, immunoprecipitations (IP) were performed using anti-FLAG (M2) and the contents of precipitates visualized by immunoblotting (IB) with either anti-FLAG (M2) or anti-xpress. A portion of pre-IP lysate was immunoblotted with anti-xpress to ensure equivalent levels of NEMO expression in transfected cells. (B) Wild-type IKKα and IKKα-(1-737) were expressed and labeled (input) and used for GST pull-down using GST or GST-NEMO. (C) Full length cDNA encoding human IKKi was obtained by RT-PCR from HeLa cell mRNA using the Expand™ Long Template PCR System (Boehringer Mannheim), the forward primer (5'-CTAGTCGAATTCACCATGCAGAGCACAGCCAATTAC) (SEQ ID NO: 22) and the reverse primer (3'-CTAGTCTCTAGATTAGACATCAG-GAGGTGCTGG) (SEQ ID NO: 23) and cloned into the EcoRI and XbaI sites of pcDNA-3. GST pull-down analysis was performed using [$^{35}$S]-methionine-labeled IKKα, IKKβ and IKKi. (D) A deletion mutant of IKKβ lacking the NBD (del.NBD) was [$^{35}$S]-methionine-labeled (input) and used for GST pull down analysis. (E) A Fauchere-Pliska hydrophobicity plot of the COOH-terminus (N721-S756) of human IKKβ was generated using MacVector (version 6.5.3) software. The NBD (L737-L742) is boxed. (F) COS cells were transfected for forty-eight hours with a total of 2 µg DNA/well of either vector alone, vector plus NEMO-FLAG or NEMO-FLAG plus xpress-tagged versions of IKKβ-(1-744) containing point mutations within the NBD as indicated. Following lysis and immunoprecipitation using anti-FLAG (M2), immunoblot analysis was performed with either anti-FLAG or anti-xpress. The level of expressed protein in pre-IP lysate was determined by immunoblotting with anti-xpress (lower panel). (G) HeLa cells were transiently transfected for forty-eight hours with the indicated constructs together with pBIIX-luciferase and NFκB activity in lysate was measured by luciferase assay.
Figure 4B:
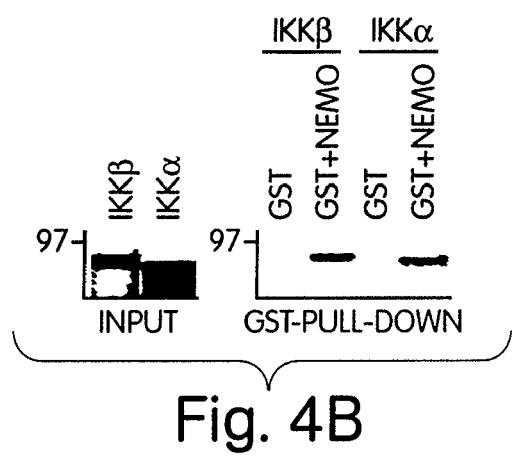

Immunoprecipitations from lysate of COS cells transiently transfected with xpress-tagged NEMO together with FLAG-tagged versions of either IKKα or IKKβ were performed using anti-FLAG as described in Example 1. FIG. 4A shows that NEMO interacted equally well with both IKKβ and IKKα. It is possible that in this experiment the interaction with IKKα is not direct but due instead to the formation of a complex containing endogenous IKKβ, FLAG-IKKα and xpress-NEMO. A GST-pull-down assays was therefore performed using GST-NEMO and [$^{35}$S]-methionine-labeled versions of either wild-type IKKα or a truncated IKKα mutant lacking the eight COOH-terminal amino acids (1-737: FIG. 4B). In agreement with the findings presented above (FIG. 4A), but in contrast to previous reports (Mercurio et al., (1999) Mol. Cell. Biol. 19, 1526-1538; Yamaoka et al., (1998) Cell 93, 1231-1240; Rothwarf et al., (1998) Nature 395, 297-300), wild-type IKKα interacted with NEMO in vitro whereas the truncated mutant did not (FIG. 4B). These results not only demonstrate that IKKα interacts with NEMO but also shows that it does so via the COOH-terminal region containing the six amino acids shared between IKKα and the α2-region of IKKβ (FIG. 3B). Gene-targeting studies have demonstrated profound differences in the activation of IKKα and IKKβ by TNFα (Woronicz et al., (1997) Science 278, 866-869; Zandi et al., (1997) Cell 91, 243-252; Mercurio et al., (1997) Science 278, 860-866; DiDonato et al., (1997) Nature 388, 548-554; Régnier et al., (1997) Cell 90, 373-383).

The present findings indicate that the basis of this difference is not due to differential recruitment of NEMO (Delhase et al., (1999) Science 284, 309-313; Takeda et al., (1999) Science 284, 313-316; Hu et al., (1999) Science 284, 316-20; Li et al., (1999) Science 284, 321-325; Li et al., (1999) J. Exp. Med. 189, 1839-1845; Li et al., (1999) Genes Dev. 13, 1322-1328; Tanaka et al., (1999) Immunity 10, 421-429). Instead the difference most likely lies in the ability of each kinase to integrate NEMO-associated signaling components into an activation response, presumably through differences in the inherent regulatory features of the individual kinases.

Figure 4C:
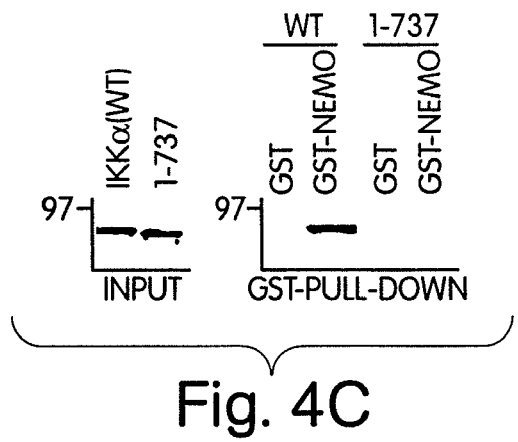

Further evidence that this short COOH-terminal sequence constitutes the NEMO-interaction domain of the IKKs was obtained when we tested the ability of the recently described IKK-related kinase IKKi (Shimada et al., (1999) Int. Immunol. 11, 1357-1362) to interact with NEMO. Sequence comparison with IKKα and IKKβ (Shimada et al., (1999) Int. Immunol. 11, 1357-1362; Woronicz et al., (1997) Science 278, 866-869; Zandi et al., (1997) Cell 91, 243-52; Mercurio et al., (1997) Science 278, 860-866; DiDonato et al., (1997) Nature 388, 548-554; Régnier et al., (1997) Cell 90, 373-383) reveals that IKKi does not contain the α2-region in its COOH-terminus (Shimada et al., (1999) Int. Immunol. 11, 1357-1362) and consistent with this being the NEMO binding domain we found that IKKi does not interact with GST-NEMO in pull down assays (FIG. 4C). This finding indicates that NEMO is not required for the functional activity of IKKi and this is supported by the inability of IKKi to respond to signals induced by either TNFα or IL-1β (Shimada et al., (1999) Int. Immunol. 11, 1357-1362).

Example 4

Mutation of Amino Acid Residues in the NBD

Figure 4D:
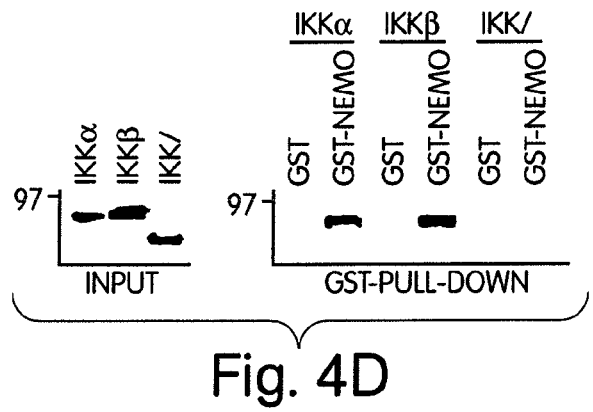
Figure 4E:
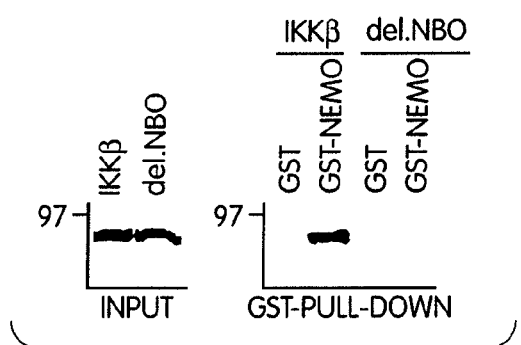
Figure 4F:
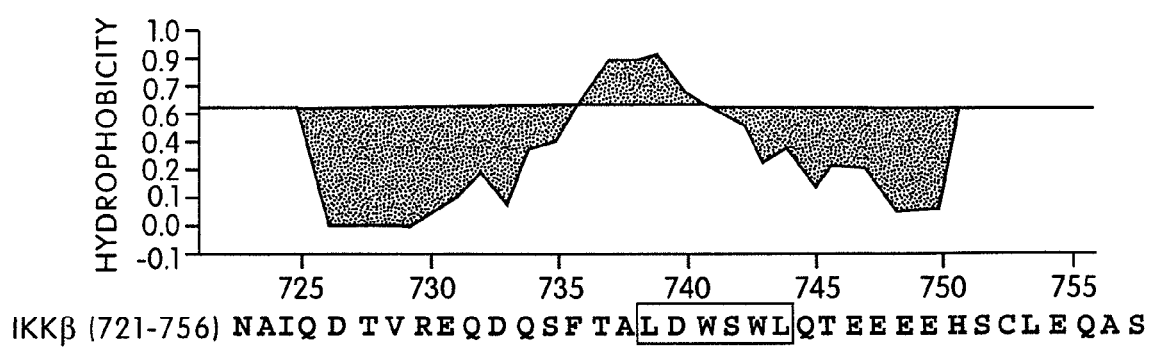
Figure 4G:
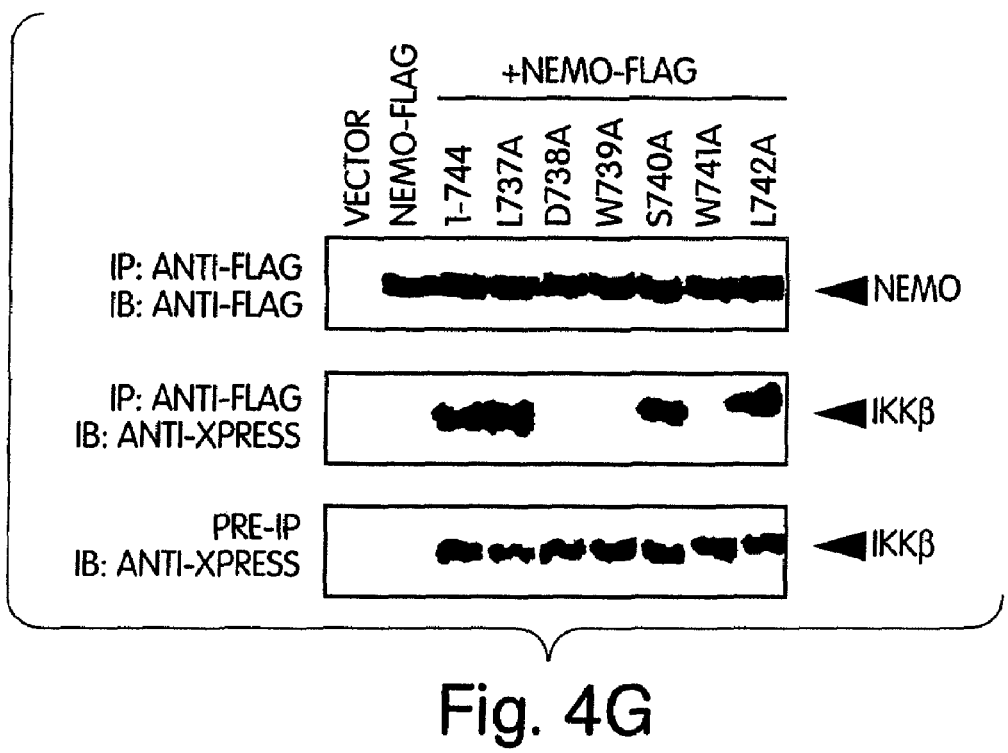
Figure 4H:
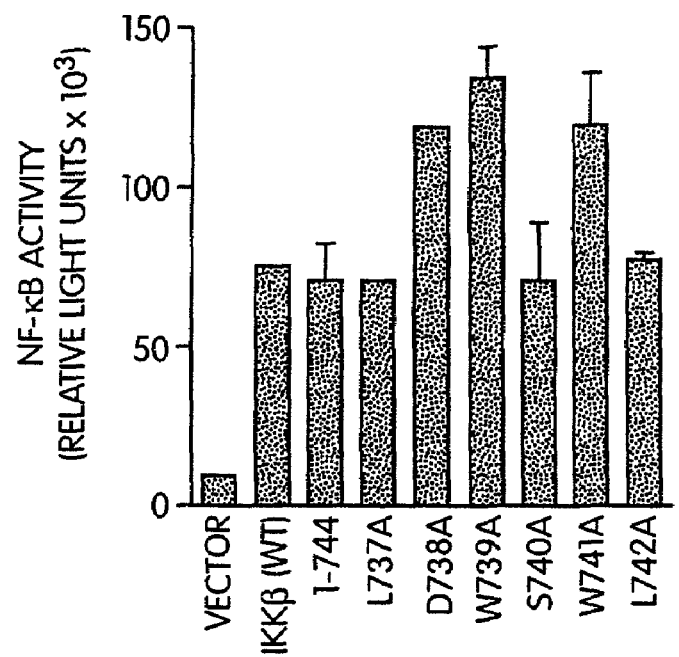

Having determined that the α2-region of IKKβ, and the equivalent six amino acid sequence of IKKα are critical for interaction with NEMO [designated NEMO binding domain (NBD)], a deletion mutant in IKKβ lacking the six amino acids from L737 to L742 (del.NBD) was constructed. This deletion mutant did not associate with GST-NEMO (FIG. 4D). Examination of predicted structural and biochemical features of the NBD in context with surrounding residues suggests that it constitutes an inflexible hydrophobic "pocket" within a hydrophilic region of the IKKβ COOH-terminus (FIG. 4E). This suggests a model in which the NBD becomes buried within the first α-helical region of bound NEMO (FIG. 2) preventing its exposure to an aqueous environment thereby maintaining a strong inter-molecular interaction. Whether the interaction is indeed a function of this hydrophobicity remains to be determined, however we found that substitution of either W739 or W741 with alanine prevented association of NEMO with IKKβ (FIG. 4F). Therefore each of these hydrophobic tryptophan residues is critical for maintaining a functional NBD. In addition, mutation of D738 to alanine also prevented NEMO interaction indicating that a negatively charged residue at this position is required for NBD function. In contrast to these mutations, substitution of L737, S740 or L742 with alanine did not affect NEMO binding. To test the effects of these alanine substitutions on IKKβ function, HeLa cells were co-transfected with each of the point mutants together with pBIIX-luciferase reporter. Consistent with the observation that the basal activity of IKKβ is increased in the absence of associated NEMO, IKKβ-(1-733) (FIG. 3E), mutants that did not bind NEMO (D738A, W739A and W741A) activated NF-κB to a greater extent than wild-type IKKβ or IKKβ-(1-744) (FIG. 4G). In contrast, mutants containing substitutions that did not disrupt NEMO association (L737A, S740A and L742A) induced NF-κB to the same level as the controls. These results indicate that NEMO plays a critical role in the down-regulation of intrinsic IKKβ activity.

Further mutations in the NBD were analyzed (see Table 1) for their ability to affect NEMO binding to IKKβ using the GST pulldown assay explained in Example 3.

TABLE 1

Characterized NBD mutants and their ability to bind to NEMO.

| NBD Mutants- | Binds to NEMO | SEQ ID NO: |
|---|---|---|
| LDWSWL | yes | 2 |
| LDASAL | no | 3 |
| ADWSWL | yes | 4 |
| LDWSWA | yes | 5 |
| LAWSWL | no | 7 |
| LEWSWL | yes | 8 |
| LNWSWL | yes | 9 |
| LDASWL | no | 10 |
| LDFSWL | yes | 11 |
| LDYSWL | yes | 12 |
| LDWSAL | no | 13 |
| LDWSFL | yes | 14 |
| LDWSYL | no | 15 |
| LDWAWL | yes | 16 |
| LDWEWL | yes | 17 |

* The substituted amino acid residue is indicated by bold face.

Example 5

Agents which Interact with NBD to Block NEMO Binding

The relatively small size of the NBD makes it an attractive target for the development of compounds aimed at disrupting the core IKK complex. The relevance of this approach was investigated by designing cell-permeable peptides spanning the IKKβ NBD and determining their ability to dissociate the IKKβ-NEMO interaction.

The sequences of the two NBD peptides used in this study were [DRQIKIWFQNRRMKWKK]TALDWSWLQTE (wild-type) (SEQ ID NO:18) and [DRQIKIWFQNRRMK-WKK]TALDASALQTE (mutant) (SEQ ID NO:19). The antennapedia homeodomain sequence (Derossi et al., (1994) J. Biol. Chem. 269, 10444-10450; U.S. Pat. Nos. 5,888,762; 6,015,787 ; 6,080,724) is bracketed and the positions of the Wto A mutations are underlined. Both peptides were dissolved in DMSO to a stock concentration of 20 mM. For all experiments DMSO alone controls were no different from no peptide controls.

The wild-type NBD peptide consisted of the region from T735 to E745 of IKKβ fused with a sequence derived from the third helix of the antennapedia homeodomain that has been shown to mediate membrane translocation (Derossi et al., (1994) J. Biol. Chem. 269, 10444-10450). The mutant was identical except that the tryptophan residues (W739 and W741) in the NBD were mutated to alanine. FIG. 5A shows that the NBD (WT) but not the mutant dose-dependently inhibited in vitro pull-down of [$^{35}$S]-labeled IKKβ by GST-NEMO and [$^{35}$S]-labeled NEMO by GST-IKKβ-(644-756). To test the ability of the NBD peptides to enter cells and inhibit the IKKβ-NEMO interaction, HeLa cells were incubated with the peptides for different time periods and immunoprecipitated the IKK complex using anti-NEMO. In agreement with the in vitro data (FIG. 5A), wild-type but not mutant disrupted the formation of the endogenous IKK complex (FIG. 5B).

Example 6

Agents Which Block NEMO Function

Figure 5D:
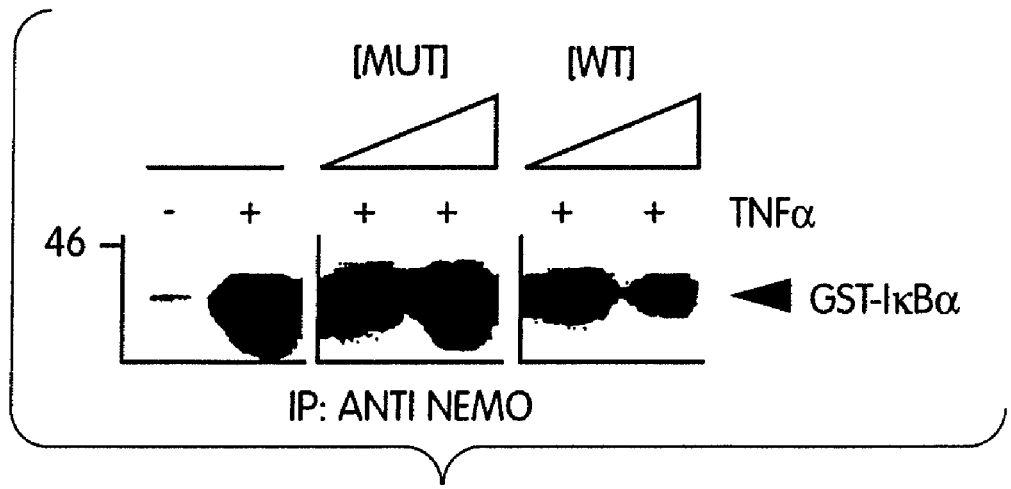
FIG. 5 depicts results from experiments indicating that a cell-permeable peptide spanning the IKKβ NBD inhibits the IKKβ/NEMO interaction, TNFα-induced NF-κB activation and NF-κB-dependent gene expression. (A) GST-pull-down analysis was performed using either GST-NEMO-in vitro translated IKKβ (upper panel) or GST-IKKβ-(644-756)-in vitro translated NEMO (lower panel). The assay was performed in the absence (no peptide) or presence of increasing concentrations (125, 250, 500 or 1000 µM) of either mutant (MUT) or wild-type (WT) NBD peptide. (B) HeLa cells were incubated with either peptide (200 µM) for the times indicated. Following lysis, the IKK complex was immunoprecipitated using anti-NEMO and the resulting immunoblot probed with anti-IKKβ. (C) HeLa cells were transfected for forty-eight hours with pBIIX-luciferase then incubated for two hours in the absence (control) or presence of mutant or wild-type NBD peptide (100 and 200 µM of each). Subsequently the cells were either treated with TNFα (10 ng/ml) as indicated (left panel) or left untreated (right panel) for a further four hours after which NF-κB activation was measured by luciferase assay. (D) HeLa cells were incubated for three hours with increasing concentrations (50, 100 or 200 µM) of each peptide followed by treatment for fifteen minutes with TNFα (10 ng/ml) as indicated (+). Following lysis, nuclear extracts were made and 10 µg of protein from each sample was used for EMSA using a specific [$^{32}$P]-labeled κB-site probe. (E) Primary HUVEC were pre-incubated for two hours with of wild-type (left) or mutant (right) NBD peptides (100 µM) then stimulated with TNFα (10 ng/ml) for a further six hours. Control cells received no peptide. Cells were stained with either anti-E-selectin (H4/18) or a non-binding control antibody (K16/16) and expression was measured by FACS (FACSort, Becton Dickinson). The profiles show E-selectin staining in the absence (shaded) and presence (solid line) of TNFα and control antibody staining under the same conditions (dashed line, no TNFα; dotted line, TNFα).

The effects of the NBD peptides on signal-induced activation of NF-κB were investigated next. After transfecting HeLa cells with the pBIIX-luciferase reporter, cells were preincubated with wild-type or mutant peptides, treated with TNFα and NF-κB activation measured by the luciferase reporter assay. As shown in FIG. 5C (left panel), the wild-type NBD peptide inhibited TNFα-induced NF-κB activation whereas the mutant had no effect. Interestingly, the basal NF-κB activity was enhanced by treatment with the wild-type peptide (FIG. 5C; right panel), a finding which concurs with results from previous mutational analysis (FIGS. 3E-F and 4G). This indicates that removal of NEMO increases the basal, intrinsic activity of IKK, while abolishing its responsiveness to TNFα. Further analysis using electrophoretic mobility shift assays (EMSA) also demonstrated that only the wild-type NBD peptide inhibited TNFα-induced activation and nuclear translocation of NF-κB (FIG. 5D). Taken together these results demonstrate that delivery of an intact NBD peptide into cells disrupts the IKKβ-NEMO interaction and prevents pro-inflammatory signals from activating NF-κB. In contrast, transduction with a peptide containing mutations at the tryptophan residues that are critical for maintaining the NEMO interaction has no effect.

Example 7

Agents Capable of Down-Regulating E-Selectin

Figure 5E:
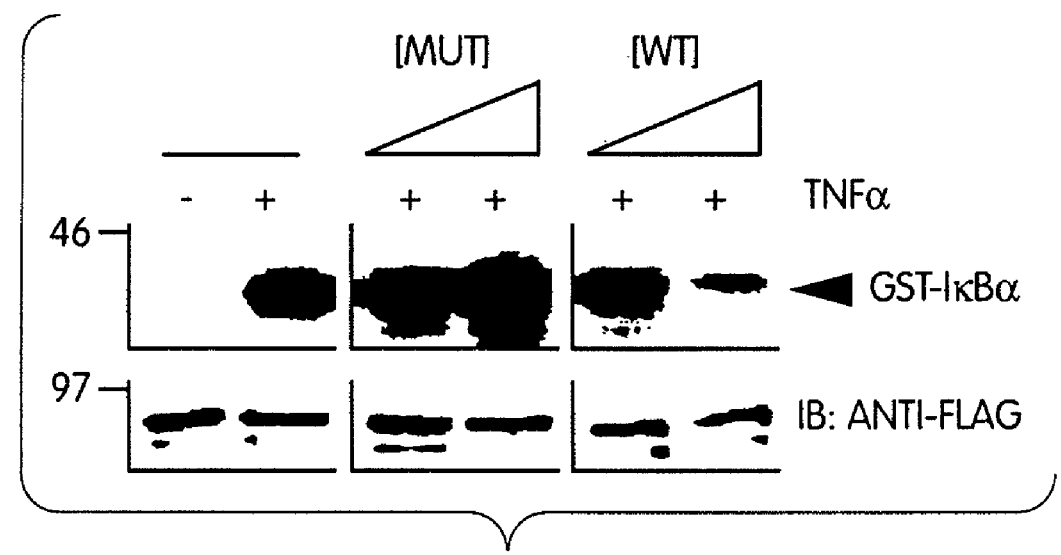
Figure 5F:
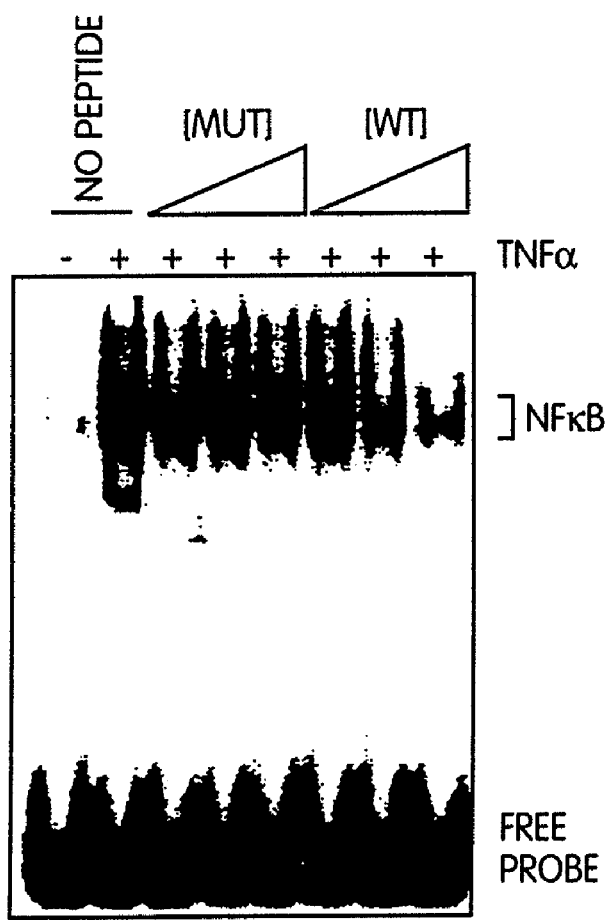
Figure 5G:
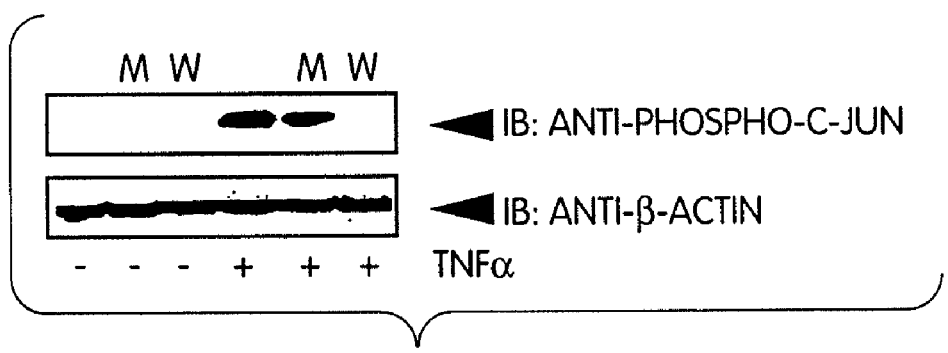
Figure 5H:
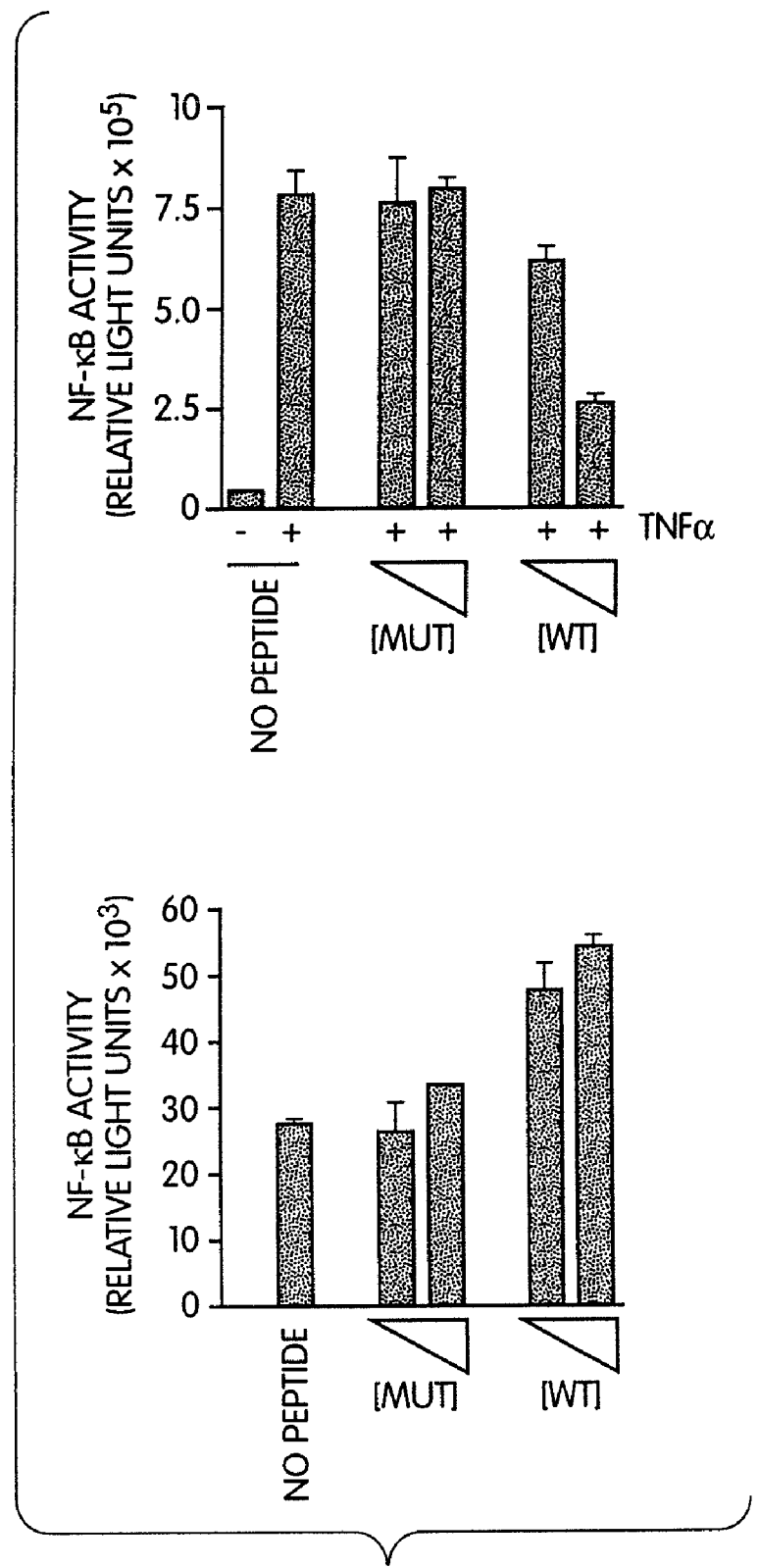

Many proteins involved in the initiation and maintenance of inflammatory responses require NF-κB activation for induced expression of their genes (Ghosh et al., (1998) Annu. Rev. Immunol. 16, 225-260; May & Ghosh, (1998) Immunol. Today 19, 80-88). One such protein, E-selectin, is a leukocyte adhesion molecule expressed on the luminal surface of vascular endothelial cells after activation by pro-inflammatory stimuli such as IL-1 or TNFα (Pober et al., (1986) J. Immunol. 436, 1680-1687; Bevilacqua et al., (1987) Proc. Natl. Acad. Sci. USA 84, 9238-9242; Collins et al., (1995) FASEB J. 9, 899-909). Expression of E-selectin and other NF-κB-dependent adhesion molecules is crucial for the arrest and recruitment of leukocytes into sites of acute and chronic inflammation. To assess the anti-inflammatory potential of the NBD peptide, primary human umbilical vein endothelial cells (HUVEC) were pretreated with the wild-type and mutant peptides and E-selectin expression induced with TNFα. Consistent with the effects on basal NF-κB activation (FIG. 5C), the wild-type NBD peptide induced low level expression of E-selectin (FIG. 5E). However, after TNFα-treatment the wild-type but not mutant significantly reduced expression of E-selectin (FIG. 5E). Inhibition by wild-type NBD peptide reduced expression to the level induced by the peptide in the absence of TNFα.

The importance of the present invention can be viewed on two levels. First, Applicants have identified the structural requirements for the association of NEMO with the IKKs and found that association with IKKβ is dependent on three amino acids (D738, W739 and W741) within the NBD. Furthermore, NEMO not only functions in the activation of IKKβ but it also has a critical role in suppressing the intrinsic, basal activity of the IKK complex. The second level of importance is the obvious clinical use for drugs targeting the NBD. Applicants have demonstrated that a cell-permeable peptide encompassing the NBD is able to not only inhibit TNFα-induced NF-κB activation but also reduce expression of E-selectin, an NF-κB-dependent target gene, in primary human endothelial cells. The NBD is only six amino acids long, and therefore it is within the ability of one skilled in the art to design peptido-mimetic compounds that disrupt the core IKK complex. Since the effect of disrupting the complex is to increase the basal activity of the IKK, treatment with an NBD-targeting compound can avoid issues of toxicity, e.g., due to hepatocyte apoptosis, that might arise from administering drugs that completely abolish the activity of NF-κB. Hence, identification of the NBD is a means for the development of novel anti-inflammatory drugs that prevent activating signals from reaching the IKK complex, yet maintain a low level of NF-κB activity and avoid potential toxic side-effects.

Example 8

NBD Peptide-Mediated Inhibition of Inflammatory Response IN VIVO

The NBD peptide was tested for its ability to inhibit inflammatory responses in animals using two distinct models of acute inflammation. In the first model, ear edema was induced in mice using phorbol-12-myristate-13-acetate (PMA) and the effects of topical administration of the NBD peptides were measured. Ear edema using PMA was induced in replicate groups of age and sex matched mice as previously described (Chang et al., (1987) Eur. J. Pharmacol. 142, 197-205). Twenty μl of either NBD peptides (200 μg/ear), dexamethasone (40 μg/ear) or vehicle (DMSO:Ethanol; 25:75 v/v) was applied topically to the right ear of mice thirty minutes before and thirty minutes after the application of 20 μl of PMA (5 μg/ear) dissolved in ethanol. Ear swelling was measured six hours after PMA application using a microgauge and expressed as the mean difference in thickness between the treated (right) and untreated (left) ears. Statistical analysis of the data was performed using the students t-test. A value of p<0.05 was considered statistically significant.

Figure 6A:
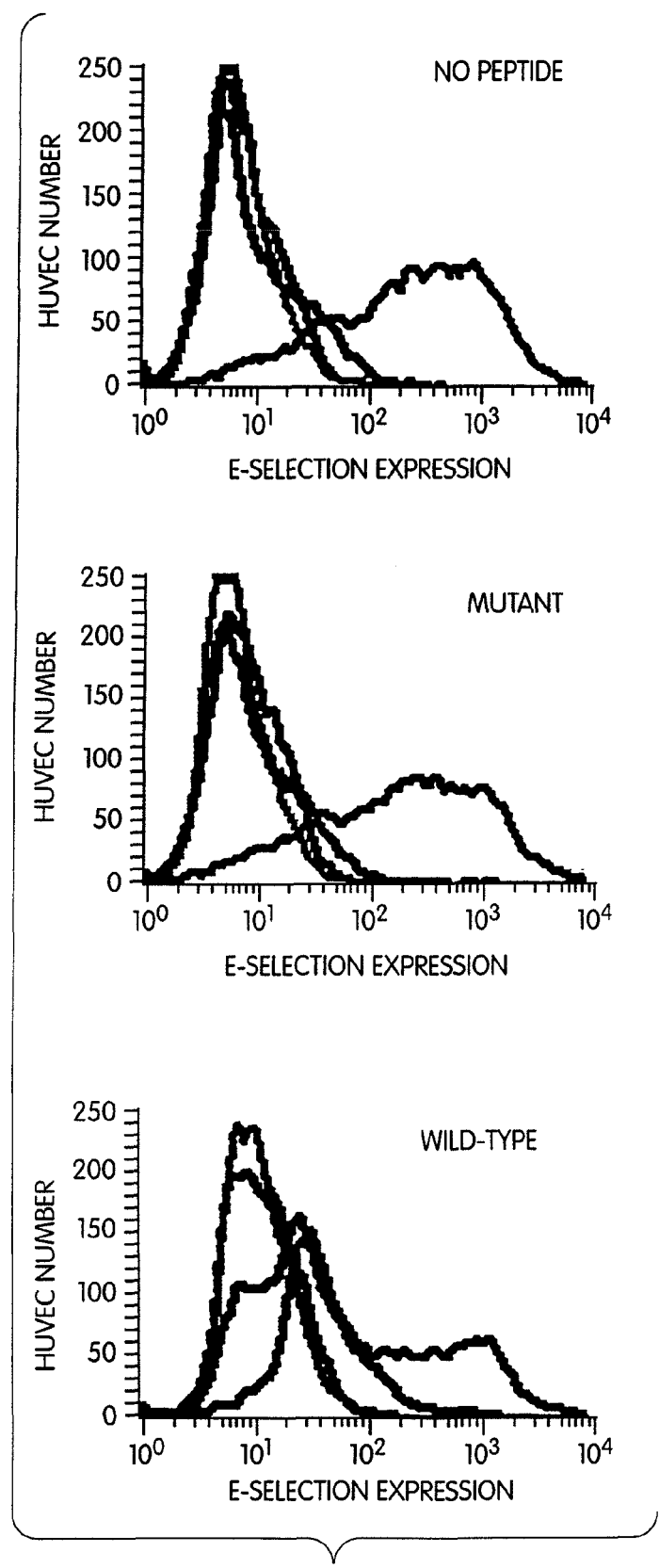
FIG. 6 depicts results from experiments indicating that the wild-type NBD peptide inhibits NF-κB-induced gene expression and experimentally induced inflammation. (A) PMA-induced ear edema in mice topically treated with either vehicle (VEH), dexamethasone (DEX) or NBD peptides was induced and measured as described in Example 8. Data are presented as mean differences in ear thickness±SD (*=p<0.05 compared with both untreated control [−] and vehicle [VEH]). (B) The effects of the NBD peptide compared with the effect of dexamethasone (DEX) on Zymosan (ZYM)-induced peritonitis in mice were determined as described again in Example 8. Control mice were injected with phosphate-buffered saline (PBS).

FIG. 6A shows that the wild type peptide significantly reduced (77±3% inhibition; p<0.05) PMA-induced ear thickening to the level observed with dexamethosone (82±9% inhibition; p<0.05). In contrast, the effect observed with an equivalent dose of mutant was insignificant (p=0.09). Neither peptide had an effect when administered in the absence of PMA (not shown).

In a second model, peritonitis was induced in mice by intraperitoneal (i.p.) injection of zymosan either alone or in combination with dexamethasone or the NBD peptides. For zymosan-induced peritonitis, measurement of peritoneal exudates and inflammatory cell collections from replicate groups of age and sex matched mice (C57BLJ6NCR) were performed as previously described (Getting et al., (1998) Immunology 95, 625-630). Groups of animals were injected concomitantly with one ml zymosan (1 mg/ml) and either dexamethasone (100 mg/ml) or the NBD peptides (200 mg/ml). The concentration of NOX (nitrate plus nitrite) present in the inflammatory exudates was measured using a colorimetric assay kit (Alexis Corporation) according to the manufacturers protocol.

Figure 6B:
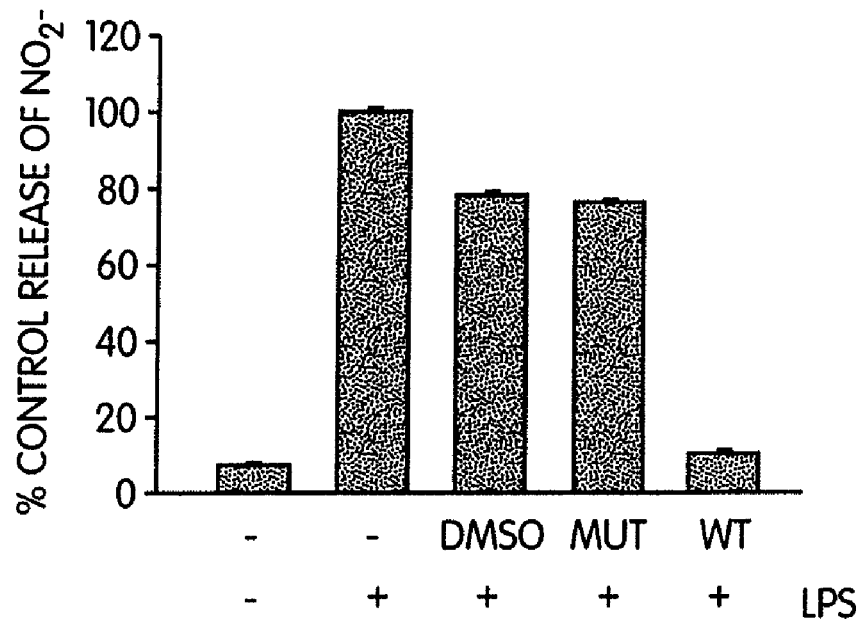

As shown in FIG. 6B zymosan injection caused an accumulation of inflammatory exudate fluids and migration of polymorphonuclear cells (PMN) into the peritoneum of these animals. Treatment of mice with wild type NBD peptide or dexamethasone significantly reduced exudate formation and PMN accumulation whereas the mutant had no effect.

Figure 6C:
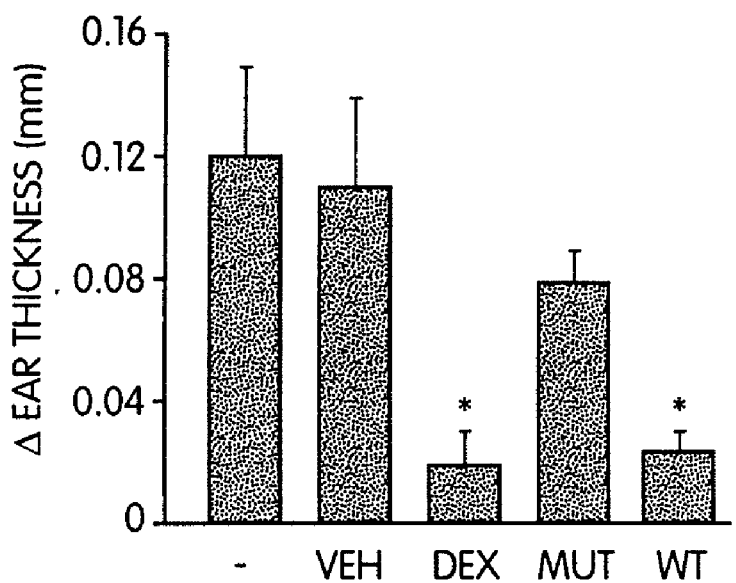
Figure 6D:
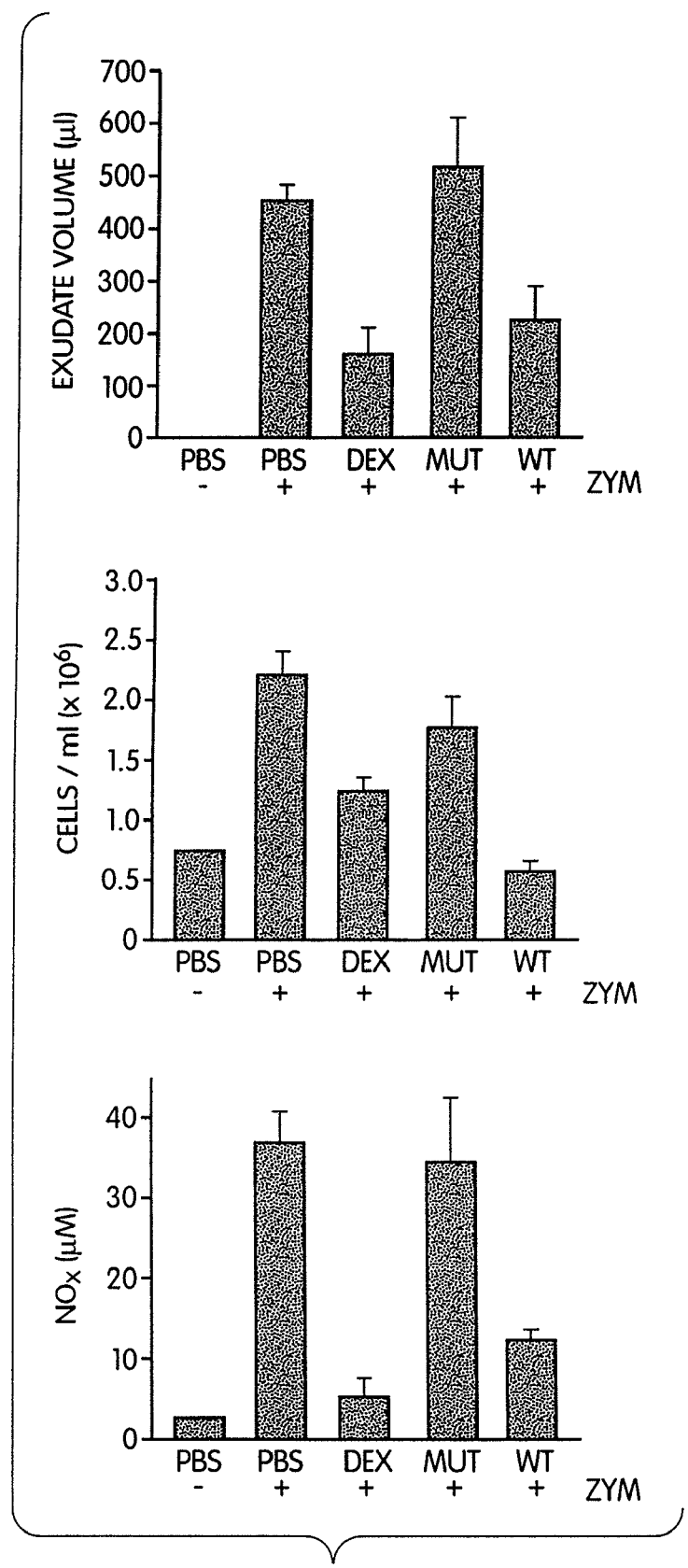

Various in vivo studies have demonstrated a role for NO in exudate formation and leukocyte migration into inflammatory sites (lalenti et al., (1992) Eur. J. Pharmacol. 211, 177-182; lalenti et al., (1993) Br. J. Pharmacol. 110, 701-706; Iuvone et al., (1998) Br. J. Pharmacol. 123, 1325-1330). Therefore the effects of the NBD peptides on NOX accumulation in the peritoneal exudates of zymosan-treated mice was investigated. FIG. 6C (lower panel) shows that dexamethasone and wild-type peptide reduced NOX by 86±7% and 66±4% respectively whereas the mutant had no effect. These results are consistent with previous studies demonstrating that reduction of exudate formation and cell accumulation closely correlate with inhibition of NF-κB activation and reduction of NO formation (D'Acquisto et al., (1999) Eur. J. Pharmacol. 369, 223-236; D'Acquisto et al., (1999) Naunyn-Schmeideberg's Arch. Pharmacol. 360, 670-675). Therefore the wild-type NBD peptide is an effective inhibitor of inflammation in experimental animal models.

Example 9

Inhibition of Osteoclast Differentiation by the NBD Peptide

The processes of bone morphogenesis and remodeling require the maintenance of a balance between the synthesis of bone matrix by osteoblasts and the resorbtion of bone by osteoclasts (Suda et al., (1992) Endocr. Rev. 13, 66-80; Suda et al., (1999) Endocr. Rev. 20, 345-357). Bone-resorbing osteoclasts are multinucleated giant cells that differentiate from myeloid precursors and various soluble factors including colony stimulating factor-1 (CSF-1), Interleukin-1 (IL-1), Tumor necrosis factor-α (TNF-α), IL-6 and IL-11 (Suda et al., (1992) Endocr. Rev. 13, 66-80; Suda et al., (1999) Endocr. Rev. 20, 345-357) that affect osteoclast differentiation at distinct stages. One factor that is critical for osteoclastogenesis is the recently described molecule named RANKL (receptor activator of NF-κB ligand) that is also known as ODF (osteoclast differentiation factor), OPGL (osteoprotegerin ligand) and TRANCE (TNF-related activation-induced cytokine) (Kong et al., (1999) Nature, 397, 315-323; Lacey et al., (1998) Cell 93, 165-176; Suda et al., (1999) Endocr. Rev. 20, 345-357; Wong et al., (1999) J. Leukoc. Biol. 65, 715-724; Yasuda et al., (1998) Proc. Natl. Acad. Sci. USA 95, 3597-3602). The receptor for RANKL is a member of the TNF-receptor family named RANK (receptor activator of NF-κB) (Anderson et al., (1997) Nature 390, 175-179; Dougall et al., (1999) Genes Dev. 13, 2412-2424) and binding of RANKL induces NF-κB activation (Anderson et al., (1997) Nature 390, 175-179; Darnay et al., (1998) J. Biol. Chem. 273, 20551-20555; Darnay et al., (1999) J. Biol. Chem. 274, 7724-31; Suda et al., (1999) Endocr. Rev. 20, 345-357; Wong et al., (1998) J. Biol. Chem. 273, 28355-28359). Moreover, osteoclast differentiation is dependent upon NF-κB activation and gene-targeting studies have demonstrated that mature osteoclasts fail to develop in mice lacking the p50 and p52 NF-κB subunits (Franzoso et al., (1997) Genes Dev. 11, 3482-3496).

Figure 7:
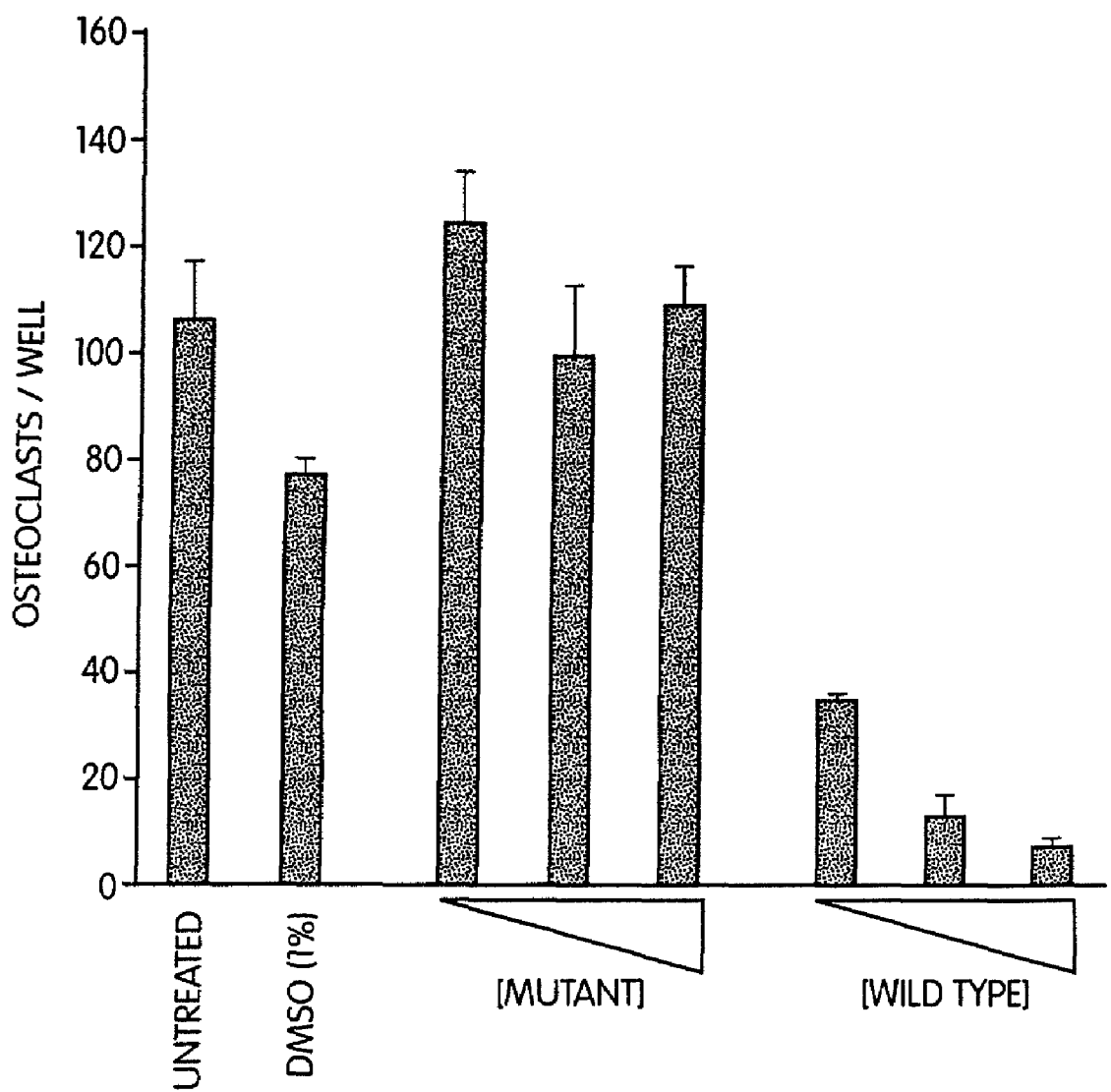
FIG. 7 depicts results from experiments indicating the dose dependent inhibition of osteoclast differentiation by wild-type but not mutant NBD peptides. Data are presented as the mean determination of triplicate samples±SD.

Osteoporosis is a severely debilitating disease characterized by an extensive loss of bone mass that is mediated by osteoclast-dependent bone resorbtion (Suda et al., (1992) Endocr. Rev. 13, 66-80; Suda et al., (1999) Endocr. Rev. 20, 345-357). It is therefore possible that selective inhibition of NF-κB activation in osteoclast precursor cells would prevent osteoclast differentiation and provide the basis for therapeutically effective drugs for the treatment of osteoporosis. Therefore the effect of the NBD peptides on osteoclast differentiation was tested using a previously described in vitro model (Jimi et al., (1999) Exp. Cell Res. 247, 84-93). Mouse bone marrow cells plated into 48-well tissue culture trays were incubated with human macrophage-colony stimulating factor (M-CSF; 20 ng/ml) and human RANKL (100 ng/ml) for six days in the absence or presence of various concentrations (6.25, 12.5 and 25 mM) of either mutant or wild-type NBD peptide. The cells were then fixed and stained for the osteoclast phenotypic marker tartrate-resistant acid phosphatase (TRAP) and TRAP-positive mutinucleated cells containing more than three nuclei were counted as osteoclasts. Triplicate samples were counted and results were calculated as means±SD. As shown in FIG. 7 the wild type but not mutant peptide dose-dependently inhibited osteoclast differentiation.

This data demonstrates that disruption of the core IKK complex by a cell permeable NBD peptide that inhibits NF-κB activation prevents RANKL-induced osteoclast differentiation indicating that drugs specifically targeting the NBD will be effective for the treatment of osteoporosis. As an extension of these in vitro studies, the same peptides can be analyzed for their effects on osteoporosis in vivo. Ovarectomized mice (Charles River Labs) that exhibit severe osteoporosis are treated with the NBD peptides and the effects on bone density over a timecourse of treatment determined.

Example 10

Effect of NBD Peptides on Other NF-KB Mediated Disorders

In addition, it is also possible to examine the effects of the NBD peptides on asthma. NF-κB activation in bronchiolar epithelial cells, T-cells and bronchiolar macrophages has been observed in the airways of asthmatic patients and in animal models of asthma (Ray & Cohn, (1999) J. Clin. Invest. 104, 985-993; Christman et al., (2000) Chest 117, 1482-1487). In addition, many agents that induce asthma cause NF-κB activation and many of the genes that encode proteins involved in asthma (i.e., leukocyte adhesion molecules, various chemokines, inducible nitric oxide synthase) are NF-κB-dependent. An established mouse model of asthma (Kleeberger et al., (1990) Am. J. Physiol. 258, 313-320) can be used to test the effects of aerosol administration of the NBD peptides on progression of these conditions associated with asthma. In a similar manner, the effects of the NBD peptides on septic shock can also be measured. Septic shock involves the expression of many NF-κB dependent genes (i.e., TNF, IL-1) that are induced by bacterial endotoxins such as lipopolysaccharide (LPS). LPS comprises the major constituents of the cell walls of gram-negative bacteria and is highly immunogenic and stimulates the production of endogenous pyrogens IL-1 and TNF (Sell et al., (1996) Immunology, Immunopathology & Immunity, Appleton & Lange). To test the effects of the NBD peptides on septic shock, mice are injected with the NBD peptides and LPS and the survival of animals assessed.

Example 11

Relative Contributions and Importance of Each Amino Acid Within the NBD to the Interaction with NEMO As indicated in the foregoing Examples, the NEMO binding domain (NBD) of IKKα and IKKβ consists of six conserved amino acids (L737 to L742 of IKKα and L738 to L743 of IKKα) in the extreme C-terminus of both kinases. This experiment was performed to obtain a clearer understanding of the relative contributions and importance of each amino acid within the foregoing NBDs to the interaction with NEMO. Extensive mutational analysis of the IKKα NBD was performed, in which each residue was substituted with various conserved and non-conserved amino acids.

It was determined that substitution of either leucine residue (L737 or L742) or serine 740 did not affect the association of NEMO with IKKβ suggesting that none of these residues play a critical role in maintaining the interaction. To determine whether multiple mutations of these amino acids will affect binding, two mutants were constructed in which either L737 and S740 or S740 and L742 (named LS and SL respectively) were substituted with alanine. GST pull-down and COS cell transfection-immunoprecipitation-immunoblot analysis has revealed that both LS and SL mutants associate with NEMO to the same extent as wild type IKKβ providing further evidence that these residues do not contribute significantly to the interaction. Furthermore, both LS and SL activate NF-kB as well as IKKβ when measured by activation of an NF-κB-dependent luciferase reporter construct (pBIIx-luciferase) in transient transfection assays. A double alanine mutant of both leucine residues (LL) as well as a triple mutant (LSL) may be useful in confirming the foregoing data regarding the importance of these residues to NEMO binding.

In contrast to the lack of effects of the mutations described above on either NEMO binding or NF-κB activation, alanine substitution of the aspartic acid residue within the NBD (D738) prevented IKKβ from associating with NEMO. Furthermore, this substitution led to a 2- to 3-fold increase in the basal NF-κB-acivating ability of IKKβ. These results demonstrate a role for NEMO association in maintaining the basal activity of the IKK complex. Interestingly, treatment of HeLa cells with the cell-permeable NBD peptide also led to a modest increase in basal NF-κB activity further supporting the concept that loss of NEMO association leads to increased basal IKK activity.

Figure 8A:
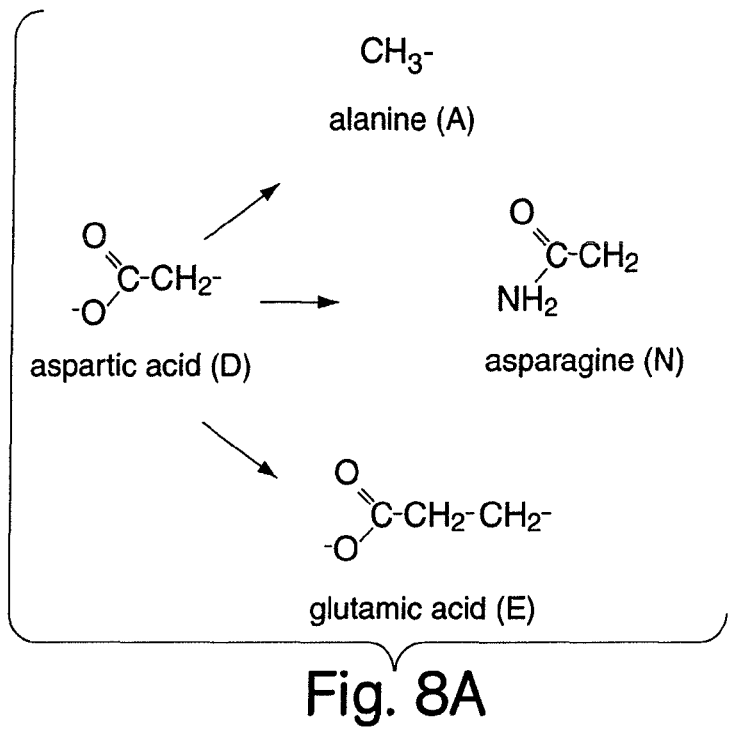
FIG. 8 depicts the results of a mutational analysis of D738 within the NEMO binding domain (NBD) of human IKKβ. (A) The aspartic acid residue at position 738 of IKKβ was substituted with either alanine, asparagine or glutamic acid using PCR-mutagenesis. (B) The IKKβ (D738) mutants shown in A were $^{35}$S-methionine-labeled by in vitro transcription and translation then used for GST pull-down analysis using GST-NEMO as previously described. (C) Hela cells were transiently transfected using the Fugene6 transfection method with the NF-κB-dependent reporter construct pBIIx-luciferase together with either pcDNA-3, IKKβ or the D738 mutants described above (A). After 48 hours, the cells were lysed and luciferase activity was determined as previously described.
Figure 8B:
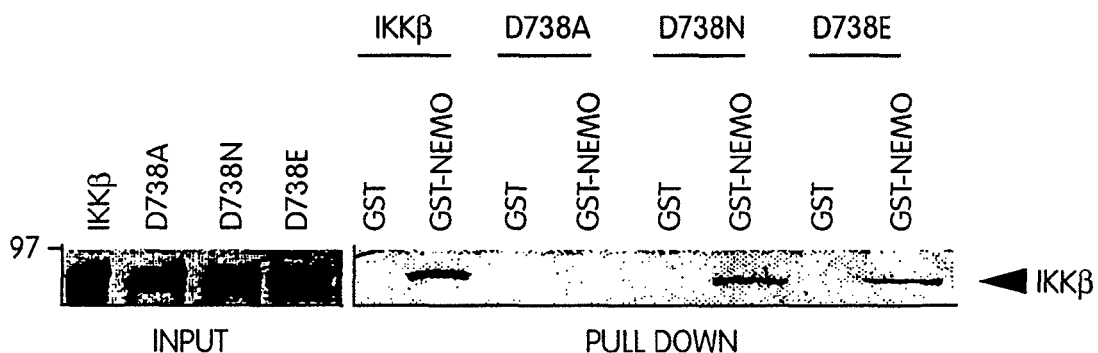
Figure 8C:
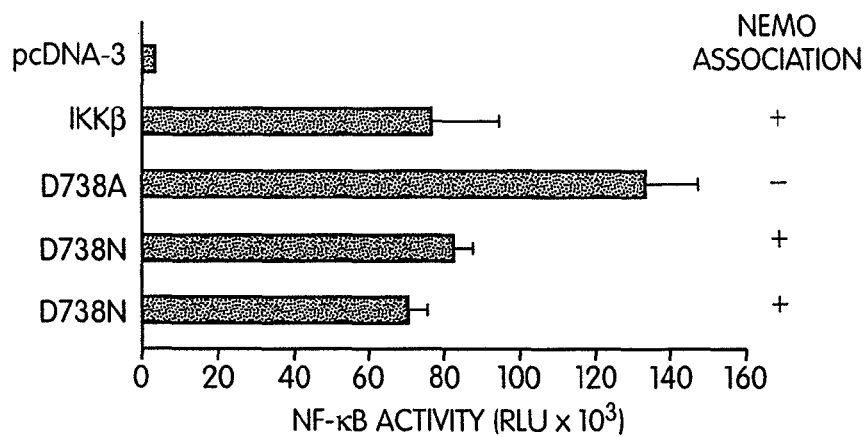

To investigate the nature of the residue at position 738 within the NBD, aspartic acid was substituted with either asparagine (D738N) or glutamic acid (D738E; FIG. 8A). These conservative substitutions maintain either the shape (N) or shape and charge (E) of the residue at this position. As shown in FIG. 8B, neither substitution affected the ability of IKKβ to associate with NEMO whereas alanine substitution prevented binding. These data demonstrate that it is the shape (specifically the presence of second carbon) and not the charge of the side chain of the amino acid at this position that is critical for the interaction between IKKβ and NEMO. Consistent with the previous observations disclosed herein, neither mutation affected the basal activity of IKKβ whereas substitution with alanine caused an increase in activity (FIG. 8C).

Figure 9A:
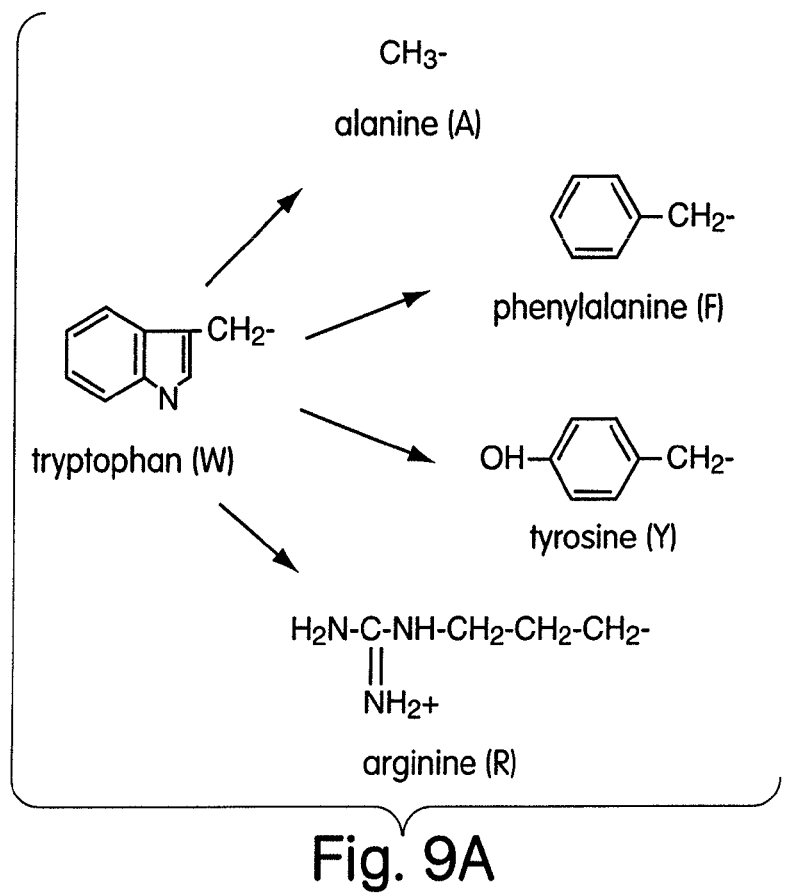
FIG. 9 depicts the results of a mutational analysis of W739 and W741 within the NBD of human IKKβ. (A) The tryptophan residues at positions 739 and 741 of IKKβ were substituted with alanine, phenylalanine, tyrosine or arginine using PCR-mutagenesis. (B) COS cells were transiently transfected with either vector alone (pcDNA-3.1-xpress), IKKβ, W739A, W739F or W739Y together with FLAG-tagged NEMO as shown. After 48 hours, the cells were lysed and complexes were immunoprecipitated (IP) using anti-FLAG (M2)-coupled agarose beads. Prior to immunoprecipitation a portion of each lystate (5%) was retained for analysis (pre-IP). Proteins in samples were separated by SDS-PAGE (10%) and analyzed by immunoblotting (IB) using antibodies recognizing either FLAG (M2) or xpress. The upper two panels show xpress-tagged IKKβ and the lower panel shows FLAG-tagged NEMO. (C and D) COS cells were transiently transfected with the plasmids shown followed by immunoprecipitation and immunoblot analysis as described in B. (C and D) Hela cells were transiently transfected with pBIIx-luciferase together with the plasmids shown and after 48 hours luciferase activity in lysates was determined.
Figure 9B:
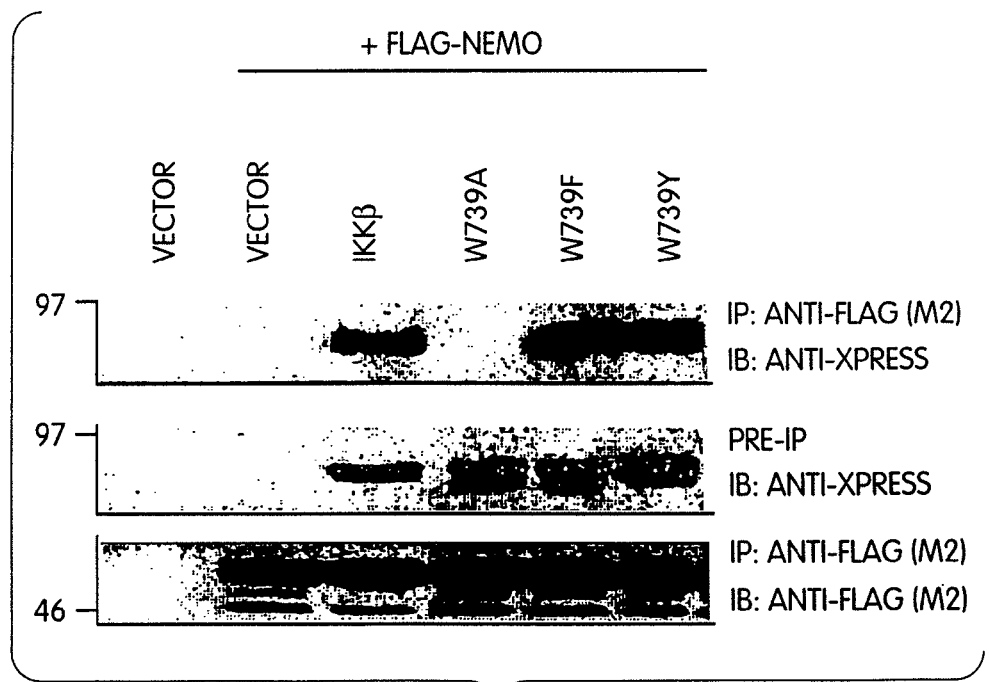
Figure 9C:
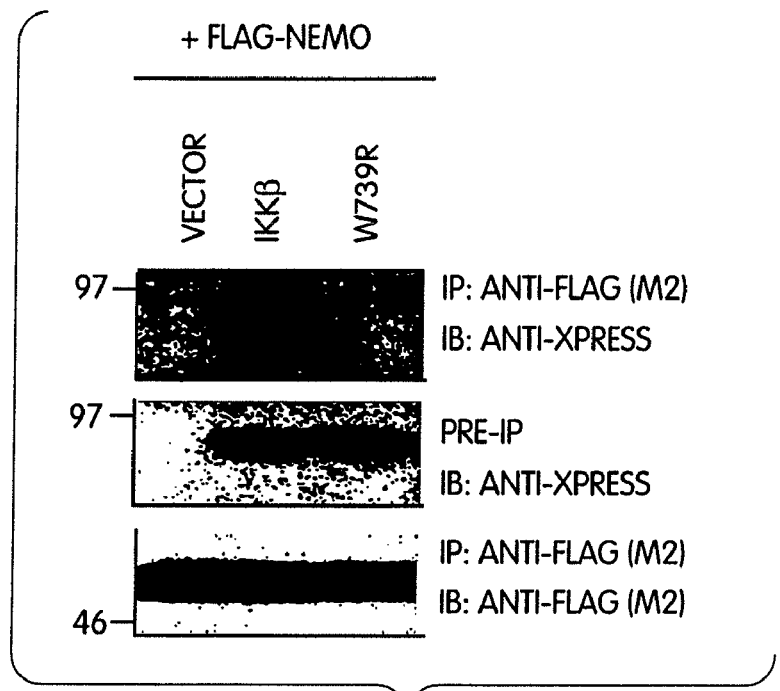
Figure 9D:
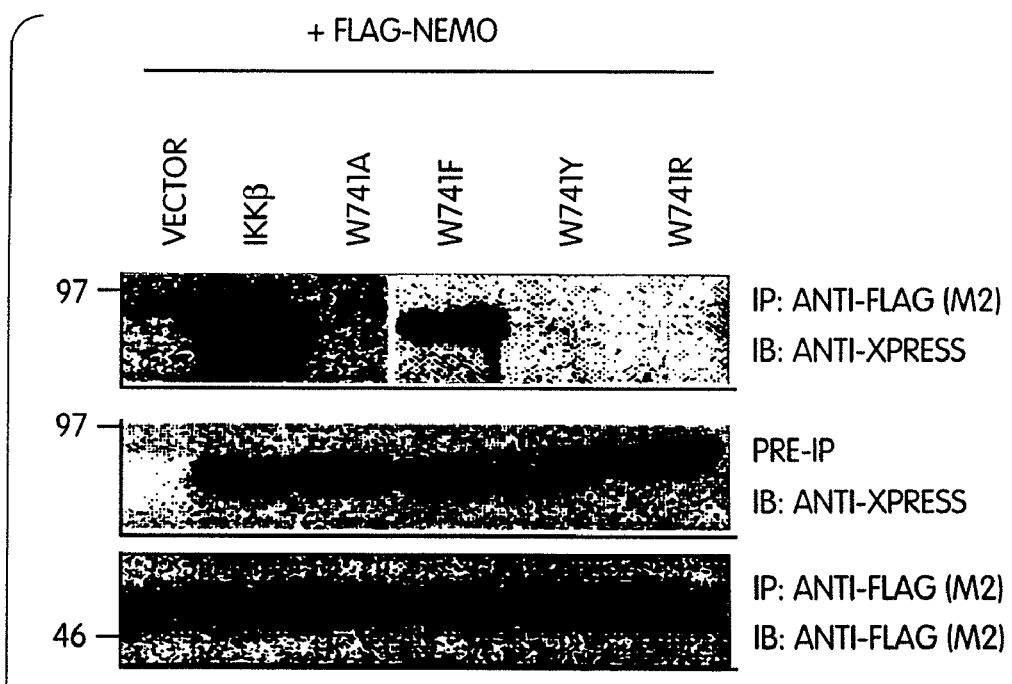
Figure 9E:
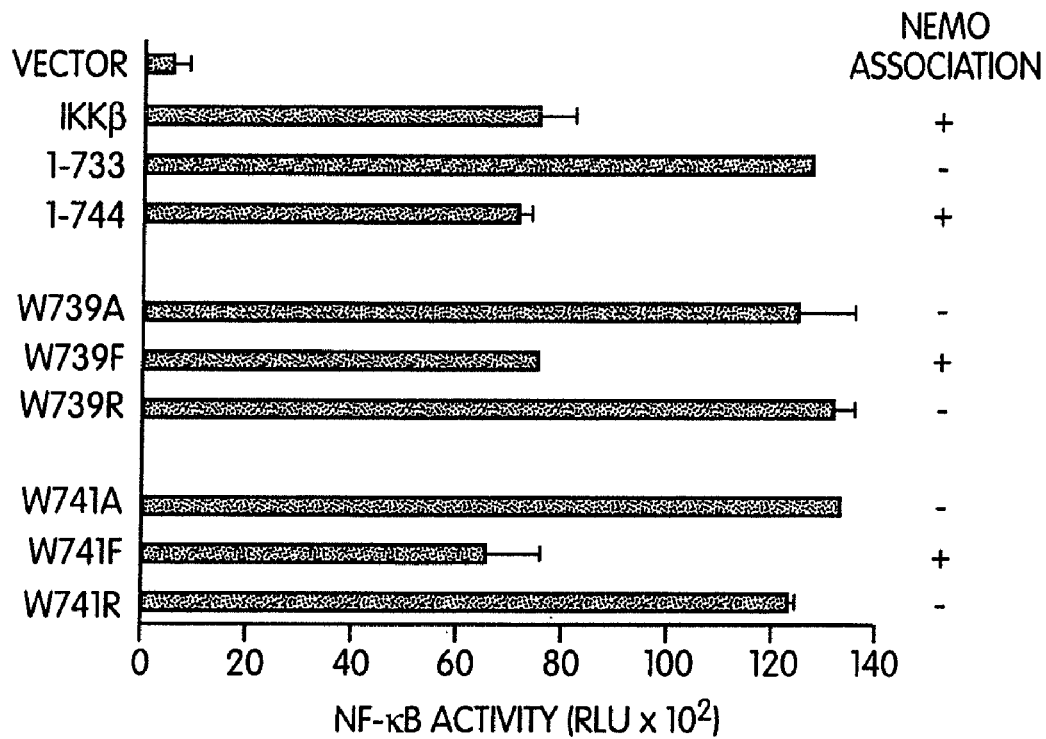
Figure 9F:
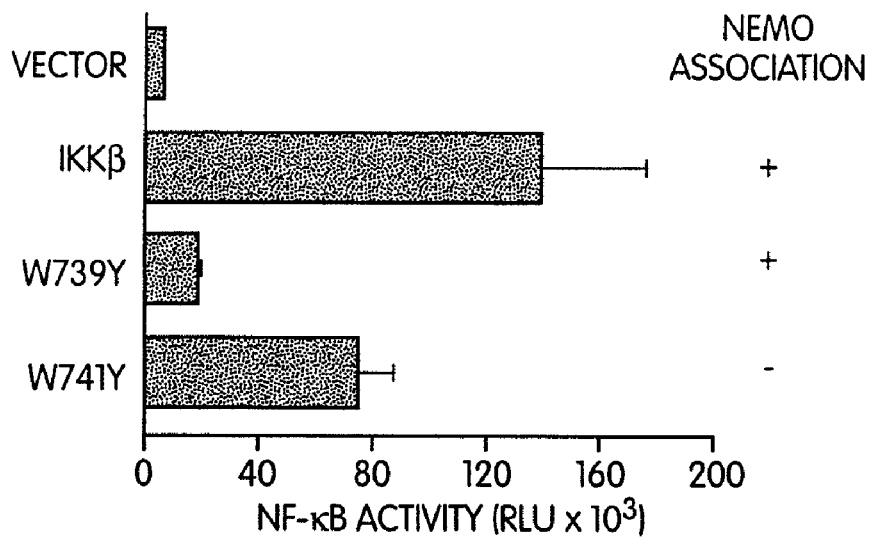
Figure 10A:
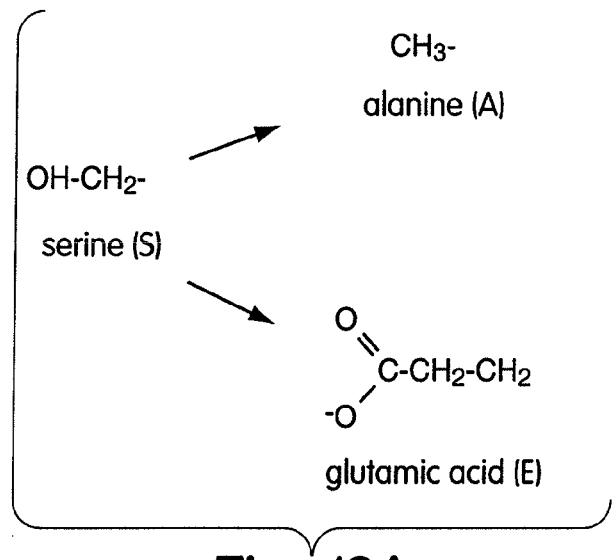
FIG. 10 depicts the results of a mutational analysis of S740 within the NBD of human IKKβ. The serine residues at position 740 of IKKβ was substituted with alanine or glutamic acid using PCR-mutagenesis. (B) COS cells were transiently transfected with the plasmids shown followed by immunoprecipitation and immunoblot analysis as described in FIG. 2B. (C) Hela cells were transiently transfected for 48 hours with either IKKβ-FLAG or S740E-FLAG then treated for the times shown with TNFα (1 μg/ml). Following lysis, complexes were precipitated using anti-FLAG (M2)-coupled agarose beads and an immune-complex kinase assay was performed using GST-IκBα (1-90) as a substrate as previously described.
Figure 10B:
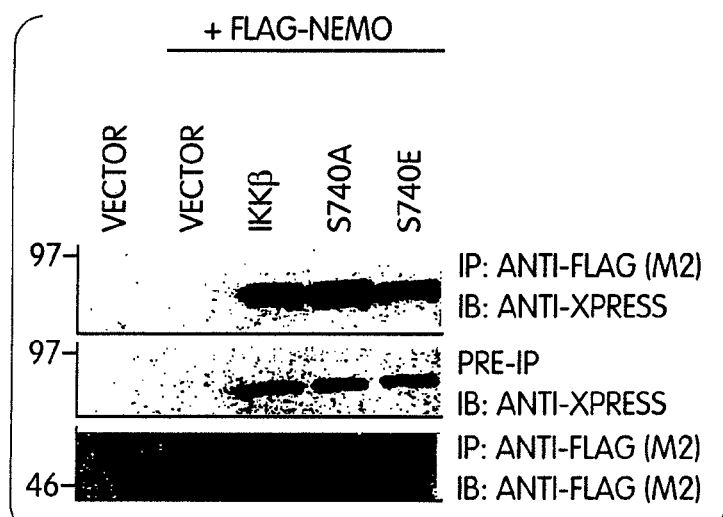
Figure 10C:
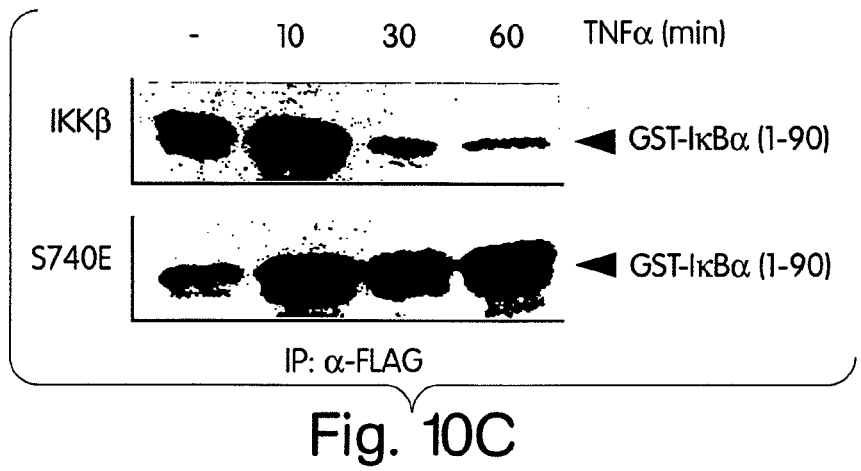
Figure 11A:
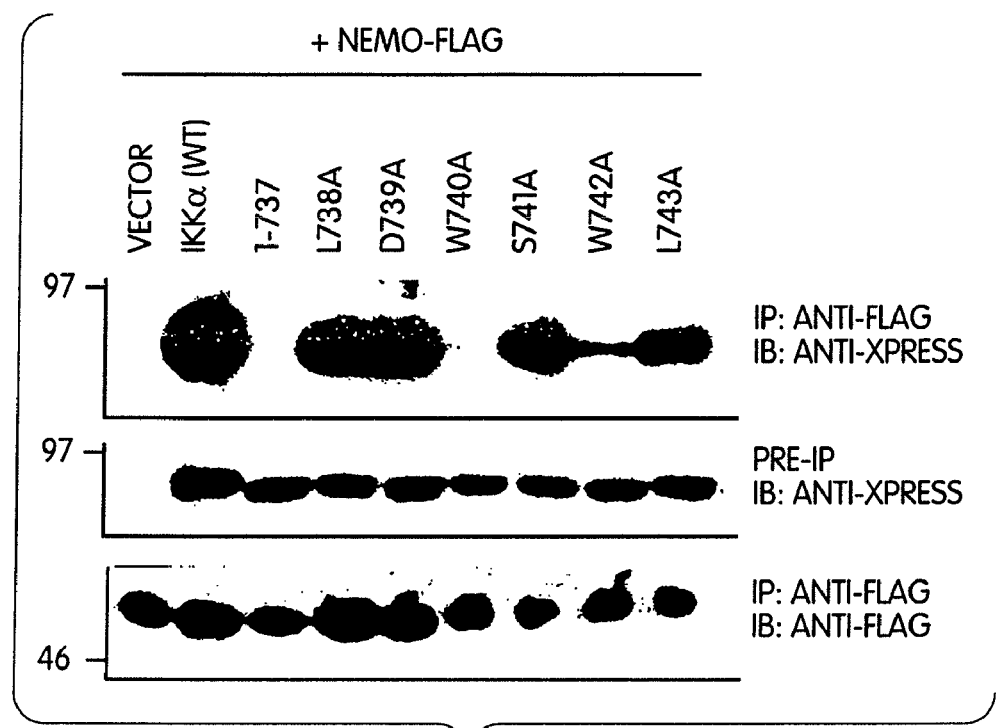
FIG. 11 depicts the results of a mutational analysis of the IKKα NBD. (A) Each of the residues that comprise the NBD of IKKα (L738 to L743) were substituted with alanine by PCR-mutagenesis. COS cells were transiently transfected with NEMO-FLAG together with either vector alone (pcDNA-3.1-xpress) or xpress-tagged versions of IKKα and the NBD mutants as shown. Immunoprecipitation and immunoblot analysis of the IKKα-NEMO complexes was performed as described in FIG. 2B. (B) Hela cells were transiently transfected with pBIIx-luciferase together with the plasmids shown and after 48 hours luciferase activity in lysates was determined.
Figure 11B:
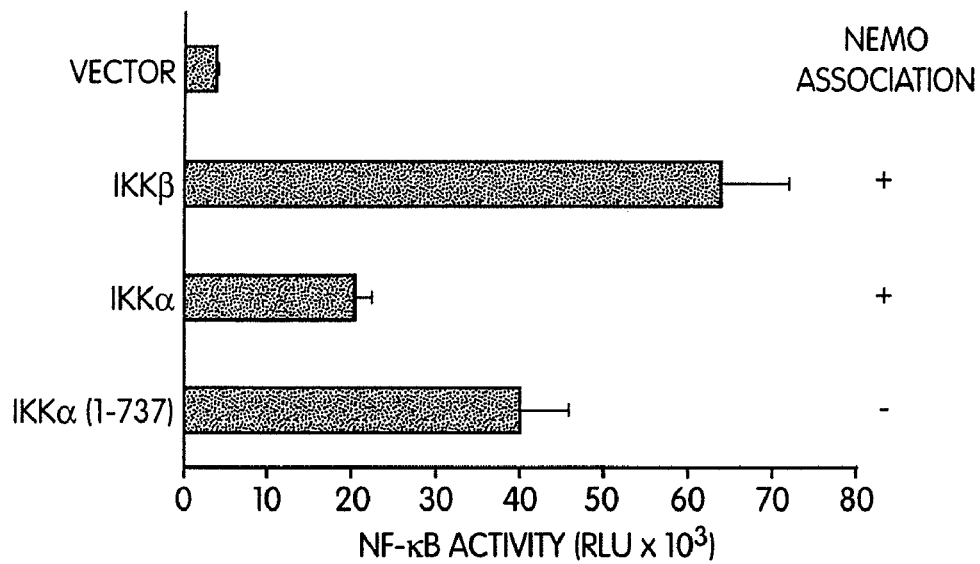
Figures 12A, 12B:
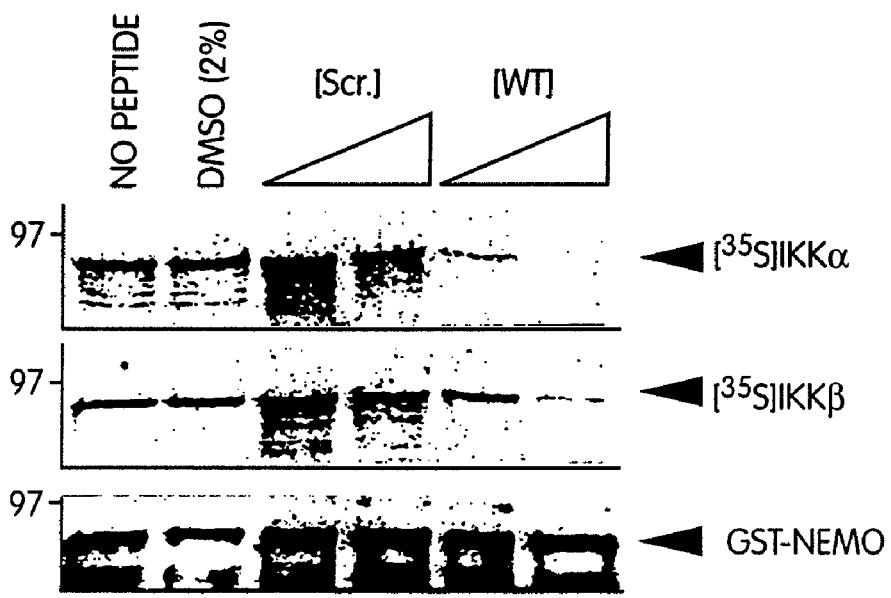
FIG. 12 depicts the results of an experiment demonstrating that a peptide encompassing the IKKβ NBD prevents the interaction of IKKα with NEMO. (A) Sequences of the NBD wild type and scrambled control peptides. The wild type peptide corresponds to residues 734 to 744 of IKKβ. (B) GST pull-down analysis was performed using GST-NEMO and in vitro transcribed and translated IKKα (upper panel) and IKKβ (middle panel) in the presence or absence of either vehicle (2% DMSO), scrambled or wild type NBD peptide (500 and 1000 μM of each peptide). The lower panel shows a coomassie blue-stained gel demonstrating that neither peptide affects the interaction of GST-NEMO with the glutathione-agarose beads used for precipitation. (C) Densitometric analysis of autoradiograph bands obtained following GST pull-down of IKKa and IKKb using GST-NEMO in the presence of a range of concentrations of wild type NBD peptide. The inset shows a representative experiment. The data are presented as the pixel density as a percentage of control (no peptide) and represent means±sd (n=11). Analysis was performed using the NIH-Image software.
Figure 12C:
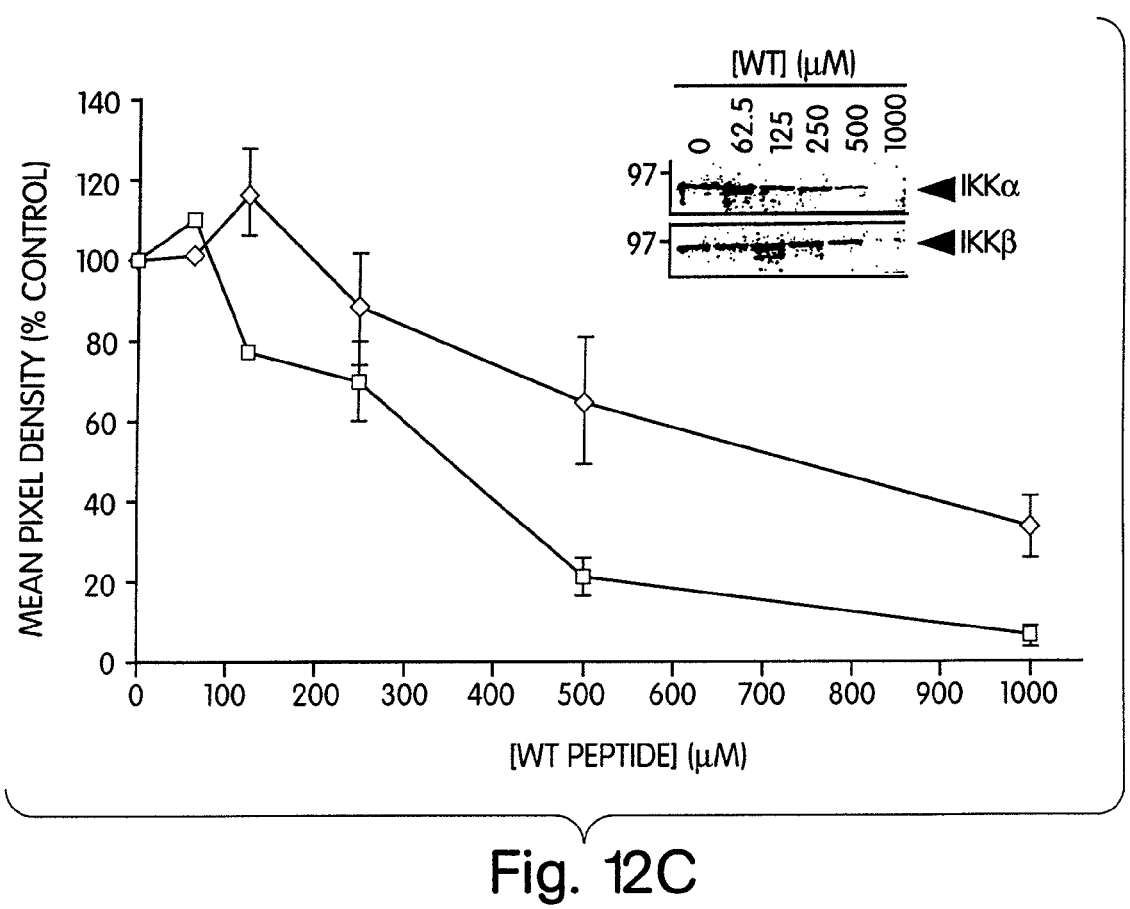

As indicated above, both tryptophan residues within the NBD (W739 and W741) are critical for maintaining the interaction with NEMO. The effects of conservative mutations that maintain the aromatic structure of the residues at these positions was investigated by substituting either phenylalanine (F) or tyrosine (Y) for tryptophan (FIG. 9A). In addition, both tryptophans were mutated to arginine; a non-conservative substitution requiring only a single base change within the encoding codon that is the most common naturally occurring tyrptophan mutation. As shown in FIG. 9B, both W739F and W739Y mutants associated with NEMO to the same extent as IKKβ whereas W739R did not bind (FIG. 9C). Together with the effects of alanine substitution (FIG. 9B), these findings indicate that the aromatic nature of the residue at this position is critical for the function of the NBD. Similar to W739, it was determined that substitution of W742 with phenylalanine (W742F) did not affect association with NEMO, whereas mutation to arginine (W742R) prevented binding (FIG. 9D). In contrast to W739, substitution with tyrosine (W742Y) prevented association with NEMO demonstrating that the presence of a hydroxyl moiety within the amino acid side chain at this position is sufficient to prevent association of NEMO. This finding may indicate the that phosphorylation of a residue within the NBD, albeit an artificially inserted amino acid, prevents association of IKKβ with NEMO.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A method of modulating NF-κB induction in a cell comprising contacting a cell with an effective amount of an anti-inflammatory compound comprising at least one NF-kB Essential Modulator (NEMO) binding domain fused with at least one cell membrane translocation domain, wherein the anti-inflammatory compound is less than one-hundred amino acids in length, and wherein the anti-inflammatory compound inhibits NF-κB activation, thereby modulating NF-κB induction in a cell.

2. The method of claim 1, wherein the anti-inflammatory compound blocks the interaction between one or more IKKs and NEMO.

3. The method of claim 2, wherein the IKK is selected from the group consisting of IKKα and IKKβ.

4. The method of claim 1, wherein the NEMO binding domain comprises an amino acid sequence selected from the group consisting of SEQ ID NO:2, 3, 4, 5, 7, 8, 9, 10, 11, 12, 13, 14, 15, 16, 17, 18, and 19.

5. A method for treating a subject suffering from an inflammatory disorder comprising administering to said subject an effective amount of anti-inflammatory compound comprising at least one NF-kB Essential Modulator (NEMO) binding domain fused with at least one cell membrane translocation domain, wherein the anti-inflammatory compound is less than one-hundred amino acids in length, and wherein the anti-inflammatory compound inhibits NF-κB activation, thereby treating said subject suffering from an inflammatory disorder.

6. The method of claim 5, wherein the anti-inflammatory compound inhibits the recruitment of leukocytes into sites of acute and chronic inflammation.

7. The method of claim 5, wherein the anti-inflammatory compound down-regulates the expression of E-selectin on endothelial cells.

8. The method of claim 5, wherein the anti-inflammatory compound inhibits osteoclast differentiation.

9. A method of modulating NF-κB-dependent target gene expression in a cell comprising contacting a cell with an effective amount of an anti-inflammatory compound comprising at least one NF-κB Essential Modulator (NEMO) binding domain fused with at least one cell membrane translocation domain, wherein the anti-inflammatory compound is less than one-hundred amino acids in length, and wherein the anti-inflammatory compound inhibits NF-κB activation, thereby modulating NF-κB-dependent target gene expression in a cell.

10. The method of claim 9, wherein the anti-inflammatory compound blocks the interaction between one or more IKKs and NEMO.

11. The method of claim 10, wherein the IKK is IKKβ.

12. The method of claim 9, wherein the NF-κB-dependent target gene is E-selectin.

13. A method of treating an NFkB-mediated condition in a subject, comprising administering to the subject an anti-inflammatory compound comprising at least one NF-κB Essential Modulator (NEMO) binding domain fused with at least one cell membrane translocation domain, wherein the anti-inflammatory compound is less than one-hundred amino acids in length, and wherein the anti-inflammatory compound inhibits NF-κB activation, in an amount and for a period of time effective to inhibit the binding of NF-κB Essential Modulator (NEMO) to an IκB protein kinase (IKK), thereby treating an NFkB-mediated condition in a subject.

14. The method of claim 13, wherein the NFkB-mediated condition is an inflammation disorder, an autoimmune disease, transplant rejection, osteoporosis, cancer, Alzheimer's disease, atherosclerosis, a viral infection, or ataxia telangiectasia.

15. The method of claim 14, wherein the inflammation disorder is selected from the group consisting of asthma, allergies, uticaria, anaphylaxis, cutaneous inflammation, sepsis, psoriasis, rheumatoid arthritis, osteoarthritis, psoriatic arthritis, inflammatory bowel disease, chronic obstructive pulmonary disease, vasculitis, and bursitis.

16. The method of claim 14, wherein the inflammation disorder is selected from the group consisting of dermititis, eczema, psoriasis, osteoarthritis, psoriatic arthritis, lupus and spondylarthritis.

17. The method of claim 13, wherein the membrane translocation domain is selected from the group consisting of the third helix of the *antennapedia* homeodomain and HIV-1 Tat protein.

18. The method of claim 13, wherein the NEMO binding domain comprises an amino acid sequence selected from the group consisting of SEQ ID NO: 2, 3, 4, 5, 6, 7, 8, 9, 10, 11, 12, 13, 14, 15, 16, 17, 18, and 19.

19. The method of any one of claims 1, 5, 9, or 13, wherein the compound is a small molecule.

20. The method of claim 1, wherein the compound modulates NF-κB-dependent target gene expression.

21. The method of claim 20, wherein the NF-κB-dependent target gene is E-selectin.

22. The method of claim 1, wherein the compound modulates NF-κB induction.

23. The method of claim 1, wherein the compound inhibits osteoclast differentiation.

24. The method of claim 1 or 9, wherein the cell is contacted in vivo.

25. The method of claim 1 or 9, wherein the cell is contacted in vitro.

* * * * *

UNITED STATES PATENT AND TRADEMARK OFFICE
CERTIFICATE OF CORRECTION

PATENT NO. : 7,872,094 B2
APPLICATION NO. : 12/424334
DATED : January 18, 2011
INVENTOR(S) : Michael J. May et al.

Page 1 of 1

It is certified that error appears in the above-identified patent and that said Letters Patent is hereby corrected as shown below:

In Claim 13, column 48, line 13 replace "NFkB-mediated" with -- NF-κB-mediated --

In Claim 14, column 48, line 14 replace "NFkB-mediated" with -- NF-κB-mediated --

Signed and Sealed this
Nineteenth Day of June, 2012

David J. Kappos
*Director of the United States Patent and Trademark Office*